US006963807B2

(12) United States Patent
Townsend et al.

(10) Patent No.: US 6,963,807 B2
(45) Date of Patent: Nov. 8, 2005

(54) AUTOMATED IDENTIFICATION OF PEPTIDES

(75) Inventors: Robert Reid Townsend, Oxford (GB); Andrew William Robinson, Saskatoon (CA)

(73) Assignee: Oxford Glycosciences (UK) Ltd., Berks (GB)

( * ) Notice: Subject to any disclaimer, the term of this patent is extended or adjusted under 35 U.S.C. 154(b) by 335 days.

(21) Appl. No.: 09/950,313

(22) Filed: Sep. 10, 2001

(65) Prior Publication Data

US 2002/0102610 A1 Aug. 1, 2002

Related U.S. Application Data

(60) Provisional application No. 60/232,273, filed on Sep. 13, 2000.

(30) Foreign Application Priority Data

Sep. 8, 2000 (GB) .............................. 0022136

(51) Int. Cl.[7] .......................... G06F 17/00; G06F 17/30
(52) U.S. Cl. .............................. 702/27; 702/19; 702/22; 702/23; 436/89; 436/173
(58) Field of Search .............................. 702/19, 22, 23, 702/27, 20; 436/89, 173, 94; 530/334–337

(56) References Cited

U.S. PATENT DOCUMENTS

| | | | |
|---|---|---|---|
| 4,224,031 A | 9/1980 | Mee et al. ..................... | 23/230 |
| 4,543,340 A | 9/1985 | Goldstein et al. | |
| 4,701,419 A | 10/1987 | Morris ......................... | 436/89 |
| 4,820,648 A | 4/1989 | Caprioli et al. .............. | 436/89 |
| 4,861,988 A | 8/1989 | Henion et al. ............... | 290/288 |
| 5,003,059 A | 3/1991 | Brennan ...................... | 536/27 |
| 5,010,175 A | 4/1991 | Rutter et al. ................ | 530/334 |
| 5,045,694 A | 9/1991 | Beavis et al. ............... | 250/287 |
| 5,103,093 A | 4/1992 | Sakairi et al. .............. | 250/288 |
| 5,135,870 A | 8/1992 | Williams et al. ............ | 436/173 |
| 5,221,518 A | 6/1993 | Mills .......................... | 422/62 |
| 5,240,859 A | 8/1993 | Aebersold .................... | 436/89 |
| 5,246,865 A | 9/1993 | Stolowitz .................... | 436/89 |
| 5,288,644 A | 2/1994 | Beavis et al. ................ | 436/94 |
| 5,427,744 A | 6/1995 | Parekh et al. ............... | 422/116 |
| 5,432,093 A | 7/1995 | Bailey et al. ................ | 436/89 |
| 5,453,247 A | 9/1995 | Beavis et al. ............... | 422/68.1 |
| 5,470,753 A | 11/1995 | Sepetov et al. ............. | 436/89 |
| 5,510,240 A | 4/1996 | Lam et al. ................... | 435/7.1 |
| 5,521,097 A | 5/1996 | Uchida et al. ............... | 436/86 |
| 5,527,675 A | 6/1996 | Coull et al. ................. | 435/6 |
| 5,534,440 A | 7/1996 | Aebersold .................... | 436/89 |
| 5,538,897 A | 7/1996 | Yates, III et al. ........... | 436/89 |
| 5,547,835 A | 8/1996 | Köster ........................ | 435/6 |
| 5,565,171 A | 10/1996 | Dovichi et al. ............. | 422/68.1 |
| 5,580,733 A | 12/1996 | Levis et al. .................. | 435/6 |
| 5,952,653 A | 9/1999 | Covey et al. ............... | 250/288 |
| 6,146,866 A | 11/2000 | Viitanen et al. ............ | 435/193 |

FOREIGN PATENT DOCUMENTS

| | | | | |
|---|---|---|---|---|
| WO | WO 92/00091 A1 | 1/1992 | .......... | A61K/37/02 |
| WO | WO 98/52129 A1 | 11/1998 | .......... | G06F/17/30 |
| WO | WO 98/53323 A1 | 11/1998 | .......... | G01N/33/68 |
| WO | WO 99/15875 A1 | 4/1999 | .......... | G01N/1/08 |
| WO | WO 99/62930 A2 | 12/1999 | | |

OTHER PUBLICATIONS

US 5,382,513, 1/1995, Lam et al. (withdrawn)
Wilm, M.; Neubauer, G.; Taylor, L.; Shevchenko, A.; Bachi, A. De novo sequencing of proteins with mass spectrometry using the differential scanning technique Proteome and Protein Analysis (2000), 65–79, Editor(s): Kamp, Roza Maria; Kyriakidis, D.*
Gras, R. et al. Electrophoresis (1999), 20(18), 3535–3550.*
Traini, et al. Electrophoresis (1998), 19(11), 1941–1949.*
Johnson, R et al. Methods in Molecular Biology (Totowa, New Jersey) (2000), 146(Mass Spectrometry of Proteins and Peptides), 41–61.*
Berndt, P. et al. Electrophoresis (1999), 20(18), 3521–3526.*
Korostensky, C. et al. Electrophoresis (1998), 19(11), 1933–1940.*
Clauser et al., 1999, "Role of Accurate Mass Measurement (+–10 ppm) in protein identification strategies employing MS or MS/MS and Database searching", Anal. Chem. 71:2871–2882.
Karl Clauser, Description, Instructions, and Tips for MS–Tag, http:\\rafael.ucsf.edu/instruct/tagman.html, revised Mar. 13, 1997, date of origin unknown.
Currie et al., "Analysis of Oligodeoxynucleotides by Negative–Ion Matrix–Assisted Laser Desorption Mass Spectrometry", 1993, J Am Soc Mass Spectrom 4:955–963.
Eng et al., "An Approach to Correlate Tandem Mass Spectral Data of Peptides with Amino Acid Sequences in a Protein Database", 1994, J Am Soc Mass Spectrom 5:976–989.

(Continued)

Primary Examiner—Michael Borin

(57) ABSTRACT

A fully automated, user-independent method is described for computer-mediated interpretation of data derived by mass spectrometry of an experimental peptide to identify and characterize a corresponding peptide sequence in a peptide database. The method identifies the corresponding sequence if it is present in the database, without the need for a skilled observer to choose from amongst a list of possible matches. By using an automated back-read process, the present method can uniquely identify a corresponding peptide sequence in a database based on a single matching peptide sequence. The method also permits mapping of mass spectral data to sequences in peptide or nucleotide databases for unambiguous identification of exons; determining a correct reading frame; identifying artefacts and errors in sequences; identifying mutations and polymorphisms; identifying post-translational modifications; and identifying exon-intron boundaries.

25 Claims, 15 Drawing Sheets

OTHER PUBLICATIONS

Fernandez–de–Cossio et al., 1998, "Automated Interpretation of High energy collision induced dissociation spectra of singly protonated peptides by 'seqMS', a software aid for De Novo sequencing by tandem mass spectrometry", Rapid. Commun. Mass. Spectrom. 12:1867–1878.

Figeys et al. "Protein identification by solid phase microextraction–capillary zone electrophoresis–microelectrospray–tandem mass spectrometry", 1996, Nature Biotech. 14:1579–1583.

Griffin et al., "Direct Database Searching with MALDI–PSD Spectra of Peptides", 1995, Rapid Comm. in Mass Spectrom. 9:1546–1551.

Griffin et al., "Structural analysis of proteins by capillary HPLC electrospray tandem mass spectrometry", 1991, Intl. J Mass Spectrom & Ion Proc 111:131–149.

Hamm et al., Peptide Sequencing Program, CABIOS 2 1986, pp. 115–118.

Hayden et al., "Analysis of Naturally Processed Peptides Eluted From HLA DRB1*0402 and *0404", 1996, J. Neurosci. Res. 45:795–802.

Hunt et al., "Amino Acid Sequence Analysis of Two Mouse Calbindin–$D_{gk}$ Isoforms by Tandem Mass Spectrometry", J. Biol. Chem. 264:11/6580–6586.

Hunt et al., "Peptide Sequence Analysis by Laser Photodissociation Fourier Transform Mass Spectrometry", 1987, J. Chem. Soc., Chem. Commun. 548–550.

Hunt et al., "Tandem quadrupole Fourier–transform mass spectrometry of oligopeptides and small proteins", 1987, Proc. Natl. Acad. Sci. USA 84:620–623.

Hunt et al., "Tandem Quadrupole–Fourier Transform Mass Spectrometry of Oligopeptides", 1985, Anal. Chem. 57:2728–2733.

Hunt et al., 1986, "Protein Sequencing by tanden mass spectrometry", Proc. Natl. Acad. Sci USA 83:6233–6237.

James et al., 1993, "Protein identification by mass profile fingerprinting"Biochem Biophys Res Commun. 195(1):58–64.

Jensen et al., 1997, "Identification of the components of simple protein mixtures by high accuracy peptide mass mapping and database searching", Anal. Chem. 69:4741–4750.

Jonscher et al., "Matrix–assisted Laser Desorption Ionization/Quadrupole Ion Trap Mass Spectrometry of Peptides", 1997, J. Biol. Chem. 272:3/1735–1741.

Jonscher et al., "Matrix–assisted Laser Desorption of Peptides and Proteins on a Quadrupole Ion Trap Mass Spectrometer", 1993, Rapid Comm. Mass Spectrom. 7:20–26.

Jonscher et al., "Mixture Analysis Using a Quadrupole Mass Filter/Quadrupole Ion Trap Mass Spectrometer", 1996, Anal. Chem. 68:659–667.

Jonscher et al., "The Quadrupole Ion Trap Mass Spectrometer—A Small Solution to a Big Challenger", 1997, Anal. Biochem. 244:1–15.

Keen et al., "Protein Sequenceing Techniques", Mol. Biol. Biotech., 771–773, ed. Meyers.

Krishnamurthy et al., "Structural characterization of toxic cyclic peptides from blue–green algae by tandem mass spectrometry", 1989, Proc. Natl. Acad. Sci. USA 88:770–774.

Link et al., "Analyzing complex biological systems using micro–LC–ESI–MS–MS", 1998, American Laboratory 27–30.

McCormack et al., "Direct Analysis and Identification of Proteins in Mixtures by LC/MS/MS and Database Searching at the Low–Femtomole Level", 1997 Anal. Chem. 69:767–776.

McCormack et al., "Localization of the Disulfide Bond Involved in Post–translational Processing of Glycosylasparaginase and Disrupted by a Mutation in the Finnish–type Aspartylglycosaminuria", 1995, J. Biol. Chem. 270:7/3212–3215.

McCormack et al., "Peptide Sequence Analysis of Quadrupole Mass Spectrometers", 1994, Methods 6:274–283.

Moore et al., "Proteolytic Fragments of the Nicotinic Acetylcholine Receptor Identified by Mass Spectrometry: Implications for Receptor Topography", 1989, Biochemistry 28:9184–9191.

Neubauer et al., 1997, "Identification of the proteins of the yeast U1 small nuclear ribonucleoprotein complex by mass spectrometry", Proc. Natl. Acad. Sci. USA 94:385–390.

Pappin et al., 1993, "Rapid identification of proteins by peptide–mass fingerprinting", Current Biology 3:327–332.

Sakurai et al., 1984, A Computer Program to Determine Probable Sequence of Peptides from Mass Spectrometric Data, *Biomed Mass Spec.* 11:396.

Scarberry et al., "Peptide Sequence Determination from High–Energy Collision–Induced Dissociation Spectra Using Articificial Neural Networks," J Am Soc Mass Spectrom 1995, 6, 947–961.

Sepetov et al., 1993, "The use of hydrogen deuterium exchange to facilitate peptide sequencing by electrospray tandem mass spectrometry", Rapid Commun. Mass Spectrom. 7:58–62.

Shevchenko et al., "Rapid 'de Novo' Peptide Sequencing by a Combination of Nanoelectrospray, Isotopic Labeling and a Quadrupole/Time–of–flight Mass Spectrometer," Rapid Communications in Mass Spectrometry, vol. 11, 1015–1024 (1997).

Shevchenko et al., 1996, Linking genome and proteome by mass spectrometry: large–scale identification of yeast proteins from two dimensional gels. Proc Natl Acad Sci U S A. 93(25):14440–5.

Siegel and Bauman, 1988, "An efficient algorithm for sequencing peptides using fast atom bombardment mass spectral data", Med. And Environ. Mass Spectrom. 15:333–343.

Taylor et al., "Sequence Database Searches via de Novo Peptide Sequencing by Tandem Mass Spectrometry," Rapid Communications in Mass Spectrometry, vol. 11, 1067–1075 (1997).

Ward et al., "Proteins and Peptides, Isolation for Sequence Analysis of", Mol. Biol. Biotech., 767–771, ed. Meyers.

Williams et al., "Protein Analysis by Integrated Sample Preparation, Chemistry, and Mass Slpectrometry", Mol. Biol. Biotech., 731–737, ed. Meyers.

Wilm and Mann, 1996, "Analytical Properties of the Nanoelectroscopy Ion source", Anal. Chem 68:1–8.

Wilm et al., "Simplified "de novo" sequencing with quadrupole or quadrupole TOF instruments for finding homologous proteins or for cloning".

Yates et al., "Future Prospects for the Analysis of Complex Biological Systems Using Micro–column, Liquid Chromatography–Electrospray Tandem Mass Spectrometry", 1996, Analyst 121:65R–76R.

Yates et al., "Method to Correlate Tandem Mass Spectra of Modified Peptides to Amino Acid Sequences in the Protein Database", 1995, Anal. Chem. 67:1426–1436.

Yates et al., "Mining Genomes: Correlating Tandem Mass Spectra of Modified and Unmodified Peptides to Sequences in Nucleotide Databases", 1995, Anal. Chem. 67:3202–3210.

Yates et al., "Mining Genomes with MS", 1996, Anal. Chem. News & Features 534A–540A.

Yates et al., "Mixed Gas Chemical Ionization Mass Spectrometry of Peptide Derivatives", Biomed. Mass Spectrom. 10:10/567–571.

Yates et al., "Peptide Mass Maps: A Highly Informative Approach to Protein Identification", 1993, Anal. Biochem. 214:397–408.

Yates et al., "Search of Sequence Databases with Uninterpreted High–Energy Collision–Induced Dissociation Spectra of Peptides", 1996, J Am Soc Mass Spectrom, 1996, 7:1089–1098.

Yates et al., 1997, "Protein Sequencing by Tandem Mass Spectrometry", UMI Dissertation Services.

Bartels C. "Fast Algoithm for Peptide Sequencing by Mass Spectroscopy", 1990, 19:363–368.

Dongre et al. "Emerging tandem–mass–spectrometry techniques for the rapid identification of proteins", Trends Biotechnol. 1997, 15(10):418–425.

Lindh et al., "De novo sequencing of proteolytic peptides by a combination of C–terminal derivatization and nano–electrospray/collision–induced dissociation mass spectrometry", J Am Soc Mass Spectrom. 2000, 11(8):673–686.

* cited by examiner

NOMENCLATURE OF IONS IN A FRAGMENTATION MASS SPECTRUM

SEARCH STRING STRUCTURE AND DATABASE ATTRIBUTES FOR UNIQUE IDENTIFICATION OF TRANSLATED SEQUENCES FROM THE HUMAN GENOME

Search string

$$M_1 \text{----} T \text{----} M_2$$

$$(258.08) \text{--} AEN \text{--} (732.39)$$

Sequence in database

$$NH_2 \text{-----} (R) \text{-} EE \text{-----} AEN \text{---} TLQSFR \text{-----} COOH$$

$$\phantom{NH_2 \text{-----} (R) \text{-} EE \text{-----} } 1 \phantom{xx} 2 \phantom{xx} 3$$

Constraints for search string

1. $M_1$ - The value cannot equal the mass of a single naturally-occurring amino acid residue.

2. Trimer sequence - The three sequential amino acid residues taken from the HOPS and/or TESLA candidate sequence. Only a single permuted residue (L<-> I, or F<-> M*) is allowed within the trimer.

3. $M_2$ - The mass of $M_2$ must be greater than 156.10.

Allowed database sequences

1. The nearest neighbor on the N-terminal of the retrieved sequence must be either a K or R residue.

2. M1 cannot contain a K or R residue, unless followed by a P residue.

3. The peptide sequence must terminate in K or R and cannot contain additional K or R residues unless followed by a P residue (C-terminal).

FIG.10

RETRIEVAL OF HUMAN GENOME SEQUENCES USING A SEARCH STRING, AND PEPTIDE SEQUENCE MAPPING

| Sequence No | Accession No. | Frame | |
|---|---|---|---|
| 1 | AF187320 | +1 | |
| 2 | AF187320 | +3 | VQLWNFVSLGFMIGYLGYCKGVEPK |
| 3 | AC016953 | -2 | |
| 4 | AC016953 | -3 | VQLWNFVSLGFMIGYLGYCKGVEPK |
| 5 | AC024937 | -2 | VQLWNFVSLGFMIGYLFFLIGFMIGYLGYCKGVEPK |
| 6 | 6164848 | | MMDQARSAFSNLFGGEPLSYTRFSLARQVDGDNSHVEMKLAVDEEENADNNTKANVTKPKRCSGSICYGTIAVIVFFLIGFMIGYLGYCKGVEPK |

| Accession | Frame | |
|---|---|---|
| AF187320 | +1 | VHLKGIFSS.RLLNENSYVPREAGSQKDENLALYVENQFREFKLSKVWRDQHFVKI |
| AF187320 | +3 | TECERLAGTESPVREEPGEDFPAARRLYWDDLKRKLSEKLDSTDFTGTIK |
| AC016953 | -2 | TECERLAGTESPVREEPGEDFPAARRLYWDDLKRKLSEKLDSTDFTGTIK VHLKGIFSS.RLLNENSYVPREAGSQKDENLALYVENQFREFKLSKVWRDQHFVKI |
| AC016953 | -3 | TECERLAGTESPVREEPGEDFPAARRLYWDDLKRKLSEKLDSTDFTGTIK |
| AC024937 | -2 | TECERLAGTESPVREEPGEDFPAARRLYWDDLKRKLSEKLDSTDFTGTIKLLNENSYVPREAGSQKDENLALYVENQFREFKLSKVWRDQHFVKI |
| 6164848 | | |

| Accession | Frame | |
|---|---|---|
| AF187320 | +1 | QVKDRYVERW |
| AF187320 | +3 | |
| AC016953 | -2 | QVKDRYVERW |
| AC016953 | -3 | |
| AC024937 | -2 | |
| 6164848 | | QVKDSAQNSVIIVDKNGRLVYLVENPGGYVAYSKAATVTGKLVHANFGTKKDFEDLYTPVNGSIVIVRAGKITFAEKVANAESLNAIGVLIYMDQ |

FIG. 12A

| Accession | Frame | |
|---|---|---|
| AF187320 | +1 | |
| AF187320 | +3 | |
| AC016953 | -2 | |
| AC016953 | -3 | |
| AC024937 | -2 | |
| 6164848 | | TKFPIVNAELSFFGHAHLGTGDPYTPGFPSFNHTQFPPSRSSGLPNIPVQTISRAAAEKLFGNMEGDCPSDWKTDSTCRMVTSESKNVKLTVSNV |

| Accession | Frame | |
|---|---|---|
| AF187320 | +1 | |
| AF187320 | +3 | |
| AC016953 | -2 | |
| AC016953 | -3 | |
| AC024937 | -2 | |
| 6164848 | | LKEIKILNIFGVIKGFVEPDHYVVVGAQRDAWGPGAAKSGVGTALLLKLAQMFSDMVLKDGFQPSRSIIFASWSAGDFGSVGATEWLEGYLSSLH |

| Accession | Frame | |
|---|---|---|
| AF187320 | +1 | PRIVSQDTDYPYLGTTM |
| AF187320 | +3 | PRVVLQDTDYPYLGPTM |
| AC016953 | -2 | |
| AC016953 | -3 | |
| AC024937 | -2 | |
| 6164848 | | LKAFTYINLDKAVLGTSNFKVSASPLLYTLIEKTMQNVKHPVTGQFLYQDSNWASKVEKLTLDNAAFPFLAYSGIPAVSFCFCEDTDYPYLGTTM |

FIG. 12B

| Accession | Frame | |
|---|---|---|
| AF187320 | +1 | DTYKELIERIPELNKVARAAAEVAGQFVIKLTHDVELNLDYERYNSQLLSFVRDLNQYRADIKVSTDSNYVFILLNVKYFEM |
| AF187320 | +3 | |
| AC016953 | -2 | DTYKELIERIPELNKVARAAAEVAGQFVIKLTHDVELNLDYERYNSQLLSFVRDLNQYRADIKVSTDSNYVFILLNVKYFEM |
| AC024937 | -3 | |
| 6164848 | -2 | DTYKELIERIPELNKVARAAAEVAGQFVIKLTHDVELNLDYERYNSQLLSFVRDLNQYRADIKEMGLSLQWLYSARGDFFRATSRLTTDFGNAEK |

| Accession | Frame | |
|---|---|---|
| AF187320 | +1 | |
| AF187320 | +3 | |
| AC016953 | -2 | |
| AC024937 | -3 | |
| 6164848 | -2 | TDRFVMKKLNDRVMRVEYHFLSPYVSPKESPFRHVFWGSGSHTLPALLENLKLRKQNNGAFNETLFRNQLALATWTIQGAANALSGDVWDIDNEF |

FIG. 12C

AUTOMATED IDENTIFICATION OF PEPTIDES

This application claims the benefit of UK Application No. 0022,136.6, filed Sep. 8, 2000, and U.S. Provisional Application No. 60/232,273, filed Sep. 13, 2000; the contents of each of the foregoing are incorporated by reference herein in their entirety.

1. INTRODUCTION

This invention relates to computer-mediated methods and apparatus for automated interpretation of data obtained by mass spectrometry of an experimental peptide in order to identify a corresponding sequence if present in a peptide sequence database.

2. BACKGROUND OF THE INVENTION

Characterisation of the complement of expressed proteins from a single genome is a central focus of the evolving field of proteomics. A proteome is the protein complement of a cell or tissue. Since one genome produces many proteomes (multi-cellular organisms can have hundreds of proteomes) and the number of expressed genes in a cell is generally considered to exceed 10,000, the characterisation of thousands of proteins to evaluate proteomes can best be accomplished using a high-throughput, automated process.

Certain methods for analyzing peptides using mass spectrometry are known in the art. Peptide molecular weights and the masses of sequencing ions can be obtained routinely to an accuracy which enables mass distinction amongst most of the 20 amino acids in the genetic code. In tandem mass spectrometry, a peptide sample is introduced into the mass spectrometer and is subjected to analysis in two mass analyzers (denoted as MS1 and MS2). In MS1, a narrow mass-to-charge window (typically 2–4 Da), centered around the m/z ratio of the peptide to be analyzed, is selected. The ions within the selected mass window are then subjected to fragmentation via collision-induced dissociation, which typically occurs in a collision cell by applying a voltage to the cell and introducing a gas to promote fragmentation. The process produces smaller peptide fragments derived from the precursor ion (termed the 'product' or 'daughter' ions). The product ions, in addition to any remaining intact precursor ions, are then passed through to a second mass spectrometer (MS2) and detected to produce a fragmentation or tandem (MS/MS) spectrum. The MS/MS spectrum records the m/z values and the instrument-dependent detector response for all ions exiting from the collision cell. Fragmentation across the chemical bonds of the peptide backbone produces ions that are either charged on the C-terminal fragment (designated as x, y or z ions) or on the N-terminal fragment (a, b or c ions). Peptides are fragmented using two general approaches, high and low energy collision-induced dissociation (CID) conditions. In low energy CID experiments, signals assigned to y and b ions and from losses of water and ammonia are usually the most intense. During high energy CID, peptide molecules with sufficient internal energy to cause cleavages of the amino acid side chains are produced. These side chain losses predominantly occur at the amino acid residue where the backbone cleavage occurs. The general designations for these ions are d for N-terminal and w for C-terminal charged fragments, respectively. Other useful sequencing ions occur which result from a y-type cleavage at one residue and a b type cleavage at another residue along the polypeptide backbone (internal fragment ions) (Biemann, K. (1990) Sequencing of peptides by tandem mass spectrometry and high-energy collision-induced dissociation. Methods Enzymol. 193, 455–479; Biemann, K. (1990) Sequencing of peptides by tandem mass spectrometry and high-energy collision-induced dissociation. Methods Enzymol. 193, 455–479; Biemann, K. (1990) Sequencing of peptides by tandem mass spectrometry and high-energy collision-induced dissociation. Methods Enzymol. 193, 455–479; Papayannopoulos, I. A. (1995) Mass Spectrometry Reviews 14, 49–73)

Previous studies have attempted to determine chemical structures of unknown peptides using fragmentation spectra. Most often these studies have involved manual interpretation using prior knowledge derived from fragmentation spectra of known peptides. It is well recognized from these studies that multiple sequence interpretations are possible from the same fragmentation spectrum. The lack of a unique result is a major impediment to the development of accurate, high throughput methods for sequencing unknown peptides using tandem mass spectrometry.

Various computer-mediated methods have been attempted for deducing the sequence of a peptide from an MS/MS spectrum. In one approach, 'sub-sequencing' strategies are used whereby portions of the total sequence, (i.e., sub-sequences) are tested against the mass spectrum. (Ishikawa et al. (1986) Biomed. Environ. Mass Spectrom. 13, 373–380; Siegel et al. (1988) Biomed. Environ. Mass Spectrom. 15, 333–343; Johnson et al. (1989) Biomed. Environ. Mass Spectrom. 18, 945–957), which are hereby incorporated by reference in their entirety). In this approach, sub-sequences that read or correlate to ions observed in the MS/MS spectrum are extended by a residue and the whole process is then repeated until the entire sequence is obtained. During each incremental extension of the sequence, the possibilities are reduced by comparing sub-sequences with the mass spectrum and only permitting continuation of the process for sub-sequences giving the most favorable spectral matches. Determination of amino acid composition has also been utilised to limit sequence possibilities. (Zidarov et al. (1990) Biomed, Environ. Mass Spectrom. 19(1), 13–26, the contents of which is hereby incorporated by reference in its entirety).

An alternative approach has been to develop programs for de novo peptide sequencing from fragmentation spectra based on graph theory. (Fernandez-de-Cossjo, J. et al., (1995) CABIOS 11, 427–434; Hines, A. et al. (1995) J. Am. Soc. Mass Spectrom. 3, 326–336; Knapp, J. Am. Soc. Mass Spectrom. 6, 947–961, which are hereby incorporated by reference in their entirety). The basic method involves mathematically transforming an MS/MS spectrum into a form where fragment ions are converted to a single fragment ion type represented by a vertex on the spectrum graph. (Bartels, (1990) Biomed. Environ. Mass Spectrom. 19, 363–368, the contents of which is hereby incorporated by reference in its entirety). Peptide sequences are then determined by finding the longest series of these transformed ions with mass differences corresponding to the mass of an amino acid.

Yet other methods attempt to match spectral information with sequences in protein and translated nucleotide sequence databases. An algorithm has been described for searching protein and nucleotide databases with mass and sequence information from fragmentation spectra of tryptic peptides (MS-TAG) (Mann and Wilm (1994) Anal Chem. 66, 4390; Clauser, P. Baker and A. L. Burlingame, in Proceedings of the 44th ASMS Conference of Mass Spectrometry and Allied Topics. Portland, Oreg., 1996, pp. 365–366, which are hereby incorporated by reference in their entirety). These prior art algorithms require manual spectral interpretation and also suffer from well-recognized problems of inaccurate sequence determination. (Perkins et al. (1999) Electrophoresis 20, 3551–3567), which is hereby incorporated by reference in its entirety). In an effort to mitigate these shortcomings, Mann and his colleagues have used comparison with the fragmentation spectra of the same peptide after methylation of the carboxyl groups or enzymatic digestion in the presence of $^{18}O$ water to incorporate $^{18}O$ into the C-terminal carboxy groups (Shevchenko et al. (1997) J. of Protein Chemistry 16(5):481–90 and Shevchenko, A. (1997) Rapid Commun. In Mass Spectr. 11(9), 1015–1024, which are hereby incorporated by reference in its entirety). A similar approach has been extended to the analysis of intact proteins using laser fragmentation and Fourier-transform mass spectrometry. (Mortz, E. et al. (1996) PNAS 93, 8264, which is hereby incorporated by reference in its entirety).

A different approach has been described for identifying peptide sequences from database interrogation by comparing the experimental fragmentation spectrum with theoretical spectra from a mass-constrained set of database sequences (SEQUEST). (Yates III et al. U.S. Pat. No. 5,538,897; Yates III, P. R. Griffin and L. E. Hood, in Techniques in Protein Chemistry, edited by J. J. Villafranca, Vol. 2, Academic Press, San Diego pp. 477–485 (1991), which are hereby incorporated by reference in their entirety). For each candidate sequence within the database spectrum, a theoretical fragmentation spectrum is formed according to a selected ion model of peptide fragmentation. The predicted theoretically derived mass spectra are compared to each of the experimentally derived fragmentation spectra by a cross-correlation function for scoring spectra.

Prior art methods for automated analysis of fragmentation mass spectra are capable of generating a ranked list of candidate peptide sequences in a sequence database; however, identification of a true match from amongst multiple candidate sequences has heretofore required subjective manual assessment by one skilled in spectral interpretation.

3. SUMMARY OF THE INVENTION

The present invention provides a user-independent method to identify and characterize a peptide sequence present in a peptide database that corresponds to an experimental peptide, for example a peptide derived by selective cleavage of a polypeptide, by automated, computer-mediated interpretation of data obtained by mass spectrometry of the experimental peptide. By applying previously ordained criteria, the present method identifies the corresponding sequence if it is present in the database (or the corresponding sequences, if duplicates are present in the database), without the need for a skilled observer to choose from amongst a list or ranked list of possible matches by reference to mass spectrometric or other criteria. The methods can be performed with large peptide databases, including those prepared by conceptual translation of large nucleotide databases such as a database representing a eukaryotic (e.g. mammalian or higher plant) genome such as the human genome or maize genome.

In a preferred embodiment, a computer-mediated program (or set of programs) performs the method described herein without the intervention of a person skilled in spectral interpretation, and preferably without the intervention of an operator. The capacity for fully automated analysis of mass spectral information and searching of a peptide sequence database, coupled with computer-mediated mapping of related nucleotide or peptide databases, permits the high-throughput identification and organization of expressed segments of DNA in large polycistronic genomic databases and the rapid identification of nucleotide or peptide sequencing errors and polymorphisms.

The methods described herein provide the ability to sequence and/or identify peptides without any derivatization or labeling, for instance without preparing isotopically labeled peptides such as $^{18}O$ labeled peptides. By virtue of the back-read process described herein, the present method can uniquely identify a corresponding peptide sequence in a peptide database based on identifying a single peptide sequence that is shared between the experimental peptide and the corresponding peptide in the database. This obviates the need to interpret multiple fragmentation mass spectra or to find multiple hits in order to identify the corresponding peptide in the database.

The present invention further provides methods for mapping mass spectral data to sequences in peptide or nucleotide databases for (1) unambiguous identification of exons within nucleotide sequences; (2) determining a correct reading frame of a nucleotide sequence; (3) identifying artefacts and errors in nucleotide or peptide sequences; (4) identifying mutations and polymorphisms in nucleotide sequences, as well as peptide polymorphisms; (5) identifying post-translational modifications of peptides; and (6) identifying exon-intron boundaries in genomic databases.

The invention further provides a computer-readable medium comprising instructions for causing a computer to perform any of the methods disclosed herein; a computer comprising instructions for performing any of the method disclosed herein; a peptide or nucleic acid database comprising information obtained by performing any of the methods disclosed herein; a computer-readable file or list comprising information obtained by performing any of the methods disclosed herein; and a display comprising information obtained by performing any of the methods disclosed herein.

In a further embodiment, the present invention provides a computer-mediated method for determining whether or not a fragmentation mass spectrum (or a defined segment thereof) contains peaks defining a member of a set of peptides to be recognized, comprising generating a set of signature arrays collectively representing the spectral signatures of the peptides to be recognized; generating a spectral array representing a plurality of peaks detected in the fragmentation mass spectrum; and performing a series of logical AND comparisons between the display array and each signature array while the latter is swept across a portion of the array representing the segment of the spectrum to be inspected. This method has general applicability to interpretation of fragmentation mass spectra.

4. BRIEF DESCRIPTION OF THE FIGURES

FIG. 1 shows an embodiment of the present invention for identifying and characterizing genomic sequences that are expressed as peptides.

FIG. 2 details an embodiment of an algorithm for constructing and editing the peak table derived from the fragmentation mass spectrum.

Figure 7:
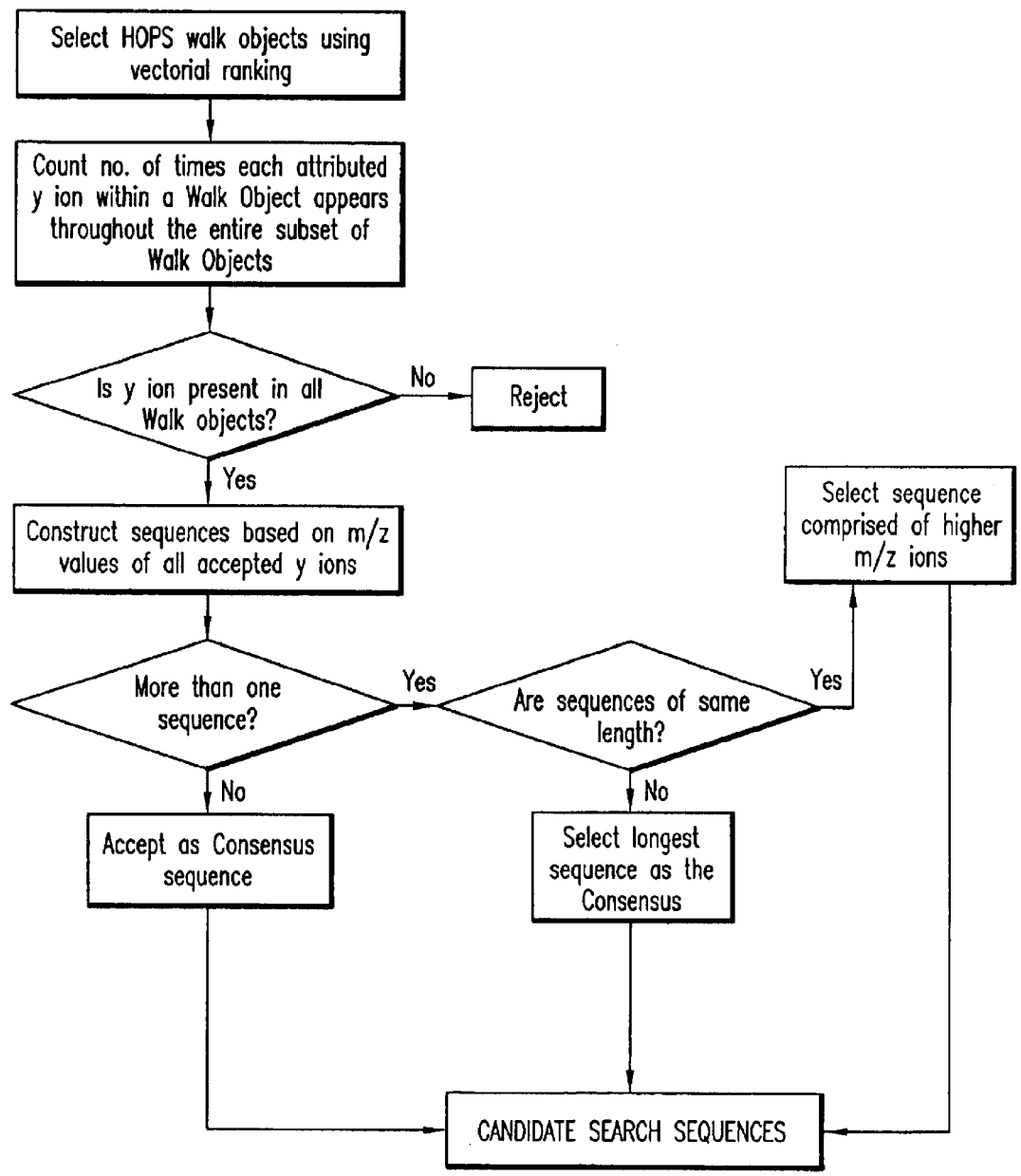

FIG. 7 details one embodiment of the steps for selecting HOPS sequences to construct a database search string.

Figure 8:
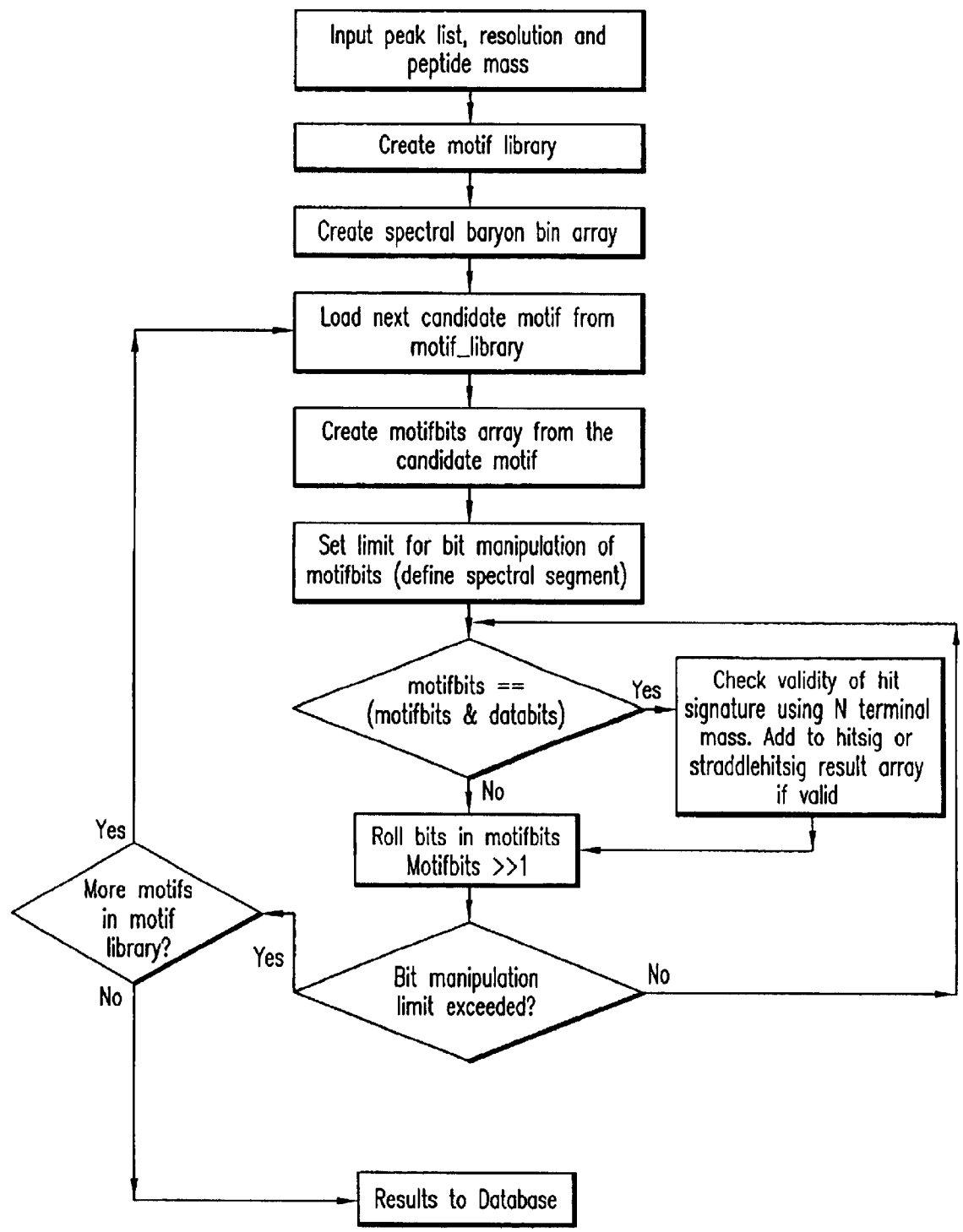
Figure 9:
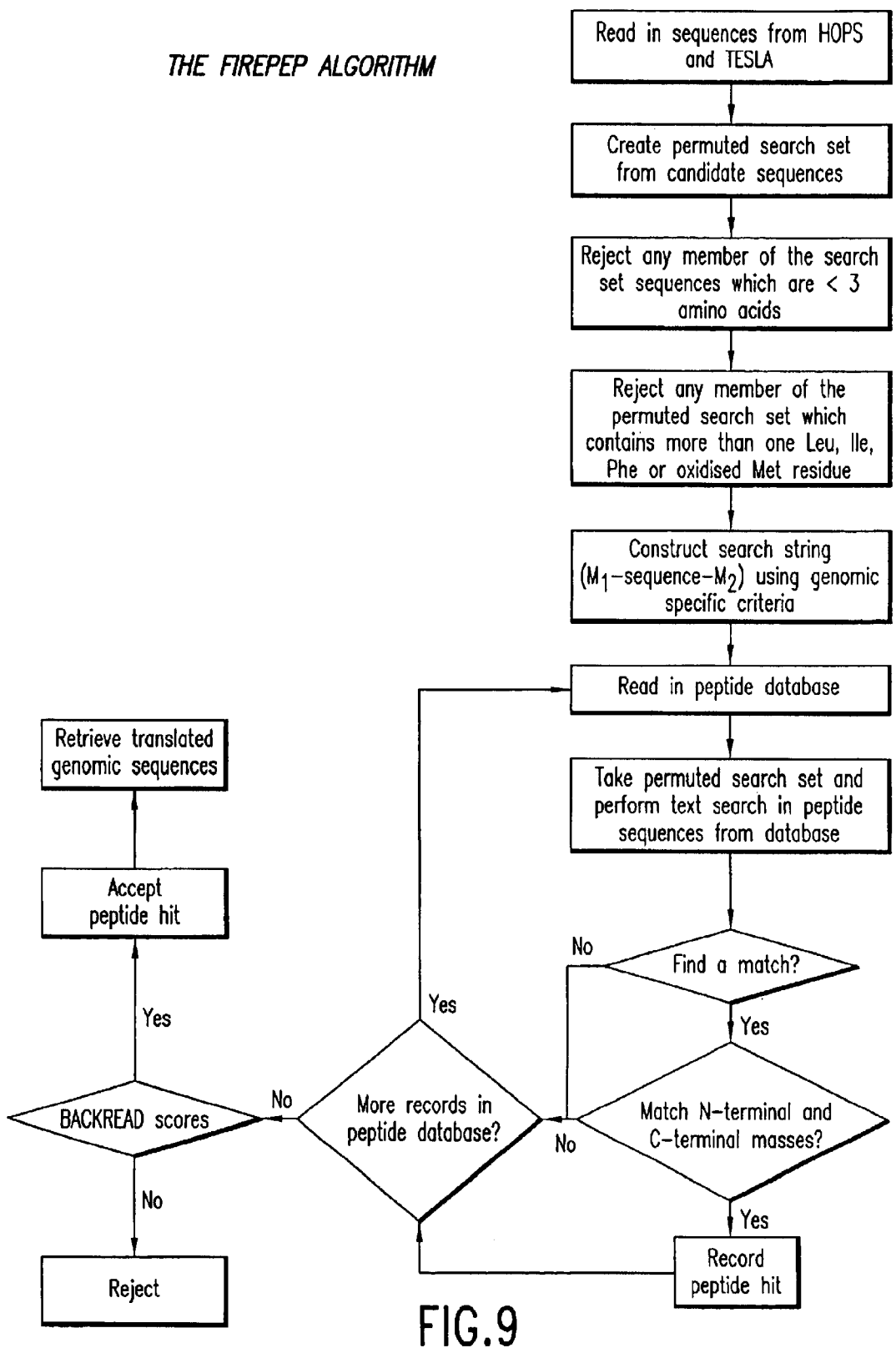

FIG. 8 shows the TESLA algorithm (Trimer Signature Lookup Algorithm) which interprets fragmentation spectra to identify trimer peptide sequences according to a preferred embodiment of the invention FIG. 9 shows a preferred embodiment of the FIREPEP algorithm (Find Related Peptides) for constructing database M1-trimer-M2 search strings and for searching an in silico tryptic digest with the database-specific search string.

FIG. 10 (SEQ ID NO.: 7) details a preferred embodiment of the rules for constructing a search string and preferred criteria of the retrieved sequences from the six-frame translated human genome.

Figure 11:
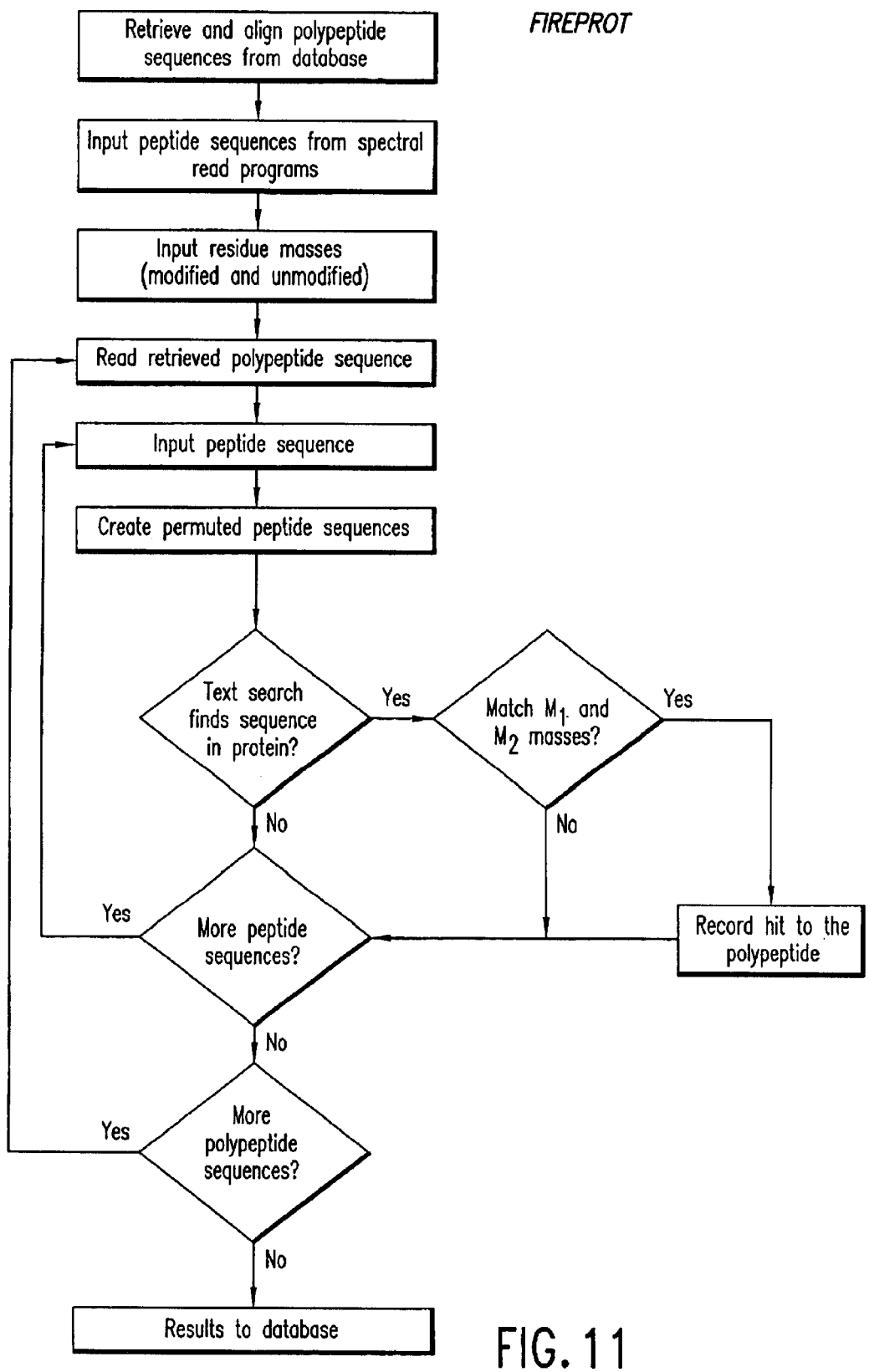

FIG. 11 shows an embodiment of the FIREPROT (Find Related Protein) algorithm which maps the mass spectrometric sequence data onto retrieved peptide or translated nucleotide sequences that have been retrieved by searching with a search string.

FIG. 12 (SEQ ID NO.: 1, SEQ ID NO.: 2, SEQ ID NO.: 3, SEQ ID NO.: 4, SEQ ID NO.: 5, SEQ ID NO.: 6) shows the mapping of observed masses and sequences onto conceptually translated genome sequences, in which the box delineates a tryptic peptide matched by FIREPEP to an experimental peptide, the underlined sequences were mass matched using peptide molecular weights, the bolded sequences were identified by spectral read, and the arrowheads delineate a sequence matched by the mapping algorithm of FIREPROT.

Figure 13:
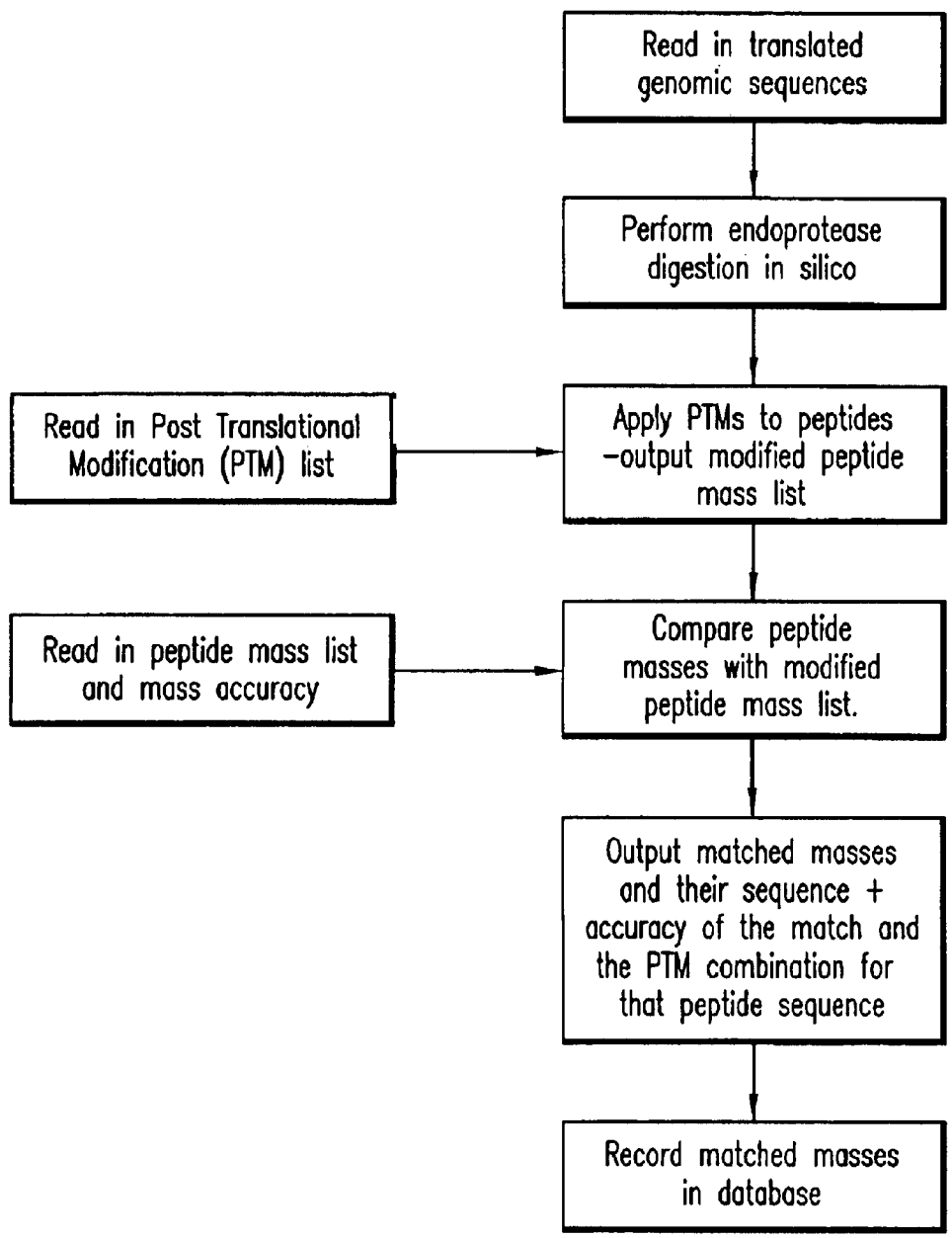

FIG. 13 shows an algorithm for mapping observed peptide masses and post-translational modifications onto the unique set of identified translated genome sequences.

5. DETAILED DESCRIPTION OF THE INVENTION 5.1 Definitions

As used herein "amino acid residue" means a monomer of the general structure: —NH—CHR—CO— which makes up peptides, oligopeptides and polypeptides. These include the twenty basic amino acids and common derivatives listed in Table 1, and chemically or biologically modified monomers having the same general structure.

As used herein "conceptually translated peptide sequence" means a listing of a peptide sequence predicted to be encoded by a given nucleotide sequence in accordance with the universal genetic code. Preferably, the conceptually translated peptide sequence is in machine-readable form.

As used herein "consensus sequence" means a subsequence that is shared among multiple peptide sequences deduced by interpreting a fragmentation mass spectrum of a peptide.

As used herein, a "display" means any device or artefact that presents information in a form intelligible to a human observer and includes, without limitation, a computer terminal, a computer screen, a screen upon which information is projected, and paper or other tangible medium upon which information is temporarily or permanently recorded, whether by printing, writing or any other means.

As used herein, a peptide sequence in a database "corresponds to" an experimental peptide when it correctly specifies the identity and order of the amino acid residues in the experimental peptide except only for substitution of amino acids that are mutually isobaric or mutually mass ambiguous within the resolution of the mass spectrometer used to identify the peptide sequence. A peptide sequence in a database that corresponds to an experimental peptide is referred to herein as a "corresponding" sequence.

As used herein a "database" of peptide (or nucleotide) sequences means a computer-readable representation of a plurality of peptide (or nucleotide) sequences. A database may be implemented as one or more computer-readable files.

As used herein, an "experimental peptide" is a peptide that is to be identified by the present invention or that is sought to be matched with one or more peptide sequences in a database.

As used herein, "in silico digestion" of a peptide means use of a computer-mediated algorithm to generate a list representing peptides that would result from selective cleavage (e.g. by digestion with a proteolytic enzyme such as trypsin) of the peptide. In silico digestion may be applied to a single peptide, a plurality of peptides represented in a database, or all the peptides represented in a database.

As used herein, "list" means a computer-readable representation of data; a list may be implemented as any desired data structure, including without limitation a table, stack or array. A list may if desired be stored as a file or as a plurality of files.

As used herein, "parent ion" (also known as a "precursor ion") means an ionized peptide (e.g. an ionized form of an experimental peptide) that is fragmented into a plurality of "product ions" (also known as "daughter ions"). A fragmentation mass spectrum can be produced by recording the mass-to-charge (m/z) ratios and intensities of the product ions.

As used herein "peptide" means an organic compound comprising two or more amino acid residues joined covalently by one or more peptide bonds; a peptide may be glycosylated or unglycosylated. A peptide containing ten or fewer amino acid residues is an "oligopeptide" and a peptide containing more than ten amino acid residues is a "polypeptide".

As used herein "post-translational modification" means a chemical or biological modification to an amino acid residue after its insertion into a peptide chain. This may occur naturally or in the laboratory.

As used herein "publicly available database" means a database that is available in the public domain. Examples of publicly available databases include, but are not limited to, the European Molecular Biology Laboratory (EMBL) human genome database, the National Center for Biotechnology Information (NCBI) peptide database (http://www.ncbi.nlm.nih.gov) and the Swiss Institute of Bioinformatics (SIB), SWISSPROT protein database.

5.2 Preparing a Fragmentation Mass Spectrum from the Experimental Peptide

In order to practice the present invention, one or more mass spectra are obtained from a peptide (the "experimental peptide") that is to be identified or matched to a peptide sequence in a database.

In one embodiment, the experimental peptide is obtained by selective cleavage of a mixture of polypeptides, for example a mixture containing no more than 50 (preferably no more than 20, more preferably no more than 10, still more preferably no more than 5) polypeptides; alternatively, the experimental peptide is obtained by selective cleavage of a polypeptide that has been isolated free from other polypeptides. Enzymatic cleavage is suitable for this purpose; suitable enzymes include arginine endopeptidase (ArgC), asparatic acid endopeptidase N (aspN), chymotrypsin, glutamic acid endopeptidase C (gluC), lysine endopeptidase C (lysC), V8 endopeptidase and (more preferably) trypsin. Other enzymes with sufficiently restrictive cleavage patterns may also be used and are known in the art. Non-enzymatic selective cleavage is also suitable, for example use of cyanogen bromide to cleave a polypeptide at the C-terminal side of Met residues.

In one embodiment, one or more fragmentation mass spectra are obtained from the experimental peptide, alternatively, ladder sequencing may be used to obtain one or more mass spectra as described in U.S. Pat. No. 6,271,037, which is incorporated herein by reference. Processes that produce fragmentation useful for generating a fragmentation mass spectrum, include but are not limited to, collision-induced dissociation (also known as collision-activated dissociation), post-source decay from laser desorption, surface-induced dissociation, and in-source fragmentation. Ionisation processes which can be used include, without limitation, electrospray ionisation, nanoflow electrospray ionisation, matrix-assisted laser desorption ionisation, plasma desorption ionisation, fast atom bombardment, and field desorption. A mass spectrum can be generated using tandem mass spectrometry or multiple stages of mass spectrometry. In one preferred embodiment, a mass spectrum is obtained by linear tandem mass spectrometry, for example using a tandem time-of-flight (TOF-TOF) mass spectrometer. Alternatively, a mass spectrum is obtained by orthogonal mass spectrometry, for example using a quadrupole tandem time of flight (Q-TOF) or Q-STAR mass spectrometer. Other instrument types and configurations can be used, provided they result in a sufficient number of the required suite of sequencing ions to generate sequence information. These include, without limitation, tandem magnetic sector instruments, fourier-transform ion cyclotron resonance mass spectrometers, and quadrupole ion trap mass spectrometers. In a preferred embodiment, a first aliquot of a preparation containing one or more peptides is analyzed with a matrix-assisted laser-desorption ionization mass spectrometer (MALDI-TOF) to determine the mass of one or more peptides; a second aliquot of the preparation is then analyzed with a hybrid mass spectrometer (e.g. a Q-TOF or Q-STAR mass spectrometer) in which a quadrupole mass analyser is used as a first "mass filter" and a time-of-flight (TOF) mass analyser is used to separate the fragmentation ions in a post-collision cell.

Figure 1:
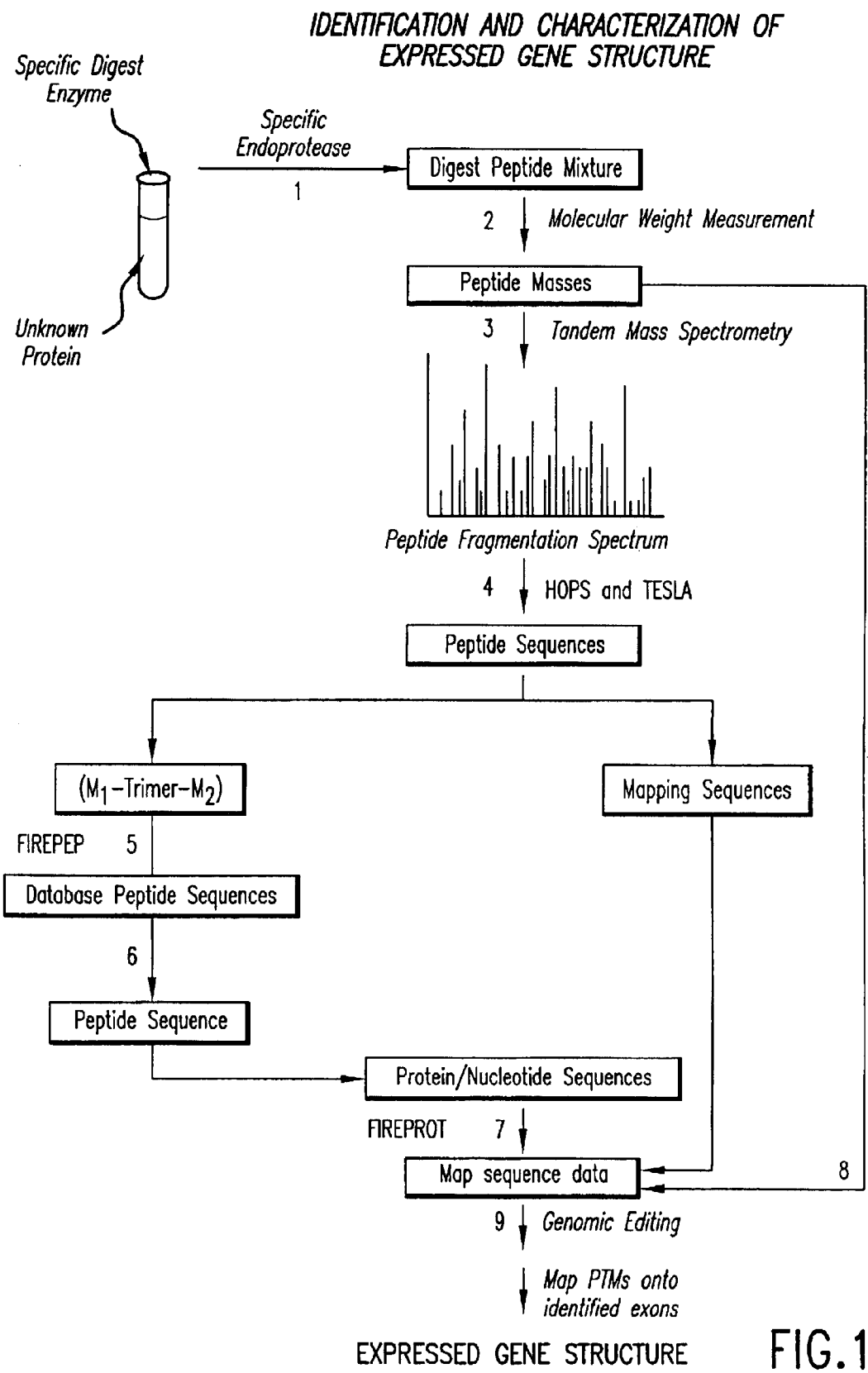

FIG. 1 shows an overview of a preferred embodiment of the invention for identification of a polypeptide (e.g. an unknown protein) and its further use for characterization of expressed genomic sequences including their post-translational modifications. The polypeptide is first digested with a specific endoprotease such as trypsin, to cleave the polypeptide into one or more peptide fragments.

In a preferred embodiment, the polypeptide has been isolated from a polyacrylamide (or other) gel following one-dimensional or two-dimensional electrophoresis; a software-driven robotic cutter is useful for this purpose, as described in U.S. Pat. No. 6,064,754, which is incorporated herein by reference. The gel pieces are preferably subjected to in situ proteolysis, for instance using an OGS ChemStation robot and a modification of the manual method described in Page et al., Proc. Natl. Acad. Sci. 96: 12589–12594 (1999), which is incorporated herein by reference. In a preferred embodiment, digestion of the polypeptide is carried out with trypsin under conditions chosen to achieve thorough trypsinolysis, so as to maximise the number of peptide fragments that contain C-terminal Arginine or Lysine residues.

In a preferred method for in situ proteolysis, one or more robotically cut gel plugs are washed by adding 50 µl of 100 mM ammonium bicarbonate to each sample. After standing for 10 minutes at ambient temperature, the liquid is removed and acetonitrile (50 µl) is added to each tube. The samples are allowed to stand for 10 minutes at ambient temperature and are manually agitated for 5 minutes, then dried by centrifugal evaporation for 10 minutes with no heating. Acetonitrile (50 µl) is again added to each tube, the samples allowed to stand for 10 minutes at ambient temperature and then manually agitated for 5 minutes, followed by drying by centrifugal evaporation for 10 minutes with no heating. Next 50 µL of 100 mM ammonium bicarbonate are added to each tube. Porcine trypsin (133 ng in 5 µL) (Promega, Madison, Wis.) is added to each sample. After 5 minutes at room temperature, additional trypsin (66.5 ng in 5 µL) is added to each sample. The samples are incubated at 40° C. for 2 hr in an oven and after cooling at room temperature for 5 minutes are centrifuged for 1 minute at 13,000 rpm in a MicroCentaur centrifuge (Sanyo, Cat. no. 193-800). The liquid (peptide pool) surrounding the gel piece is removed and dispensed into clean 0.5 ml test tubes for mass spectrometric analysis.

Trypsin cleaves specifically at the carboxyl side of lysine (Lys) and arginine (Arg) residues, so that the resulting tryptic digest fragments should have a Lys or Arg as the C-terminal amino acid, unless the peptide fragment was obtained from the C-terminal end of the peptide. Similarly, the amino acid in the intact polypeptide that, prior to cleavage, directly preceded the N-terminal amino acid of the peptide fragment should also be a Lys or Arg, unless the peptide fragment was obtained from the N-terminal of the peptide.

The mixture of peptide fragments (experimental peptides) obtained from digestion of individual polypeptides (or mixtures of polypeptides) can be analysed by mass spectrometry without any prior separation (as shown in FIG. 1, step 2) or can optionally be separated into individual experimental peptides using known chromatographic methods. In a preferred embodiment, the experimental peptides are initially analysed using matrix-assisted laser-desorption time-of-flight mass spectrometry with delayed extraction and a reflectron in the time-of-flight chamber (MALDI-TOF). This instrument configuration is used to generate a primary mass spectrum in order to determine the molecular weight of the experimental peptide, preferably with an experimental error of 100 parts-per-million (ppm) or less. Accurate measurement of peptide masses in the primary mass spectrum advantageously increases the specificity of the mass-constrained database searches used in subsequent steps of a preferred embodiment of the present invention. (See, e.g., FIG. 1, step 5). Other mass spectrometric techniques capable of mass measurement within an error of 100 ppm or less include, without limitation, time-of-flight, Fourier transform ion cyclotron resonance, quadrupole, ion trap, and magnetic sector mass spectrometry and compatible combinations thereof.

In order to determine a peptide sequence within the experimental peptide, it is then analysed by mass spectrometry, preferably by tandem mass spectrometry, to obtain a fragmentation spectrum for the corresponding parent ion. (FIG. 1, step 3). Preferably, the fragmentation mass spectrum is obtained for a parent ion having m/z greater than or equal to 850, e.g. as determined in a primary mass spectrum. In a preferred embodiment a resolution of better than 4000 (peak width at half maximum height) and an accuracy of mass measurement of at least 50 ppm (partsper-million) is used. Tandem mass spectrometry may be carried out on a doubly protonated parent ion ($[M+2H]^{+2}$), although the method can be performed on parent ions of other charge states, e.g., $[M+H]^+$ or $[M+3H]^{+3}$.

In one preferred embodiment, a Q-TOF mass spectrometer is used with the quadrupole mass analyser set to allow transmission of ions with an m/z equal to that of the doubly protonated peptide ion ($[M+2H]^{+2}$) deduced from the singly charged peptide ion ($[M+H]^+$) observed in a primary mass spectrum obtained by MALDI-TOF analysis. The transmitted ions are termed 'parent' or 'precursor' ions. The peptide ion beam passes into the collision cell where the parent ions are subjected to low energy CID. This can be achieved through the application of a voltage on the collision cell and/or by the introduction of an inert gas. The resulting fragment ions (termed the 'product' or 'daughter' ions) and any intact parent ions are then transmitted into the TOF mass analyser. The predominant ion series results from cleavage across the peptide backbone, and gives rise to a, b and y ions. In another preferred embodiment employing a TOF-TOF mass spectrometer, the timed ion selector is preferably set to capture ions in a high energy collision cell at m/z equal to that of the singly charged peptide ion ($[M+H]^+$). In this case, fragmentation occurs both across the peptide backbone, giving rise to N-terminally charged ions (a, b and c ions) and C-terminally charged ions (x, y and z ions), and also across the side chains, giving rise to d and w ions. Fragmentation (MS/MS) spectra are typically represented by a two-dimensional graph with ion intensity on the y-axis, and mass-to-charge ratio (m/z) on the x-axis.

5.3 Generating a First Peak List

One or more fragmentation spectra are subjected to computer-mediated analysis to identify one or more peaks and prepare a first peak list. Techniques for computerized recognition of peaks are known in the art and include pattern recognition and linear interpolation. Sukharev, Y. N. and Nekrasov, Y. S. (1976) The computer processing and interpretation of mass spectral information. Organ. Mass Spect. 11, 1232–1238; Klimowski, R. J. et al., (1970) A small on-line computer system for high resolution mass spectrometers. Org. Mass Spect. 4, 17–39, which are incorporated by reference).

In a preferred embodiment, a mass spectrum is acquired as an array of numerical values representing m/z and signal intensity (the "raw spectrum"). Signals arising from sources other than the analyte(s) of interest are well documented. These include electronic disturbance (electronic noise) and signals from the sample matrix (chemical noise). Methods for converting raw spectral data, represented as a series of peaks within x,y coordinates, into a subset of m/z and intensity values useful for implementing computer-mediated spectral interpretation have been described for a variety of mass spectrometers and sample types. The successful implementation of an algorithm to deduce peptide sequences from fragmentation spectra of varying quality depends on the methodology which optimizes the choice of peaks from the raw mass spectrum. Preferably, only peaks having a signal to noise ratio >2 are considered.

In one embodiment, using a Q-TOF mass spectrometer (Micromass UK Ltd.), an intensity threshold is applied to the raw spectrum and values with intensity <2 are removed; a median filter is applied to the intensity values using at least 3 points to identify a peak (i.e. a smoothing function is used). In another embodiment, using a TOF-TOF mass spectrometer (ABI, Framingham, Mass.), an intensity threshold is calculated which excludes a defined fraction (say 80%) of the data points in the spectrum; peak picking from the data in the spectrum is then performed for data points that lie above this intensity threshold. Median values are assigned for the m/z of each peak, using a peak top method. (Philip R. Bevington. (1969) Data Reduction and Error Analysis for the Physical Sciences, McGraw Hill, N.Y., which is incorporated by reference).

In one embodiment, the list of median peak values is edited by one or more of the following computer-mediated procedures. First, the list can be computer read to identify two or three median peak m/z values that differ by 1 Dalton (atomic mass unit). Where such a cluster is found, the lowest m/z value is retained and the one or two higher m/z values (which are taken to arise from isotopic peptides containing one or two $^{13}C$ atoms) are removed. Second, for spectra obtained from an $[M+2H]^{2+}$ precursor ion, m/z values falling within a window from 1 Dalton below to 0.5 Dalton above the precursor ion are removed.

Once the m/z peaks have been identified, the fragmentation mass spectrum is analyzed to assign a mass value for each peak. In one embodiment, the charge (z) of the product ion is determined by analyzing the fragmentation spectrum (e.g., by determining the m/z separation of the paired $^{12}C$ and $^{13}C$ isotopic variants for that peak); once the charge (z) is known, the mass (m) can be readily determined from the measured mass-to-charge (m/z) ratio. In a preferred embodiment, each peak is treated as singly protonated (i.e., as though z=1) and the measured mass-to-charge (m/z) ratio is used as the assigned mass value for the peak. When this simplifying assumption is made, it is customary to use the term mass-to-charge (m/z) even when actually referring to the mass inferred from that value and used as the assigned mass value. This custom is followed herein, and one of ordinary skill in the art of mass spectrometry will know from the context whether a particular usage of m/z refers to a mass-to-charge ratio or to the mass of a peak inferred from the mass-to-charge ratio by treating the product ion as though it is singly charged.

In one embodiment of the invention, the fragmentation mass spectrum is represented as a data file comprising a list of m/z values of a plurality of peaks identified in the spectrum. These may be arranged in any desired order (e.g., ascending or descending order of m/z values). Preferably, the data file also contains the intensities of the peaks for which m/z values are listed, as well as sufficient information to determine the mass of the parent ion (e.g. the mass of the singly or doubly protonated precursor ion and charge state of the ion).

Figure 2:
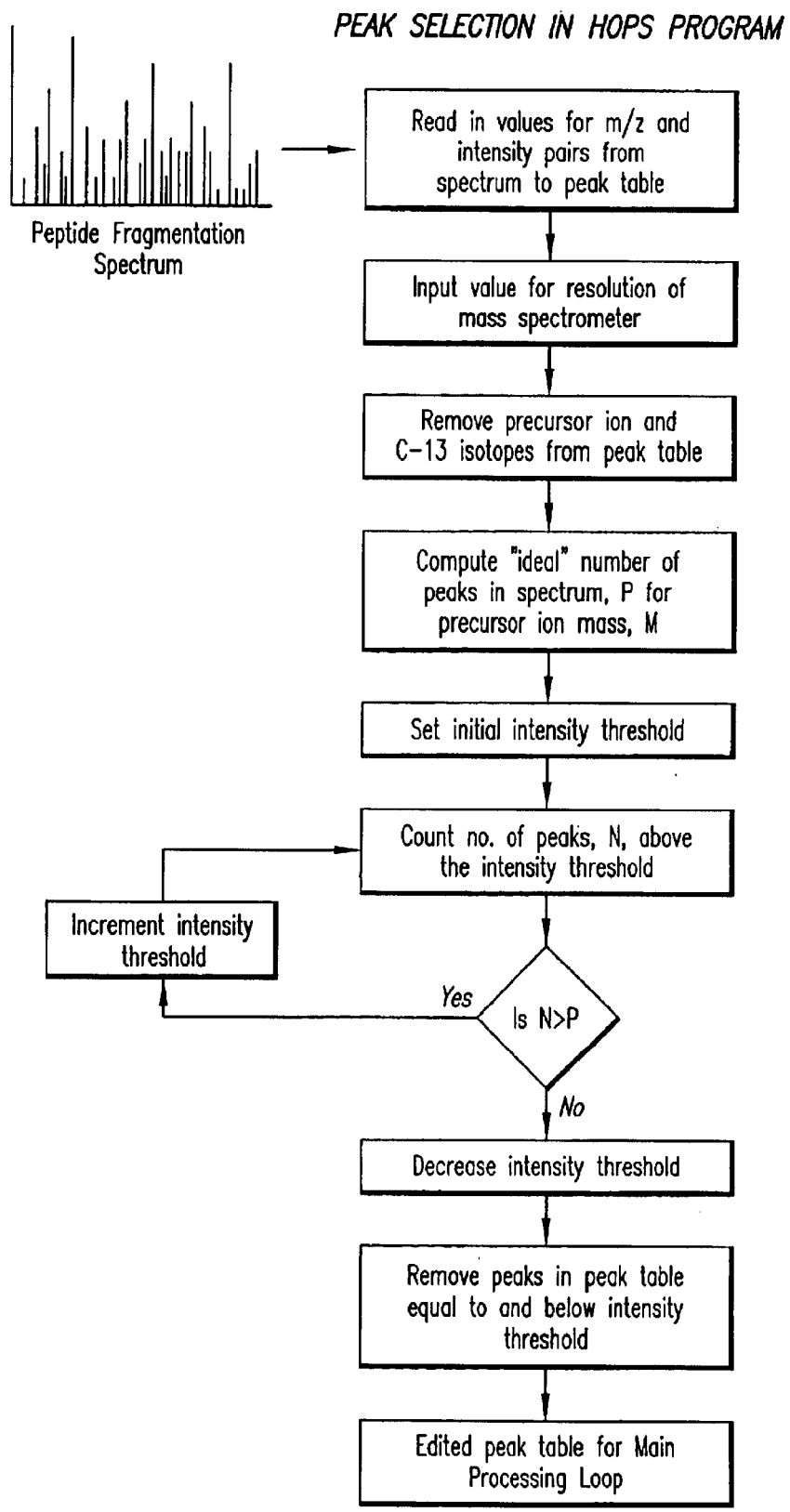

A preferred method for obtaining a peak table from the peptide fragmentation spectrum is shown in FIG. 2. The peak values extracted from the fragmentation mass spectrum (e.g. paired m/z and intensity values for peaks identified according to the 'peak-picking' algorithm described above) are subjected to filtering and/or editing to generate a peak table. This may be implemented by representing the raw extracted values in a Raw Peak Table, which is then subjected to computerized editing to generate an Edited Peak Table. Alternatively, the process of peak picking may be combined with a process of filtering in accordance with previously ordained criteria, circumventing the need for a Raw Peak Table. A preferred editing or filtering process may comprise one or more of the following functions in any desired combination and preferably includes any two or all three of these functions: (a) eliminating values due to $^{13}C$ isotopes ("deisotoping"), (b) removing a 2 Da parent ion window, and (c) removing peaks falling below a threshold value. An input value for the mass resolution of the mass spectrometer used to obtain the spectrum is also preferably obtained.

In a preferred embodiment, the Raw Peak Table is edited to eliminate certain peaks. First, deisotoping is performed by identifying clusters of two or three peaks that are spaced ~1 Da apart, where the peak with the lowest m/z value is interpreted as arising from ions containing the more commonly occurring $^{12}$C isotope, with the one or two peaks with higher m/z arising from rarer ions containing $^{13}$C. In an embodiment of the present method, only the lowest m/z peak in such a cluster is retained and the one or two higher m/z peaks in the cluster are eliminated from the peak table if those higher m/z peaks are of lower intensity than the lowest m/z peak in the cluster. Second, in spectra derived from doubly charged parent ions, the peak representing the parent ion is removed from the peak table. For a doubly charged precursor ion a window of m/z 0.5 below and 1.5 above the m/z of the precursor ion is calculated and peaks falling within this window are removed.

Third, an intensity thresholding function is performed in order to decrease the risk of spurious spectral interpretation and to speed the computational process. A preferred embodiment of the thresholding procedure is as follows: equation (6) is used to compute the integer "ideal" number of peaks (Pideal) which we would expect in a spectrum with a given precursor ion mass, M.

$$P_{Ideal} = 3 \times \left(\left(\frac{M}{100}\right) + 1\right) \quad (6)$$

The physical justification for using this equation is that we expect on average (M/100)+1 peaks due to the primary ion series (the y-ions), estimating the mean molecular weight of an amino acid residue at about 100 Da. Since three types of sequence ions are considered (y, b, and a ions) a multiplier of 3 is placed in equation (6). In reality more peaks will be present from other types of fragments (e.g., due to internal fragmentation of the peptide and decay of ions into additional alternative decay products). The initial intensity threshold is then set to any desired starting value, preferably to a desired signal to noise ratio or to the detector response or some multiple thereof. The thresholding algorithm then calculates the number of peaks that would remain in the spectrum if all peaks of intensity less than or equal to the set threshold are removed. If this number of peaks is greater than $P_{ideal}$, then the intensity threshold value is incremented by some arbitrary value and the calculation repeated. This procedure continues until the number of peaks remaining after application of the intensity threshold is less than or equal to the ideal number. This value is then decremented by one step. The purpose of this is to produce a spectrum which has a larger number of peaks than the "ideal" number, but where most of the low intensity peaks have been removed. This threshold level is then applied to the peaks in the peak table and those peaks with intensity less than or equal to the threshold value are excluded. Once this iterative thresholding procedure has been applied once (or several times) with a given mass spectrometer, the threshold value determined by iteration may be used for filtering or editing fragmentation mass spectra obtained from the same or a similar apparatus. Alternatively, a threshold value can be determined by calculation, by trial and error, by analysis of the relevant scientific literature, or chosen arbitrarily. Thus, the invention provides a process of filtering or editing that comprises removing one or more peaks having an intensity less than a previously established threshold value.

The result of this editing process is to remove one or more peaks so as to produce an Edited Peak List. Preferably, the editing process occurs in accordance with previously ordained criteria, without the intervention of a human operator. Alternatively, the fragmentation spectrum and/or peak table can be displayed to a human operator for interactive editing. The Edited Peak List is then subjected to further analysis in order to identify one or more candidate search strings.

5.4 Spectral Read Analysis to Deduce a Peptide Sequence Within the Experimental Peptide Analysis of the fragmentation spectrum is now performed by executing a computer-mediated sequencing algorithm (a "spectral read" algorithm) to deduce one or more peptide sequences within the experimental peptide. The deduced sequence(s) may be the complete sequence of the experimental peptide, but more typically may be one or more partial amino acid sequences within the experimental peptide. The spectral read analysis is preferably performed on a peak list, more preferably on an Edited Peak List or on a peak list that was produced by a process that comprises filtering to exclude one or more peaks, as described above. The deduced sequence(s) can then be used to construct search strings suitable for searching a database of peptide sequences.

As described in more detail below, the spectral read process comprises: (1) iteratively determining mass differences between peaks in the peak table that correspond to masses of amino acid residues recognized by the algorithm ("recognized amino acid residues") in order to deduce one or more peptide sequences within the parent ion; and (2) selecting one or more of the deduced peptide sequences for further analysis, e.g., for construction of a search sequence and/or for database mapping, as described herein. If this de novo analysis yields more than one deduced peptide sequence, the spectral read algorithm preferably performs a ranking process so as to prioritize the deduced peptide sequences according to previously ordained criteria, for example by producing a ranked list of deduced peptide sequences.

5.4.1 Deducing Peptide Sequences Within the Experimental Peptide

In order to deduce one or more peptide sequences, a computer-mediated algorithm operates on a peak list (preferably an Edited Peak List) by: (a) selecting a peak as a starting point and determining one or more mass differences in the peak list corresponding to the mass of a recognized amino acid residue; (b) sequentially determining each subsequent mass difference in the peak list that corresponds to the mass of a recognized amino acid residue; and (c) repeating the process of steps (a) and (b) for additional peaks so as to obtain a set of deduced sequences. In one embodiment, the peak selected as a starting point is a high mass peak, for example the peak having the highest mass in the peak table. The sequential determination of step (b) may be repeated until every mass difference between peaks has been investigated. Alternatively, the algorithm may establish a maximum length for the deduced peptide sequence by terminating the sequential determination process once a deduced peptide sequence contains a previously established number of amino acid residues. The maximum length for the deduced peptide sequence can be set at any desired value, such as 1, 2, 3, 4, 5, 6, 7, 8, 9 or 10 amino acid residues and so on, up to the number of amino acid residues in the parent ion. A maximum length of 3 is especially preferred, resulting in an algorithm that interprets the fragmentation mass spectrum to deduce tripeptide sequences.

If desired, the spectral read algorithm can consider peaks from the entire fragmentation mass spectrum. Alternatively, analysis can be confined to peaks found in one or more segments of the spectrum. This can be accomplished either by excluding peaks during the editing or filtering process that generates the peak list used for the spectral read, or by excluding peaks in the peak table from analysis during the spectral read. In one embodiment using a Q-TOF spectrometer, spectral read analysis is confined to peaks from that part of the spectrum representing m/z values greater than that of the doubly protonated precursor ion or includes only a predetermined number of peaks having an m/z value less than that of the doubly protonated precursor ion (e.g. the peak with the next-highest m/z value); this is preferred for analysis of a Q-TOF spectrum. With a TOF-TOF spectrometer, the spectral read algorithm preferably considers peaks with m/z from that of the molecular ion down to half that of the molecular ion, and/or peaks in a low m/z window (e.g., 300–500).

In one embodiment of the invention, the product ions used for determination of the amino acid sequence are contained in the y-ion series. Alternatively, a b-ion series or a combination of both y-ions and b-ions may be used. In a preferred embodiment, about five to about fifty product ions (more preferably about ten to about thirty product ions) are selected as peaks as starting points for the sequential determination of the amino acid mass residue difference.

Recognized amino acid residues may include residues of the twenty naturally occurring amino acids (or any desired subset of them) and preferably also include residues of amino acids altered during sample preparation and/or analysis (e.g. oxidized methionine and carbamidomethyl cysteine). Residues of amino acids altered by one or more natural or synthetic post translational modification (PTM) may also be included in the set of recognized amino acid residues. Such PTMs preferably include alkylation, phosphorylation, sulfation, oxidation or reduction, ADP-ribosylation, hydroxylation, glycosylation, glucosylphosphatidylinositol addition, ubiquitination, and artificial modification (e.g. biotinylation, cross-linking, and photoaffinity labeling). This is readily achieved by including the modified amino acid residues in the set of masses that are considered in determining whether a mass difference between two peaks corresponds to the mass of a recognized amino acid residue.

The recognition process may be implemented by means of a table representing the identity and masses of recognized amino acid residues; in a preferred embodiment, the monoisotopic masses are used for this purpose. See, e.g., Table 1. In a preferred embodiment, amino acid masses are specified up to 5 decimal places; any experimental uncertainty in their mass is then negligible compared to the uncertainty in the experimentally obtained m/z values. As the measured m/z values of product ion peaks are subject to experimental error derived from the mass resolution of the mass spectrometer, minimum and maximum values need to be computed for the m/z differences in observed in the fragmentation spectrum. If the mass of an amino acid residue agrees (within experimental error) with the mass difference between two peaks, then there is deemed to be a correspondence between the experimentally observed inter-peak interval and the mass of that amino acid residue.

In a particular embodiment of the invention, the experimental uncertainty is assumed to result in a normal statistical distribution. The given m/z value from the peak table is then deemed to be the mean value for the peak, and the experimental error of the instrument is deemed to be equal to the standard deviation from the mean. The experimental uncertainty is then assigned as being ±2 standard deviations from the mean value, i.e. the 95% confidence limit of the normal distribution.

Thus, in order to determine whether the difference between two particular m/z values corresponds to the mass of an amino acid group, a mass range that incorporates the uncertainties in both m/z values is calculated which is dependent on the mass resolution of the type of instrument used. In a preferred embodiment the minimum instrument resolution desired for interpretation of peptide fragmentation spectra may be determined by the following calculation. For the mass spectrometer used (for example, a Q-TOF instrument), each peak has a finite width and this width acts as the error for an individual peak. This error is compounded for the difference in m/z values of two peaks. For two peaks we calculate the compound error $\Delta E$ from the components E1 and E2 due to the two peaks:

$$\Delta E = \sqrt{(E_1^2 + E_2^2)} \quad (1)$$

To a first approximation, we assume that the width of each peak is the same:

$$\Delta E = \sqrt{2E^2} \quad (2)$$

To obtain an unambiguous determination of the correct amino acid residue, the compound error on the difference between the two peaks must be less than 1 Dalton. Therefore for a correct read:

$$\sqrt{2E^2} < 1 \quad (3)$$

We can write the error, E, at mass, M, in terms of the mass resolution of the mass spectrometer, R:

$$E = \frac{M}{R} \quad (4)$$

and so condition (3) becomes $$M < \frac{R}{\sqrt{2}} \quad (5)$$

Therefore, in this embodiment, as long as condition (5) is met for any mass, M, within a mass spectrometer of resolution, R, then the algorithms described herein will be able to unambiguously interpret the spectrum. Thus, in a range 0–2000 Da, a minimum resolution of ~2800 (full width half maximum height) at M=2000 Da is preferred in order to carry out an analysis at 2000 Da, and the fragmentation mass spectrum preferably has a resolution of at least 5600 (full width half peak height) for peptides with a molecular weight up to about 4000 daltons. In a particular embodiment, the mass spectrometer has a resolution greater than about 60,000 (full width half maximum height) at M=2000 Da; a Fourier transform ion cyclotron resonance mass spectrometer is suitable for this purpose.

5.4.2 Ranking and Selection of Deduced Peptide Sequences

If the spectral read algorithm has deduced a plurality of peptide sequences within the parent ion, previously established criteria are applied to rank the deduced peptide sequences. One or more of the following methods are preferred for this purpose: (1) ranking by number of complementary ions, (2) ranking by intensity of selected ions, and (3) a quality index using a vectorial approach. Any two or all three of these methods may be used.

The first method, ion count ranking, is based on the total number of ions (e.g., y, b and a ions) in the fragmentation spectra which match the deduced sequences. (Taylor, J. A. and Johnson, R. S. (1997). Sequence database searches via de novo peptide sequencing by tandem mass spectrometry. Rapid Comm. in Mass Spect. 11, 1067–1075, which is incorporated herein by reference). The second method, ion intensity ranking, uses the sum of individual ion intensities which correspond to the signals assigned to ions (e.g., y, b or a ions) in the fragmentation spectra. A deduced sequence which has a higher value of summed ion intensities is considered more likely than those of lower summed intensities. Taylor & Johnson, ibid.

Figure 3:
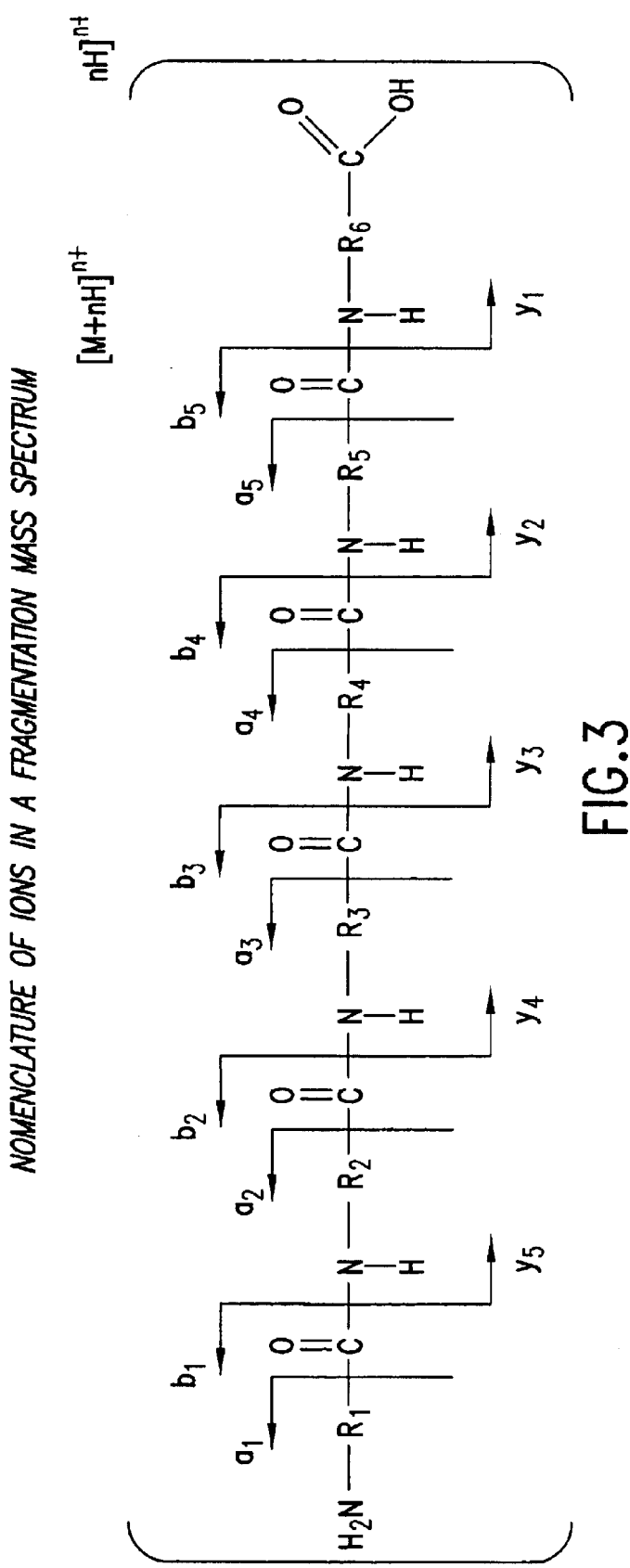
FIG. 3 shows some types of ions in a fragmentation mass spectrum which may be used in practicing the present invention (nomenclature of Biemann 1990).

In the third method, vectorial quality ranking, the values of the whole spectrum (preferably, after intensity thresholding) can be transformed into a vector quantity T. An array of arbitrary size (say, 32,000) is assigned and filled with the value zero. For each data point (mass, intensity) from the original spectrum, the value of intensity is assigned to the $16*m^{th}$ position in the vector, the scaling factor 16 being used to quantize the mass into bins $\frac{1}{16}^{th}$ Da wide. This quantization is lower than the resolution of the instrument, so that there is no loss of data, which could occur if two similar masses could be assigned to the same position in the vector array. The array size of 32,000 is sufficient for a spectrum ranging from 0 to 2,000 Da. Both the array size and the scaling factor can be increased to cope with instruments of higher resolution and for spectra of greater m/z span. A similar operation is performed on the fragmentation spectrum, including all identified a, b and y ions (see FIG. 3 for nomenclature), to produce a vector quantity F. A hit quality index is defined as:

$$hqi = \frac{(T_m \cdot F_m)^2}{(T_m \cdot T_m)(F_m \cdot F_m)}$$

where $T_m$ is the mean centered total spectrum, calculated from the original total spectrum vector T:

$$T_m = T - \frac{\sum_{i=1}^{n} T_i}{n}$$

and $F_m$ is the mean centered fragment spectrum, calculated from the original fragment spectrum F:

$$F_m = F - \frac{\sum_{i=1}^{n} F_i}{n}$$

The quality index will have the value of 0 if there is no match between the total spectrum and the fragment spectrum, and 1 if the fragment spectrum is identical to the total spectrum.

The ranked deduced sequences can then be subjected to a process of selection. In one embodiment, the highest ranking deduced sequence, or a predetermined number of deduced sequences having the highest rank, go forward for further analysis. In another embodiment, a predetermined number of deduced sequences having the highest rank are selected and compared with one another to determine whether a peptide sequence is shared by all (or a specified percentage) of them. If such a shared sequence (a "consensus sequence") is found, it goes forward for further analysis. Additional selection criteria can also be applied at any stage of the spectral read or selection process to tailor the sequences to the database that is to be searched. In one embodiment, deduced sequences are excluded that are incompatible with the selective cleavage procedure that was applied to the peptide under analysis; for a tryptic peptide, deduced sequences can be excluded that contain an internal lysine or arginine residue unless it is immediately followed by a proline residue towards the carboxyterminal side of the peptide. If desired, all peptide sequences deduced by the spectral read algorithm are stored for use in obtaining search strings which preferably are tailored to suit the size, content and characteristics of the database to be searched.

In preferred embodiments of the invention, described in detail below, we have used spectral read algorithms, referred to as HOPS (Holistic Protein Sequencing) and TESLA (Trimer Signature Lookup Algorithm) to deduce sequences that can be used to construct search strings and also to provide information useful for obtaining additional sequence information about peptides or about conceptually translated peptide sequences obtained from analysis of unedited genome sequences (FIG. 1, step 9).

5.4.3 HOPS (Holistic Protein Sequencing)

The spectral read algorithm in HOPS was designed for de novo identification of sequences from fragmentation mass spectra. In one embodiment, HOPS uses the constraint of passing only sequences in which all y, b and a ions can be accounted for in the fragmentation mass spectrum; in another embodiment, this constraint is not imposed. HOPS produces a list comprising one or more identified peptide sequences, which may be of differing lengths; these are then ranked and the top-ranking sequences used to determine a consensus sequence. In one embodiment, vectorial ranking is used and the set of sequences with scores greater than or equal to the score of the top-ranked sequence minus 0.03 are used to determine a consensus sequence.

Figure 4:
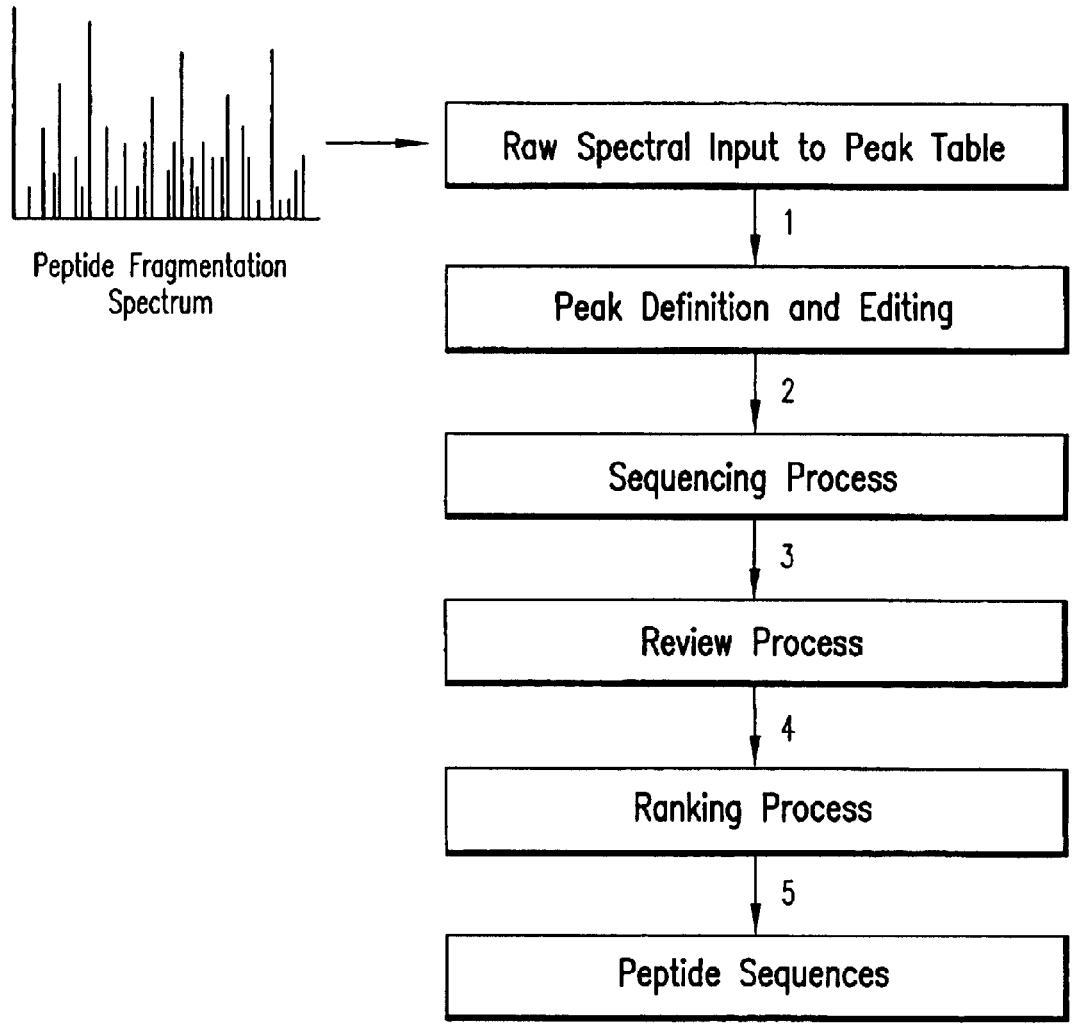
FIG. 4 shows an overview of the modules in the HOPS (Holistic Protein Sequencing) algorithm for the interpretation of fragmentation mass spectra according to a preferred embodiment of the present invention

An overview of one embodiment of the HOPS process which produces (via consensus sequence intermediates) sequences for constructing each database search string is shown in FIG. 4. The sequencing algorithm within HOPS calculates m/z differences between peaks as though they represent masses of the 20 naturally occurring amino acid residues or residues modified by post-translational processing.

In a preferred embodiment, the HOPS algorithm incorporates the following components:

1. A 'Peak table' object. This object incorporates an expandable array of m/z and intensity paired values sorted in order of increasing m/z.
2. A 'Walk' object. This object contains several expandable arrays:
   (a) A m/z value array. This corresponds to peaks from the peak table object which can be assigned to particular amino acid masses;
   (b) A 'b-ion' Boolean flag array. This is set true if the peak in the array in (a) has a complementary ion identified in the peak table (i.e. two ions in the table sum to the mass of the singly protonated parent ion plus one proton);
   (c) A 'a-ion' Boolean flag array. This is set true if the peak in (a) above has a signal with an m/z decrement of 27.997 Da from a b ion signal (corresponding to the loss of a carbon and oxygen from a b ion);

In addition, the walk object contains a floating point value representing the score of the sequence contained in that walk object.
3. The 'Stack'. This is an expandable array of walk objects. Each walk object is identified by an index number which is its relative position on the stack.
4. An Amino acid object. This contains a list of the masses of the amino acid masses applicable in any study. This may be confined to the 20 common naturally occurring amino acids (listed in table 1), or may include masses corresponding to modifications of these amino acids caused by post-translational modifications. The object also contains an identifying symbol for each of the amino acids.

In addition, the algorithm maintains a variable pointing to the index number of the walk currently under consideration.

In a preferred embodiment, all sequence reads from HOPS are kept as possibilities without any pruning or rejection. All possibilities are later reviewed and ranked, and the output sequence is deduced through a consensus process. In a preferred aspect of the present invention, the HOPS method is implemented to obtain highly specific sequence information to be used to search databases comprising proteins, polypeptides, peptides or conceptual polypeptides translated from nucleotide sequences, or any combination thereof. The HOPS method, however is not limited to use with database searching and can also be used as a method for the interpretation of fragmentation mass spectra of peptides without any application of the resulting sequence information to database searching.

Figure 5:
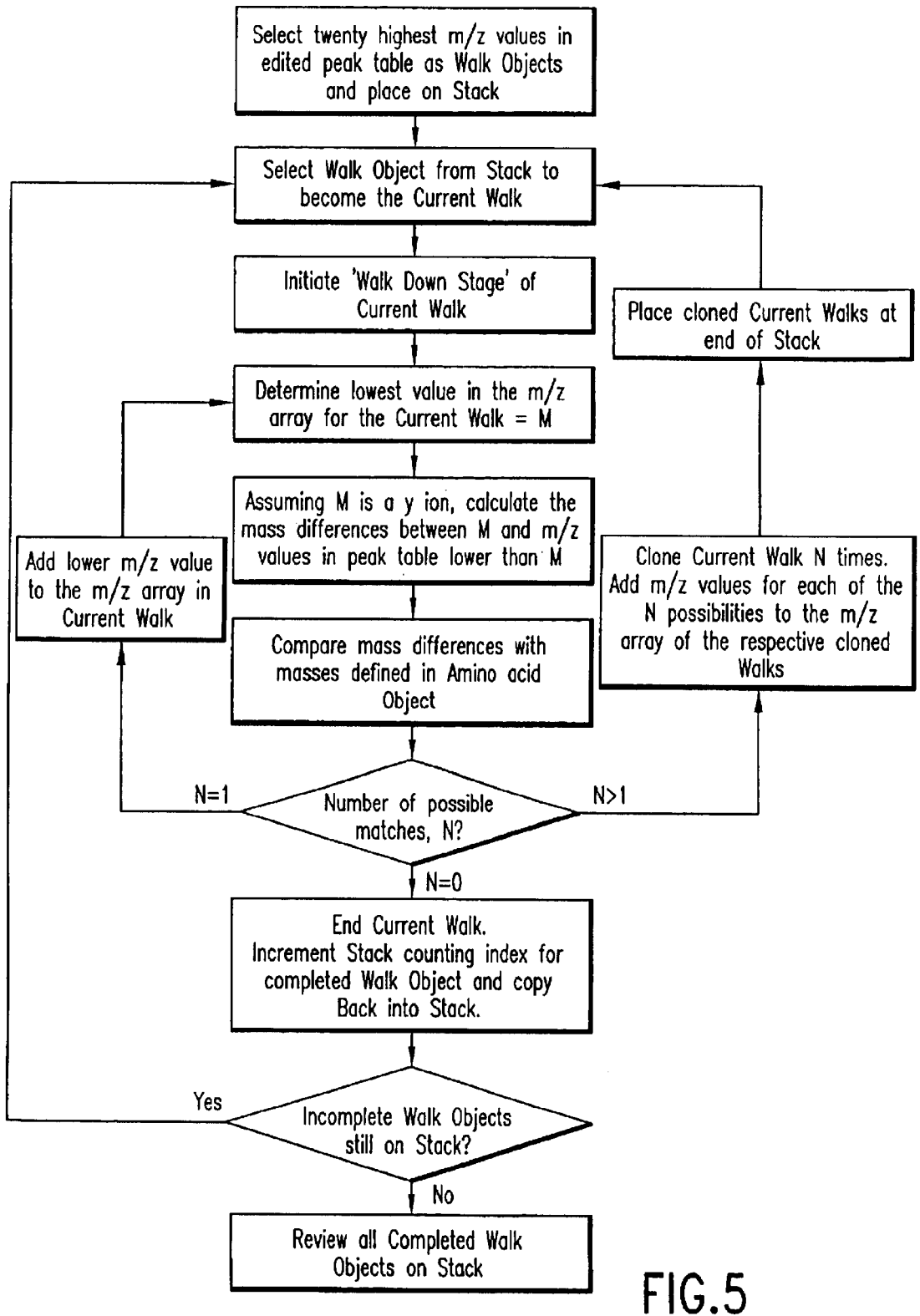
FIG. 5 shows an embodiment of the main peptide sequencing module of HOPS.

In one embodiment of the invention, the sequencing loop of the program is then invoked. A description of the steps involved in the process is shown in the flow chart in FIG. 5. A select number of the highest m/z values remaining in the edited Peak Table object (typically twenty are selected) are then used to create Walk Objects and are placed on the Stack. In this process we assume that the set of the twenty starting m/z walk objects selected above the doubly charged ion will include y ions, and the walking process for each ion is carried out on the basis that we are starting with a y ion and walking down to a lower m/z y ion. We then calculate the mass difference between two peaks in the spectrum as though they were consecutive y ions in order to determine whether that mass difference could correspond to the mass of an amino acid, or modified amino acid. This value is determined within the cumulative error defined by the errors associated with each individual peak (in one embodiment the mass range of this error for the analysis to be equal to [(mass resolution)*$\sqrt{2}$]). Therefore, in the method following, the m/z values present in a particular walk object describe the mass-to-charge ratios of the y-ion fragments formed from the precursor ion.

In one embodiment, the first walk object from the stack is copied into a Walk Object known as the 'Current Walk'. The 'walk down' stage then proceeds. The lowest m/z value in the Current Walk, M, is determined (for the very first walk this will be the starting m/z value). The program then searches through the peak table for all m/z values lower than this value and tests whether the difference between the two m/z values corresponds to any of the amino acid residue masses defined in the amino acid object. In this process, the two m/z ions spaced apart by the mass difference corresponding to an amino acid residue are assumed to be two consecutive y ions. If this is the case, then this value is a possible amino acid to add to the sequence defined in the Current Walk. As there may be more than one possibility for a correspondence, the program tracks the number of possible permutations. If there is only one possibility, then the m/z value of this possibility is added to the current walk, and the updated current walk is then resubmitted to the 'walk down' stage for further processing. If there is more than one possibility, the Current Walk is cloned as many times as necessary, and the appropriate m/z and sequence information is added to the clones, and these clones are added to the end of the stack object. If no possibilities exist, then the Current Walk has terminated at that position, and is copied back into its original position in the Stack. The stack counting index, which refers to the position of the Current Walk, is incremented. If unfinished walk objects remain on the stack, then the next incomplete walk object is taken from the Stack and becomes the new Current Walk. The process continues until there are no more incomplete Walk Objects in the Stack array. In one embodiment of the main sequencing process, all sequences possibilities generated from the 20 initial starting walk objects are kept within the stack, and there is no elimination or pruning process.

Figure 6:
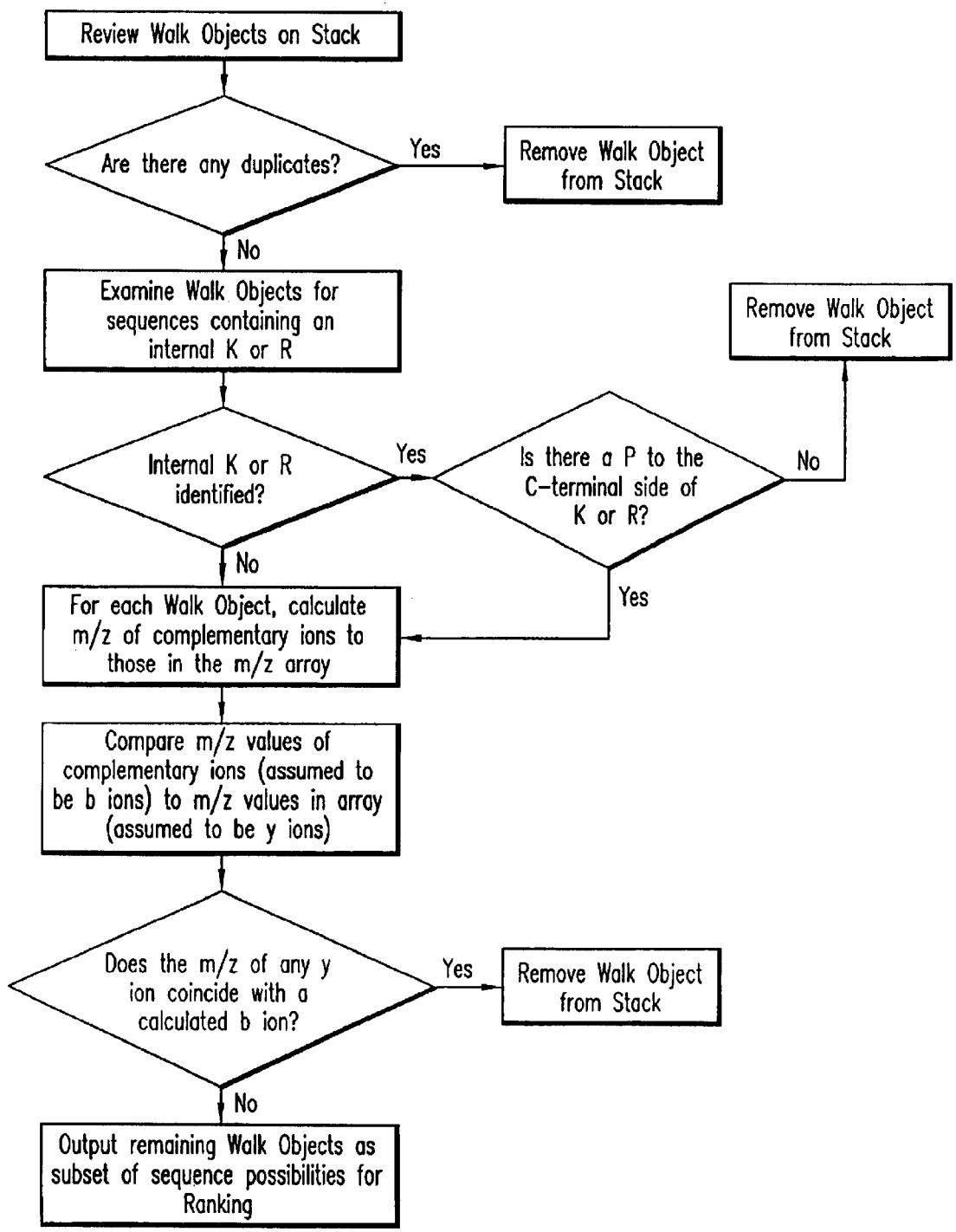
FIG. 6 is a flow chart of one embodiment for editing the peptide sequences generated by the HOPS module.

At this stage, Walk Objects in the Stack are reviewed, and an embodiment of the process is illustrated in the flow chart in FIG. 6. Firstly, sequence solutions are compared against each other to eliminate duplicates and sequences that are subsets of other sequences. Sequence solutions are also rejected where the core sequence contains an internal lysine or arginine amino acid unless the amino acid immediately following at the carboxyl terminus side is a proline. The m/z values present in a particular walk object can arise from y or b ions. Following the process of review, a list of sequences derived from the fragmentation spectrum is produced; in one embodiment, the list comprises all possible sequences that can be derived by the algorithm.

The next step is to rank the sequences in order to identify those which are most likely to be correct, using ion count ranking, ion intensity ranking, and/or vectorial ranking as described above.

FIG. 7 shows an embodiment of the steps used to choose a set of peptide sequences derived from a y-ion correlation analysis of the sequences returned from the ranking method. The consensus sequence is defined as the common partial sequence within the set of peptide sequences that satisfy the prescribed ranking criteria. The consensus sequences are determined by calculating the frequency of occurrence of each y ion signal across the set of top ranked Walk Objects. Walk Objects which are supported by y ion signals for each residue are placed into the consensus set. An amino acid consensus sequence is produced based on mass differences between the common set of sequential y ions which are related by the masses of the 20 naturally-occurring amino acids or their derivatives produced during sample preparation and/or analysis. In one embodiment, if the output of the ranking and y-ion correlation process yield a single sequence, it is used as the sole amino acid sequence for the candidate sequence set. If the consensus sequences are not the same length, in one embodiment the longest one is selected and used to construct a search string. For sequences of the same length, in one embodiment preference is given to those deduced from y ions with m/z values that are of greater value than the m/z value of the doubly-charged precursor ion.

It is well-recognised by those skilled in the art that spectra from different instruments and samples prepared by diverse methods vary in the levels of instrument and chemical noise, both across the full m/z range (upper limit is defined by the mass of the precursor ion) and within defined m/z regions. Further, contamination of the fragmentation spectrum with ions other than those of the precursor peptide ion of interest may contribute significantly to the ions observed at m/z values below the doubly charged precursor ion. As shown in FIG. 7, the HOPS method can use multiple criteria to select sequences for candidate sequence selection to compensate for differences among samples and instruments. For example, using the y ions above the doubly charged precursor ion for certain fragmentation spectra may increase the fidelity of spectral sequence reads since contaminating fragment ions from singly-charged, unrelated peptides having the same mass (±2 Da) as the precursor ions would not be present.

5.4.4 TESLA

HOPS produces a consensus sequence of no prescribed length. By contrast, TESLA interprets the fragmentation mass spectrum to deduce sequences having a uniform, previously ordained length; detection of tripeptide sequences is especially preferred. Establishing a fixed length for the deduced sequences permits other constraints for a search string to be relaxed and thereby facilitates the successful construction of search strings from poorer quality fragmentation mass spectra.

TESLA performs spectral interpretation by pattern recognition, e.g. by performing one or more logical comparisons (preferably logical AND comparisons) between an array representing a mass spectrum and one or more arrays representing peptide signatures to be detected if present in the mass spectrum. In one embodiment, TESLA performs a spectral read by a process that comprises: (a) creating a set of signature arrays containing the mass spectral signatures of a set of peptide sequences (preferably, a set of sequences of identical length, most preferably a set of trimeric peptide sequences); (b) creating a spectral array representing peaks identified in a fragmentation mass spectrum; and (c) performing pattern recognition by comparing the spectral array to the set of signature arrays (e.g. using a logical AND function) to determine whether the mass spectrum contains the signature of a peptide sequence in the set. (FIG. 8)

In a preferred embodiment of TESLA, a linear array is created in which each array comprises a plurality of bits (which may be conceptualized as bins) and each individual bin represents a defined range of assigned mass values (equated to m/z values) in a fragmentation spectrum, so that the bins collectively represent all (or any desired segment) of the x axis in a fragmentation mass spectrum. For example, an array of 2048 bins each 1 Dalton wide will represent a mass spectrum from m/z 1 to 2048. Each bin can be full (the bit is set, i.e., is non-zero) or empty (the bit is zero). To represent a fragmentation mass spectrum in the array, a peak picking algorithm identifies one or more peaks in the array to construct a peak list, which may optionally have been filtered or edited, as described above. For each peak in the peak list, a corresponding bit is set. Thus, for example, if a peak list represents peaks having mean m/z values 112, 146, 255 and 450 and the array has bins 1 Dalton wide, then the bits with assigned numbers ("baryon numbers") 112, 146, 255 and 450 are set while the other bits are zero.

A set of arrays (a "library" of arrays) is created in which all peptides are represented that are to be recognized if they occur in the fragmentation mass spectrum. Thus, to represent all trimeric peptides that can be formed from the 20 naturally occurring amino acids, an library of 8,000 arrays ($20^3$) is needed that collectively represent all possible permutations of three amino acid residues independently chosen from a universe of 20. (To represent all possible tetramers, the library would have $20^4$ arrays.) Preferably, the library includes peptides comprising derivatives produced during sample preparation and/or analysis from the naturally occurring amino acids. If desired, the library can be expanded to represent trimers comprising other amino acid residues, such as those resulting from one or more post-translational modifications). In a preferred embodiment, the size of the library is diminished by treating isobaric amino acid residues (e.g. Ile and Leu) as a single residue (this can be done for one or more sets of isobaric residues) and/or by excluding permutations that are incompatible with the endopeptidase used to produce the experimental peptide. For example, to interpret the mass spectrum of a tryptic fragment, a signature is disallowed if it represents a tripeptide having an Arg or Lys in the first or second position unless the Arg or Lys is immediately followed by a Pro residue; an Arg or Lys in the third position does not result in exclusion.

Each tripeptide in the set (or constrained set) to be recognized is represented in an array by setting four bits so that the intervals between successive non-zero bits represents the monoisotopic mass of a residue in the tripeptide. Thus, to represent the tripeptide Ala-Arg-Asp in an array with bins 1 Dalton wide, the monoisotopic residue masses are rounded Bup or down to the nearest Dalton, giving Ala (71), Arg (156) and Asp (114), an arbitrarily chosen first bit is set (say, baryon number=1), and the remaining bits are set to give intervals corresponding to the rounded monoisotopic masses of the residues in question, creating an array in which bits 1, 72, 228 and 342 are set. In general, to represent tripeptide X-Y-Z respectively having residue masses x, y and z, bits with baryon numbers (c+x), (c+x+y), and (c+x+y+z) are set, where c is an arbitrary sufficiently small number. (As will be obvious to one of skill in the art, one could reverse the process and set bits (c−x), (c−x−y) and (c−x−y−z), where c is an arbitrary sufficiently large number.). In this way, a "motif library" is created in which each array represents a tripeptide that can be recognized if present in the fragmentation mass spectrum (a "candidate signature").

The "databits" array representing peaks in the spectrum is now tested for bits corresponding to peaks that represent a first tripeptide sequence. The corresponding array in the "motif" library is compared to the databits array (using a logical AND comparison) to test whether the databits array has non-zero bits exactly matching the four set bits in the motif array; if so, then the tripeptide represented by the motif is present in the spectrum, and a hit is scored for that tripeptide. Then, each full bit in the motifbits array is shifted ("rolled") up by one baryon number and the logical AND comparison with the databits array is repeated. In this way, the motif is rapidly and efficiently swept through the entire spectrum represented in the databits array, using the relatively fast bit comparison and bit movement operations, and scoring each hit for that tripeptide. In a preferred embodiment, performance is enhanced by first testing whether the first non-zero bit of the motifbits array has a matching non-zero bit in the databits array; if so, the full logical test is carried out, otherwise the motifbits array is immediately rolled to the next position. Once this rolling process (a "bit sweep") is completed through a range corresponding to a previously ordained segment of the fragmentation spectrum that is to be tested, the next array is taken from the motif library and the bit sweep process is repeated.

If a particular tripeptide signature is found in the spectrum, a test is performed to determine whether associated the N-terminal mass is a valid baryon number. The difference between the starting baryon number in the signature and the parent ion mass is determined. If the N-terminal baryon number is less than an arbitary number (preferably 306), then it is looked up in a list of allowed baryon numbers representing the sum of all combinations of 3 amino acid residues from the universe of permitted residues (e.g. the 20 naturally occurring amino acid residues and derivatives produced during sample preparation and/or analysis). The hit is accepted if, and only if, the N-terminal baryon number is valid. In a preferred embodiment, the sum of the intensities of the 4 matching peaks in the databits array is calculated from the peak list and tracked. Preferably, accepted hits are scored differently depending on the region of the mass spectrum in which they occur. If all the matching peaks have m/z values that are greater than or equal to one half of the parent ion mass, the sequence is designated as a "non-straddle" sequence and accepted as a candidate for constructing a search string (optionally subject to additional constraints). If one or two peaks are below this m/z value, the sequence is designated as a "straddle" sequence and may be rejected but preferably is accepted as a candidate for constructing a search string. The range of the spectrum to be tested is preferably set so that no more than two peaks are below the m/z watershed.

Once all matching sequences in the library have been found, they are ranked by vectorial ranking, as described above. In a preferred embodiment, the "straddle" and "non-straddle" sequences are ranked separately.

5.5 Construction of a Search String or Set of Search Strings

The consensus sequence (e.g. from HOPS) or the top-ranked sequence or sequences identified by spectral analysis (e.g. by TESLA) are now analyzed to construct one or more search strings for searching a database. In one embodiment, the four top ranked sequences found by TESLA (preferably, the two top-ranked staddle and the two top-ranked non-straddle sequences) are used to form search strings. In another embodiment, all straddle sequences that share the two top-ranked scores in the straddle category and all non-straddle sequences that share the two top-ranked scores in the non-straddle category are used to form search strings; if multiple sequences tie for the same score, more than four sequences are used. Construction of search strings may be performed by a computer-mediated algorithm that comprises: (a) analyzing a deduced sequence to form a permuted set of search sequences; and (b) constraining the permuted set of search sequences according to previously ordained criteria. In one embodiment, search strings are constructed by a peptide search algorithm such as the FIREPEP module described herein (FIG. 9).

In accordance with the present invention, a "search string" comprises a "search sequence" and "associated mass data" for that search sequence. A search sequence is a peptide sequence that has been deduced by interpreting a fragmentation mass spectrum or that has been derived from a deduced sequence by constraints and/or permutation, as described herein. Preferably, the search sequence is a tripeptide sequence. The associated mass data comprise any two or more of the following: the N-terminal mass (denoted M1), the C-terminal mass (denoted M2), and the total mass. The N-terminal mass (M1) is the mass that flanks the search sequence on the N-terminal side of the experimental peptide, while the C-terminal mass (M2) is the mass that flanks the search sequence on the C-terminal end of the experimental peptide. (FIG. 10)

Since M1 and M2 will be used in searching a database of peptide sequences, it is important to note that the mass of an actual, physical peptide (e.g. the experimental peptide) equals the sum of the masses of the amino acid residues that comprise it (e.g. as stated in Table 1), plus the mass of a molecule of water. The mass of a molecular ion in a mass spectrum further includes the mass of one or more protons, according to its charge state. However, for a peptide sequence in a database, the total mass may be calculated as the sum of the individual amino acid residues, i.e. without adding the mass of a water molecule or of one or more protons. Thus, the appropriate adjustment must be made either by the algorithm that determines M1 and M2 from the mass spectral data, or by the algorithm that calculates M1 and M2 for a peptide sequence in a database. In a preferred embodiment, M1 and M2 are calculated by using the summed masses of the amino acid residues, without including the mass of the water molecule or protons, and this convention is used herein. Alternative conventions may be adopted as a matter of design choice The search strings can readily be tailored to the size and other characteristics of the database to be searched and the resolution of the mass spectrometer. For a large database (e.g. a peptide database derived by conceptual translation of a nucleotide database comprising at least $3 \times 10^9$ nucleotides) a search string preferably contains at least three amino acid residues, but a search string consisting of a dimer or a single amino acid residue may also be used, particularly for searching smaller databases such as conceptually translated peptide databases derived from genomic databases of microorganisms. However, for searching larger databases (e.g., in order to identify which nucleotide sequences in large genome databases encode peptides), a trimer sequence flanked by two masses is preferred in order to retrieve a more practical working set of sequences from peptide databases derived by conceptual translation of nucleotide sequences from a large genomic database. Sequencing algorithms (e.g. HOPS and TESLA) can construct search strings with dimers or sequences greater than three amino acid residues in length but the additional sequence length may be unnecessary and may increase the number of false positive reads from the fragmentation spectra, thereby compromising the fidelity of the overall process. However, it should be noted that in the present invention, any sequence data that do not meet the criteria for a search string may be used in a mapping algorithm as described below, e.g. to edit the retrieved peptide or translated nucleotide database sequences and to remove errors. (FIG. 1, step 7 and FIG. 11).

Criteria for forming and constraining a permuted set of search sequences are illustrated in FIGS. 9 and 10 under 'Constraints for search string' and described below, and may be applied in any desired sequence. These are based on empirical observations and from database attributes. One of ordinary skill in the art can adjust these criteria for improved searching of other databases (e.g. databases representing other genomes) either empirically or from considerations such as genome size, frequency of translated amino acid residues, nucleotide sequencing error rates and gene structure.

In one embodiment, certain disfavored search strings are eliminated that have been found from experience to be frequent artifacts. The identity of disfavored search strings will vary according to the preparative and analytical procedures used, the instruments employed, and the nature of the sample being analyzed, and may readily be determined by experience. In a particular embodiment, the set of disfavored search strings comprises one or more (and preferably all) of the following: M1-GEL-878.6, M1-ELV-779.4, M1-DND-631.4, and M1-TLD-860.5.

In one embodiment, the number of false hits from a large database is reduced by constraining M1 such that it cannot equal the mass of a single naturally occurring amino acid residue; under this constraint, M1 is likely to represent the combined masses of two or more amino acid residues. Alternatively, M1 can be constrained by requiring (1) that M1 does not equal the mass of a single amino acid residue in its natural state or following post-translational modification; or (2) that M1 be greater than 186.079 Daltons (the mass of a residue of Tryptophan, the largest naturally occurring amino acid). Alternatively, or in addition, M2 can be constrained in accordance with the specific endopeptidase used to generate the experimental peptide; for tryptic digestion, the last residue of the experimental peptide must be the C-terminal Arg or Lys residue, thus M2 is required to exceed 156.10 Daltons (the mass of an arginine residue) (FIG. 10). These constraints may be applied by the spectral read algorithm or may be imposed by subsequent steps of the method described herein. In one preferred embodiment, a search sequence is formed from a consensus sequence of HOPS by identifying the most N-terminal tripeptide within the consensus sequence that satisfies the constraints for M1, or for M1 and M2. In another preferred embodiment, the highest ranking tripeptide sequence provided by TESLA is chosen that satisfies the constraints for M1, or for M1 and M2.

Other considerations for constructing a search string arise from (a) the elemental identity of certain "isobaric" residues, which have identical mass, and (b) instrument performance which produces mass ambiguities for both single and multiple residues. These alternative embodiments fall within the method described herein. To account for these mass identities and similarities among the naturally-occurring amino acid residues any or all of the following constraints may be imposed:

1. The amino acids leucine (L) and isoleucine (I) are isobaric isomers i.e. these residues have identical mass (Table 1). Here, the spectral read algorithm uses the symbol L, and this may be permuted to I to form the single residue change. For construction of the permuted search set (FIG. 9), sequences with both Leu and Ile are considered.
2. The amino acid asparagine (N) and two glycine residues (GG) are isobaric isomers and have identical chemical compositions and hence mass.
3. The amino acid residue, phenylalanine (F) has a mass that is similar to that of the oxidised form of methionine (M*) (147.0684 versus 147.0399 Da). Depending on signal intensity and instrument resolution, it may be difficult to achieve sufficient mass accuracy to distinguish these two residues. In one embodiment, the spectral read algorithm always specifies F for both F and oxidized methionine (M*). In constructing the permuted search set, F is permuted to M* and vice versa.
4. The amino acid residue, glutamine (Q) has a mass which may be difficult to distinguish from that of lysine (K) (128.0586 versus 128.0950 Da), depending on signal intensity and instrument resolution. In one embodiment, the spectral read algorithm uses the Q with a change to K for the single residue change. For an experimental peptide obtained by digestion with trypsin, K is included in the allowed trimer sequences only if followed by a Pro residue.
5. The amino acid tryptophan (W) has a mass which may be difficult to distinguish from the masses of three amino acid residue dimers, depending on signal intensity and instrument resolution. This occurs when a signal between the two defining the tryptophan residue (mass=186.0793 Da) in the fragmentation spectrum is below detectable limits. This can produce the following six sequence permutations: (i) alanine (A) and aspartic Acid (D), either AD or DA (mass difference=0.015256 Da) (ii) glycine (G) and glutamic Acid (E), either GE or EG (mass difference=0.015256 Da) (iii) valine (V) and serine (S), either VS or SV (mass difference= 0.21129 Da). Thus, in one embodiment, where a search string contains W, a set of six permuted search strings is constructed; conversely, if a search string contains one of the 6 di-amino acid combinations, the two residues could be permuted to a Trp ('back permutation').
6. The amino acid arginine (R) (156.1011 Da) has a mass which may be difficult to distinguish from that of a combination of valine (V) and glycine (G), depending on signal intensity and instrument resolution (mass difference=0.0011232 Da). Thus, in one embodiment, R is permuted to VG and/or GV, and either of these dimers is back-permuted to R.

In one embodiment, all isobaric and mass-ambiguous amino acid substitutions are taken into account, and so all possible permutations are calculated from a deduced sequence to construct a permuted set of search strings. For example, a partial amino acid sequence of LCW would generate the following 14 possibilities in the Permuted Search set: LCW, ICW, LCDA (SEQ ID NO.: 9), ICDA (SEQ ID NO.: 10), LCAD (SEQ ID NO.: 11), ICAD (SEQ ID NO.: 12), LCGE (SEQ ID NO.: 13), ICGE (SEQ ID NO.: 14), LCEG (SEQ ID NO.: 15), ICEG (SEQ ID NO.: 16), LCVS (SEQ ID NO.: 17), ICVS (SEQ ID NO.: 18), LCSV (SEQ ID NO.: 19), ICSV (SEQ ID NO.: 20). If an amino acid residue in a trimeric deduced sequence is replaced by an isobaric or mass-ambiguous dimer, the set of search sequences may include one or more tetramers.

In a preferred embodiment of the present invention, the first three sequence permutations (L⇌I, F⇌M* and Q⇌K), and permutations of W⇌(AD or DA or VS or SV or EG or GE) are used in the construction of the search strings. In this embodiment, permutations from N⇌GG are not considered.

In yet a further embodiment of the present invention, only the first three sequence permutations (L⇌I, F⇌M* and Q⇌K) are used in the construction of the search strings. In this embodiment, permutations from one amino acid to multiple amino acids (e.g. N⇌GG and W⇌(AD or DA or VS or SV or EG or GE)) are not considered based on the principle that only sequences supported with observed peaks in the fragmentation mass spectrum are used for construction of the search string.

In a preferred embodiment, the mass spectrometer has sufficient resolution to dispel at least one (and preferably all) of the mass ambiguities enumerated as 3–6 above. Accordingly, only isobaric amino acid residues (I vs. L and N vs. GG) are taken into account in forming permuted search strings. In a particular embodiment, only I and L are permuted.

Either before or after formation of the permuted set of search strings, the first and second masses, M1 and M2 are determined. These values are determined within the cumulative error defined by the errors associated with each individual peak (we have calculated the mass range of this error for our current analysis to be equal to [(mass resolution)*√2]). If the spectral read is based on y ion peaks, under the convention used herein, the N-terminal mass (M1) may be calculated as the difference between the mass of the singly-protonated molecular ion, [M+H]$^+$, (which may be obtained from a fragmentation mass spectrum or more preferably from a primary mass spectrum) and the mass of the highest m/z peak in the fragmentation spectrum that defines the bounds of the search sequence (e.g. trimer). Under the convention used herein, the C-terminal mass (M2) may be calculated as the value of the lowest m/z value that defines the bounds of the search sequence (e.g. trimer), minus the combined mass of a water molecule and a proton.

In a preferred implementation, the search sequence is deduced from the spectrum as though the spectral read is based on a y ion series. If the ions considered in the spectral read are in fact b ions, the sequence orientation would be reversed (FIG. 3) and the values of M1 and M2 would change accordingly to M1' and M2'. For example, a string produced with a y ion spectral read, (NH2)-M1-Leu-Val-Ala-M2-(COOH), would become (HOOC)-M2'-Ala-Val-Leu-M1'-(NH2), if b ions are used to deduce the sequence. In one embodiment, both possibilities are taken into account in forming a set of search strings. In another embodiment, the set of search strings is constructed on the assumption that the ions detected are y ions.

In one embodiment for constructing a set of search strings for retrieving a small set of translated nucleotide sequences from the completed human genome:

i) the mass of M1 cannot equal the mass of a single naturally-occurring amino acid residue.

ii) the mass of M2 must be greater than the mass of a protonated arginyl amino acid iii) only a single permuted residue (L→I or F→M*) is allowed within the trimer; and iv) permuted sequences which are based on mass ambiguities between the mass of a single amino acid residue and residue dimers are not incorporated into the set of search strings.

In an alternative embodiment, the following additional constraint is applied:

v) the trimer sequence cannot contain only combinations of the high frequency residues V or A or combinations of either V or A residue and a single permutated residue. For example, IVA would not be allowed as the trimer sequence of a search string.

One of ordinary skill would readily recognize alternative criteria for retrieval of the correct nucleotide sequence, and such criteria may be readily implemented in alternative embodiments of the present invention.

5.6 Searching the Database

The search string or set of search strings may now be used to search a database of peptide sequences. Suitable databases for this purpose include: a database comprising peptide sequences derived from sequencing a plurality of peptides (e.g. by Edman sequencing or by MS analysis); or a database comprising peptide sequences derived by conceptual translation of a plurality of nucleotide sequences; or a database comprising peptide sequences derived by conceptual translation of a database of nucleotide sequences (e.g. a database comprising cDNA sequences and/or genomic sequences). In a particular embodiment, the peptide sequence database is derived by conceptual translation of genomic sequences representing a plant, mammalian or the human genome or a substantial portion thereof (e.g. at least 50%, 60%, 70%, 80%, 90%, 95% or 99% of a plant, mammalian or the human genome). In a preferred embodiment, conceptual translation comprises applying the rules of the universal genetic code to obtain hypothetical peptide sequences by translating the nucleotide database in both orientations, and for all three reading frames of each orientation. Optionally, the conceptually translated database is constrained by excluding any peptide sequence that includes a residue encoded by a codon that appears adjacent to (alternatively after) a stop codon in the relevant reading frame of the nucleotide database that was conceptually translated. If desired, this exclusion criterion may be applied after in silico digestion. In one particular embodiment, sequences in a peptide database (for instance, one derived by conceptual translation) are permuted to allow for all possible sequences that could arise from one or a plurality of types of post-translational modification (e.g. all permutations are constructed that could arise from phosphorylation of Ser, Thr and Tyr residues).

In one embodiment, a peptide database (e.g. one derived from conceptual translation) is subjected to in silico digestion according to one or more specific endopeptidases used for selective cleavage to generate peptide fragments for analysis by mass spectrometry. Such a database may be constrained or edited to remove sequences according to previously established criteria, e.g., the Allowed Database Sequence constraints detailed in FIG. 10. For in silico tryptic digestion, predicted peptides containing more than one Lys or Arg residue are preferably removed except those in which such a residue is immediately followed by a Pro residue on the C-terminal side. Any peptide database may also be amplified by permuting all Met residues to oxidized and unoxidized forms; where a peptide contains multiple Met residues, the database preferably contains all such permutations.

The peptide database to be searched may comprise over 200,000 sequences, over 500,000 sequences, over 1,000,000 sequences, over 10,000,000 sequences, over 100,000,000 sequences, over 1,000,000 sequences, over 5,000,000 sequences, or over 10,000,000 sequences. The methods described herein are capable of searching such a database with a set of search strings within 30 seconds, 20 seconds, 10 seconds, or even 5 seconds.

In order to search the database, a "mass-constrained text search" is performed to identify peptide sequences that (a) have a predicted mass compatible with M1 plus M2 plus the mass of the intervening peptide sequence (e.g. tripeptide); and (b) contain the text string (e.g. tripeptide) in the search sequence or at least one text string (e.g. tripeptide) in a set of search sequences. This may be accomplished by identifying a subset of sequences having the correct predicted mass and then performing a text search on this subset, or applying these criteria in the reverse order, or applying both criteria simultaneously or in succession to peptide sequences in the database without identifying an intermediate subset of sequences. The peptide sequences that satisfy this mass-constrained text search are then tested to identify those compatible with M1 or M2.

In a preferred embodiment, the M1 is mass-matched to the characters immediately preceding the 'text-matched sequence' i.e. toward the putative N-terminal. For M1, the program sequentially calculates the mass of the amino acid residues represented by the database characters starting at the residue closest to the 'N-terminal' end of the 'text matched sequence'. The process continues until the total mass of the character set exceeds the value of M1. If the value of the character set is equal to the value specified by M1 (within pre-determined error ranges dictated by the mass spectrometer resolution as described above), then an N-terminal mass match is made and the sequence is 'passed' for C-terminal mass matching. A similar procedure is then carried out starting at the C-terminal end of the 'text-matched sequence' for the C-terminal mass value. If the adjusted masses of the residues is equal to the experimentally determined C-terminal mass, then the mass-matching process is deemed successful. If the mass matching criteria are not met, then the search returns a null result (signifying no match), and the program moves to the next peptide sequence for which there is a 'text-matched sequence'. As will be evident to one skilled in the art, a sequence containing the tripeptide and having the correct total mass that matches for M1 will in principle also match for M2, and vice versa, so that the matching for M1 or for M2 may optionally be omitted. It is preferable, however, to match for both M1 and M2 in order to avoid compounding errors arising from imprecision of estimating these values from the fragmentation mass spectrum.

The present invention is capable of analyzing fragmentation mass spectral data and identifying a corresponding sequence in a peptide database based on a single subsequence match, for example a single tripeptide match. This is a significant advance over prior art methods, which required identification of two matching subsequences within a peptide for identification.

5.7 Spectral Back-read

For each peptide fragmentation spectrum, the result of the database search (e.g. the output of FIREPEP) is one or more peptide sequences (typically, a single peptide sequence or a small set of peptide sequences) related by total mass, trimer sequence and mass-matched sequences for M1 and M2. In one embodiment, each of the retrieved sequence(s) is assessed by a back read algorithm to identify a sequence, if any, that truly matches the peptide represented in the fragmentation spectrum.

In one embodiment, the back-read is performed by searching for ions from the relevant suite that flank the common trimer sequence. (If both y and b ions have been used for a the search process, the sequence of the matching tripeptide and the values found for M1 and M2 will reveal whether the relevant suite is the y or b ions.) In a preferred embodiment, this process is implemented by searching an appropriate peak list, generated from a fragmentation mass spectrum of the experimental peptide, for flanking y ions. Each sequence is parsed, character by character. The peptide sequences that meet these criteria are used to generate a list of theoretical m/z values for the appropriate suite (preferably, the y ion series). The theoretical m/z values, or corresponding assigned mass values, are compared with the observed values in a peak list from a fragmentation mass spectrum of the experimental peptide. Preferably, the peak list used for the back read and the peak list used for the spectral read are prepared from the same fragmentation mass spectrum, but they may less preferably be prepared from different fragmentation spectra of the experimental peptide. Preferably, the peak list used for the back-read contains at least one peak, more preferably a plurality of peaks, absent from the peak list used for the spectral read process (e.g., the Edited Peak List). In one preferred embodiment, the peak list used for this comparison has not been subjected to filtering or editing or has been subjected to a less stringent filtering or editing process than that applied to obtain the peak list used for the spectral read process. The matching ions (e.g. y-ions) found in the peak list which correspond to the theoretical values are recorded. Peptide sequences are then processed (e.g., in text form) where the trimer sequences are identified, flanking ions which support each sequence are flagged, and the sequences are scored. A preferred scoring scheme which uses one y ion signal on the N terminal end of the peptide and two y ion signals on the C terminal end is as follows for a peptide $NH_2$ ... X[ABC]XX ... COOH (where ABC represents the trimer, X represents an unmatched flanking ion, and * represents a matched flanking ion, as follows:

for X[ABC]XX: score 0
for X[ABC]X*: score 1
for X[ABC]*X: score 2
for X[ABC]**: score 3
for *[ABC]XX: score 4
for *[ABC]X*: score 5
for *[ABC]*X: score 6
for *[ABC]**: score 7

Two of the flanking y ion configurations are used to pass a single database peptide sequence: (i) two signals which define two additional residues on the C-terminal side of the trimer (score=3) or (ii) additional signals which define one and two additional residues on the N-terminal and C-terminal sides of the trimer (score=7). In cases where the FIREPEP results produce peptides with scores 7 and 3, only the sequence with the higher score is passed. In a preferred embodiment, the algorithm is capable of performing the back-read process according to previously determined criteria, without the intervention of an operator. In particular embodiments, the back-read (and if desired the method as a whole) is performed without the intervention of a person having a doctoral degree in science, preferably without the intervention of a person having a master's or higher degree in science, more preferably without the intervention of a person having a bachelor's or higher degree in science, still more preferably without the intervention of a person skilled in mass spectral interpretation, and yet more preferably without the intervention of an operator.

By extending the search sequence in a search string (e.g. extending a trimeric sequence to a sequence of 5, 6, or more amino acid residues through the process described above), the back-read provides the specificity needed to select or verify a true match, and further to delineate expressed gene regions in large genomic databases without using exon-prediction algorithms. For other databases and/or for interpreting fragmentation spectra where other types of ions are prominent, it may be useful to use longer y ion reads and/or to consider other ion types, and such methods are within the scope of the present invention.

In alternative embodiments, the back-read can be performed by a computer-mediated algorithm that allows for gaps in the spectrum and identifies inter-peak offsets corresponding to two or more successive flanking residues in a retrieved sequence, or by a vectorial scoring method, as taught herein.

The result of this step of the method is one "matching" peptide sequence (within the limits of isobaric residues (Leu vs. Ile) and any mass ambiguous residues (e.g., Phe vs. oxidized Met, and Lys vs. Gln) for each tandem spectrum. In a preferred embodiment, mass ambiguity is avoided by using a mass spectrometer with an appropriately high resolution, as described herein. In another preferred embodiment, isobaric residues are distinguished by interpretation of peaks representing d and w ions arising from side chain cleavage. (Biemann, 1990, op. cit.) If the matching peptide sequence occurs in a peptide database derived by conceptual translation of a nucleotide database, then cross-referencing routines can be used to retrieve the sequence from the nucleotide database that encodes the matching peptide sequence.

5.8 Use of Additional Mass Spectrometry Information for Database Mapping

In one embodiment of the present invention, additional information is obtained from accurately determined peptide molecular weights (e.g. as measured in primary mass spectra) and/or fragmentation mass spectra of peptide fragments obtained by selective cleavage (e.g. trypsinolysis) of a polypeptide. The additional data may be mapped onto a peptide or nucleotide database after a matching peptide sequence has been identified using a search sequence deduced from a fragmentation mass spectrum, as described above.

Peptide molecular weights (without associated fragmentation spectra) and additional sequences identified from fragmentation spectra by a spectral read program are useful for: 1) unambiguous identification of exons, i.e. regions within nucleotide sequences that are expressed as peptides; 2) determining a correct reading frame of a nucleotide sequence (e.g. a nucleotide sequence comprising an exon or a portion of an exon); 3) identifying artefacts and errors in nucleotide or peptide sequences; 4) identifying base changes (mutations) and protein polymorphisms; 5) identifying post-translational modifications; and 6) identifying exon-intron boundaries as well as exon-exon boundaries in splice variants. Since exons cannot be identified with certainty from nucleotide sequence data in genomic databases, the capacity for automated, high-throughput verification from experimental data that one or more portions of a hypothetically translated peptide sequence correspond to actual physical peptides is an important aspect of the present invention.

After the backread module has identified one peptide represented in the database that matches to the mass spectral data (within the limits of isobaric residues, e.g. Ile vs. Leu, and optionally within the limits of mass ambiguous residues, e.g. Phe vs. Met* and Lys vs. Gln), conventional methods are used to retrieve and align peptide sequences in a database that overlap with the matching peptide sequence, or with peptide sequences that overlap with other overlapping sequences. (FIG. 13). Mapping to these aligned sequences can now begin, and may comprise one or more of the following functions in any desired combination:

(a) Accurate mass measurements (e.g. from primary mass spectra) of peptide fragments are mapped to the corresponding portions of the aligned sequences in the database by a process of mass matching (Perkins et al. (1999) Electrophoresis 20, 3551–3567, which is incorporated by reference), thereby confirming that they represent actual physical peptides. See FIG. 12 (underlined subsequences).

(b) Peptide sequences deduced by the spectral read program are mapped to the corresponding portions of the aligned sequences, thereby confirming that they represent actual peptides. See FIG. 12 (subsequences in bold). Any (and preferably all) deduced peptide sequences can be used for this purpose, including those that do not satisfy the criteria for a search string. The deduced sequence is permuted and a text search is performed against the set of aligned sequences to identify one or more subsequences that contain a member of the permuted sequence set. The tryptic (or other cleavage) peptide within which the match occurs is tested to see whether it matches the mass data associated with the deduced peptide sequences (e.g. whether M1 and M2 match). In a preferred embodiment, the M1 match is tested by a module that begins with the molecular mass of the amino acid residue on the N-terminal side of the matching sequence and tests whether it matches M1 within the error of measurement, if not, the module iteratively moves to the next flanking residue, adds its molecular mass, and tests whether the sum matches M1. This process is repeated until a match is found or the sum exceeds M1, in which case there is no match. A similar test is performed for flanking residues on the C-terminal side of the matching sequence to test for a match to M2. As will be evident to one of skill in the art, the value of M2 as determined from the fragmentation mass spectrum must be adjusted to conform with the algorithm by which the mass of the C-terminal flanking region is iteratively determined; either the mass of a molecule of water (in addition to the mass of a proton) must be subtracted from the value of M2 determined from the y ion in the fragmentation spectrum, or the mass of a water molecule must be added to the sum calculated for the C-terminal flanking region under consideration. If a match is found for both M1 and M2, optionally a check is made to determine whether the identified subsequence is compatible with the cleavage patten of the endopeptidase that was used to produce the experimental peptides (e.g. for tryptic peptides, the subsequence is checked to determine whether it terminates with a C-terminal Arg or Lys residue and whether its N-terminal is preceded by an Arg or Lys residue). Preferably, such a match is required to accept the subsequence for mapping.

(c) Post-translational modifications (PTMs) within the aligned sequences are identified by a variant of the peptide-mapping algorithm in (b). This is done by modifying the algorithm that tests the summed masses of the flanking amino acid residues against M1 or M2 so that the summed flanking mass is calculated from the molecular mass of each flanking amino acid residue both in its unmodified state and as incremented or decremented by one or more PTMs under consideration or fragments thereof, such as any or all those listed in Table 2. Thus, to consider phosphorylation, the algorithm steps along the flanking sequence and upon encountering a Ser (or Thr or Tyr) keeps parallel totals of the previously summed flanking mass, incremented by the monoisotopic mass of a Ser (or Thr or Tyr) with and without a mass increment due to phosphorylation. The resultant parallel summed flanking masses are then tested in each step against M1 (in the case of an N-terminal flanking sequence) or M2 (for a C-terminal flanking sequence). In a preferred embodiment, a back-read is performed on the fragmentation mass spectrum to identify the characteristic ions of the PTM of interest in order to accept the PTM for mapping. Such characteristic ions include, without limitation: (a) modified fragmentation ions; (b) ions arising from cleavage of side chains; and (c) ions arising from cleavage within side chains.(See, e.g., Gibson, B. W. and Cohen, P. (1990) Methods Enzymol. 193, 480–501)

(d) To detect database sequencing errors or peptide polymorphisms, deduced sequences are mapped onto aligned sequences and the flanking sequences are matched to M1 and M2 as described in (b) above (i.e., without taking PTMs into account) or, more preferably, as described in (c) above (i.e., allowing for PTMs) If a match is found for M1 but not M2, the mapping algorithm returns to the C-terminal flanking sequence and recalculates the flanking mass, permuting one amino acid residue at a time to all other possible amino acids; if a match is found for M2 but not M1, the same operation is performed on the N-terminal flanking sequence. In particular embodiments, the set of possible amino acids can exclude PTMs or can include one or more PTMs. In one embodiment, if a permutation of a given amino acid residue in the sequence produces a match for the relevant flanking mass (M1 or M2), the result is recorded as an error or polymorphism. and the sequence is corrected or the polymorphism is mapped. In a preferred embodiment, a back-read is performed on the fragmentation mass spectrum to identify a peak corresponding to the corrected amino acid residue before recording it as an error. By studying peptides derived from a plurality of individuals from the same species, polymorphisms can be distinguished from sequencing errors. If the uncorrected sequence matches fragmentation spectra from some individuals but not others, it is recorded as a polymorphism; if it never matches, it is recorded as a sequencing error.

(e) The present invention may also be used to identify exon-intron boundaries in one or more genomic sequences that have been conceptually translated to peptide sequences or exon-exon boundaries in splice variants. In one embodiment, this is done by using a "spanning sequence" i.e. a sequence that includes amino acid residues encoded by two distinct exons e.g. two exons separated by a single intron or a plurality of introns. In one embodiment, the spanning sequence is identified by a spectral read program (e.g. is a consensus sequence from HOPS). Preferably the spanning sequence comprises more than 3 amino acid residues, e.g. at least 5, at least 8, at least 10, at least 15, at least 20, at least 25 or at least 30 residues. A text comparison is performed to match a first part of the spanning sequence with a first portion of a conceptually translated peptide sequence encoded by a first exon and to match a second part of the spanning sequence with a second portion of the conceptually translated peptide sequence encoded by a second exon, thereby revealing exon-intron boundaries in the genomic sequence. In a preferred embodiment, the present invention is used to identify exons in a genomic sequence that encodes a protein whose expression is subject to splice variation. Identifying a spanning sequence in such a protein permits identification in the genomic sequence of some or all of the exons which are co-expressed in the splice variant.

In another embodiment, a plurality of aliquots of a polypeptide preparation are subjected in parallel to distinct selective cleavage procedures to generate overlapping cleavage peptides. Parallel in silico digestion of translated peptide sequences is also performed to generate overlapping in silico cleaved peptide sequences, which may now be identified and aligned, as described above. Where an aligned sequence is encoded by more than one exon, the exon-intron boundaries are now revealed. Use of overlapping cleavage fragments advantageously permits greater sequence coverage to be obtained, thereby facilitating the editing of nucleotide databases.

In one embodiment, the FIREPROT module (FIG. 11) performs the mapping function, as exemplified in Example 1 below, using the same permutation rules that are used in FIREPEP.

5.9 Recognition and Mapping of Post-translational Modifications.

The method described herein may be applied to identify, sequence or map a wide variety of post-translational modifications including, without limitation, those that yield: N-formyl-L-methionine; L-selenocysteine; L-cystine; L-erythro-beta-hydroxyasparagine; L-erythro-beta-hydroxyaspartic acid; 5-hydroxy-L-lysine; 3-hydroxy-L-proline; 4-hydroxy-L-proline; 2-pyrrolidone-5-carboxylic acid; L-gamma-carboxyglutamic acid; L-aspartic 4-phosphoric anhydride; S-phospho-L-cysteine; 1'-phospho-L-histidine; 3'-phospho-L-histidine; O-phospho-L-serine; O-phospho-L-threonine; O4'-phospho-L-tyrosine; 2'-[3-carboxamido-3-(trimethylammonio)propyl]-L-histidine; N-acetyl-L-alanine; N-acetyl-L-aspartic acid; N-acetyl-L-cysteine; N-acetyl-L-glutamic acid; N-acetyl-L-glutamine; N-acetylglycine; N-acetyl-L-isoleucine; N2-acetyl-L-lysine; N-acetyl-L-methionine; N-acetyl-L-proline; N-acetyl-L-serine; N-acetyl-L-threonine; N-acetyl-L-tyrosine; N-acetyl-L-valine; N6-acetyl-L-lysine; S-acetyl-L-cysteine; N-formylglycine; D-glucuronyl-N-glycine; N-myristoyl-glycine; N-palmitoyl-L-cysteine; N-methyl-L-alanine; N,N,N-trimethyl-L-alanine; N-methylglycine; N-methyl-L-methionine; N-methyl-L-phenylalanine; N,N-dimethyl-L-proline; omega-N,omega-N'-dimethyl-L-arginine; omega-N,omega-N-dimethyl-L-arginine; omega-N-methyl-L-arginine; N4-methyl-L-asparagine; N5-methyl-L-glutamine; L-glutamic acid 5-methyl ester; 3'-methyl-L-histidine; N6,N6,N6-trimethyl-L-lysine; N6,N6-dimethyl-L-lysine; N6-methyl-L-lysine; N6-palmitoyl-L-lysine; N6-myristoyl-L-lysine; O-palmitoyl-L-threonine; O-palmitoyl-L-serine; L-alanine amide; L-arginine amide; L-asparagine amide; L-aspartic acid 1-amide; L-cysteine amide; L-glutamine amide; L-glutamic acid 1-amide; glycine amide; L-histidine amide; L-isoleucine amide; L-leucine amide; L-lysine amide; L-methionine amide; L-phenylalanine amide; L-proline amide; L-serine amide; L-threonine amide; L-tryptophan amide; L-tyrosine amide; L-valine amide; L-cysteine methyl disulfide; S-farnesyl-L-cysteine; S-12-hydroxyfarnesyl-L-cysteine; S-geranylgeranyl-L-cysteine; L-cysteine methyl ester; S-palmitoyl-L-cysteine; S-diacylglycerol-L-cysteine; S-(L-isoglutamyl)-L-cysteine; 2'-(S-L-cysteinyl)-L-histidine; L-lanthionine; meso-lanthionine; 3-methyl-L-lanthionine; 3'-(S-L-cysteinyl)-L-tyrosine; N6-carboxy-L-lysine; N6-1-carboxyethyl-L-lysine; N6-(4-amino-2-hydroxybutyl)-L-lysine; N6-biotinyl-L-lysine; N6-lipoyl-L-lysine; N6-pyridoxal phosphate-L-lysine; N6-retinal-L-lysine; L-allysine; L-lysinoalanine; N6-(L-isoglutamyl)-L-lysine; N6-glycyl-L-lysine; N-(L-isoaspartyl)-glycine; pyruvic acid; L-3-phenyllactic acid; 2-oxobutanoic acid; N2-succinyl-L-tryptophan; S-phycocyanobilin-L-cysteine; S-phycoerythrobilin-L-cysteine; S-phytochromobilin-L-cysteine; heme-bis-L-cysteine; heme-L-cysteine; tetrakis-L-cysteinyl iron; tetrakis-L-cysteinyl diiron disulfide; tris-L-cysteinyl triiron trisulfide; tris-L-cysteinyl triiron tetrasulfide; tetrakis-L-cysteinyl tetrairon tetrasulfide; L-cysteinyl homocitryl molybdenum-heptairon-nonasulfide; L-cysteinyl molybdopterin; S-(8alpha-FAD)-L-cysteine; 3'-(8alpha-FAD)-L-histidine; O4'-(8alpha-FAD)-L-tyrosine; L-3',4'-dihydroxyphenylalanine; L-2',4',5'-topaquinone; L-tryptophyl quinone; 4'-(L-tryptophan)-L-tryptophyl quinone; O-phosphopantetheine-L-serine; N4-glycosyl-L-asparagine; S-glycosyl-L-cysteine; O5-glycosyl-L-hydroxylysine; O-glycosyl-L-serine; O-glycosyl-L-threonine; 1'-glycosyl-L-tryptophan; O4'-glycosyl-L-tyrosine; N-asparaginyl-glycosylphosphatidylinositol-ethanolamine; N-aspartyl-glycosylphosphatidylinositol-ethanolamine; N-cysteinyl-glycosylphosphatidylinositol-ethanolamine; N-glycyl-glycosylphosphatidylinositol-ethanolamine; N-seryl-glycosylphosphatidylinositolethanolamine; N-alanyl-glycosylphosphatidylinositolethanolamine; N-seryl-glycosylsphingolipidinositolethanolamine; O-(phosphoribosyl dephospho-coenzyme A)-L-serine; omega-N-(ADP-ribosyl)-L-arginine; S-(ADP-ribosyl)-L-cysteine; L-glutamyl 5-glycerylphosphorylethanolamine; S-sulfo-L-cysteine; O4'-sulfo-L-tyrosine; L-bromohistidine; L-2'-bromophenylalanine; L-3'-bromophenylalanine; L-4'-bromophenylalanine; 3',3",5'-triiodo-L-thyronine; L-thyroxine; L-6'-bromotryptophan; dehydroalanine; (Z)-dehydrobutyrine; dehydrotyrosine; L-seryl-5-imidazolinone glycine; L-3-oxoalanine; lactic acid; L-alanyl-5-imidazolinone glycine; L-cysteinyl-5-imidazolinone glycine; D-alanine; D-allo-isoleucine; D-methionine; D-phenylalanine; D-serine; D-asparagine; D-leucine; D-tryptophan; L-isoglutamyl-polyglycine; L-isoglutamyl-polyglutamic acid; O4'-(phospho-5'-adenosine)-L-tyrosine;

S-(2-aminovinyl)-D-cysteine; L-cysteine sulfenic acid; S-glycyl-L-cysteine; S-4-hydroxycinnamyl-L-cysteine; chondroitin sulfate D-glucuronyl-D-galactosyl-D-galactosyl-D-xylosyl-L-serine; dermatan 4-sulfate D-glucuronyl-D-galactosyl-D-galactosyl-D-xylosyl-L-serine; heparan sulfate D-glucuronyl-D-galactosyl-D-galactosyl-D-xylosyl-L-serine; N6-formyl-L-lysine; O4-glycosyl-L-hydroxyproline; O-(phospho-5'-RNA)-L-serine; L-citrulline; 4-hydroxy-L-arginine; N-(L-isoaspartyl)-L-cysteine; 2'-alpha-mannosyl-L-tryptophan; N6-mureinyl-L-lysine; 1-chondroitin sulfate-L-aspartic acid ester; S-(6-FMN)-L-cysteine; 1'-(8alpha-FAD)-L-histidine; omega-N-phospho-L-arginine; S-diphytanylglycerol diether-L-cysteine; alpha-1-microglobulin-Ig alpha complex chromophore; bis-L-cysteinyl bis-L-histidino diiron disulfide; hexakis-L-cysteinyl hexairon hexasulfide; N6-(phospho-5'-adenosine)-L-lysine; N6-(phospho-5'-guanosine)-L-lysine; L-cysteine glutathione disulfide; S-nitrosyl-L-cysteine; N4-(ADP-ribosyl)-L-asparagine; L-beta-methylthioaspartic acid; 5'-(N6-L-lysine)-L-topaquinone; S-methyl-L-cysteine; 4-hydroxy-L-lysine; N4-hydroxymethyl-L-asparagine; O-(ADP-ribosyl)-L-serine; L-cysteine oxazolecarboxylic acid; L-cysteine oxazolinecarboxylic acid; glycine oxazolecarboxylic acid; glycine thiazolecarboxylic acid; L-serine thiazolecarboxylic acid; L-phenylalanine thiazolecarboxylic acid; L-cysteine thiazolecarboxylic acid; L-lysine thiazolecarboxylic acid; O-(phospho-5'-DNA)-L-serine; keratan sulfate D-glucuronyl-D-galactosyl-D-galactosyl-D-xylosyl-L-threonine; L-selenocysteinyl molybdopterin guanine dinucleotide; O4'-(phospho-5'-RNA)-L-tyrosine; 3-(3'-L-histidyl)-L-tyrosine; L-methionine sulfone; dipyrrolylmethanemethyl-L-cysteine; S-(2-aminovinyl)-3-methyl-D-cysteine; O4'-(phospho-5'-DNA)-L-tyrosine; O-(phospho-5'-DNA)-L-threonine; O4'-(phospho-5'-uridine)-L-tyrosine; N-(L-glutamyl)-L-tyrosine; S-phycobiliviolin-L-cysteine; phycoerythrobilin-bis-L-cysteine; phycourobilin-bis-L-cysteine; N-L-glutamyl-poly-L-glutamic acid; L-cysteine sulfinic acid; L-3',4',5'-trihydroxyphenylalanine; O-(sn-1-glycerophosphoryl)-L-serine; 1-thioglycine; heme P460-bis-L-cysteine-L-tyrosine; O-(phospho-5'-adenosine)-L-threonine; tris-L-cysteinyl-L-cysteine persulfido-bis-L-glutamato-L-histidino tetrairon disulfide trioxide; L-cysteine persulfide; 3'-(1'-L-histidyl)-L-tyrosine; heme P460-bis-L-cysteine-L-lysine; 5-methyl-L-arginine; 2-methyl-L-glutamine; N-pyruvic acid 2-iminyl-L-cysteine; N-pyruvic acid 2-iminyl-L-valine; heme-L-histidine; S-selenyl-L-cysteine; N6-methyl-N6-poly(N-methyl-propylamine)-L-lysine; hemediol-L-aspartyl ester-L-glutamyl ester; hemediol-L-aspartyl ester-L-glutamyl ester-L-methionine sulfonium; L-cysteinyl molybdopterin guanine dinucleotide; trans-2,3-cis-3,4-dihydroxy-L-proline; pyrroloquinoline quinone; tris-L-cysteinyl-L-N1'-histidino tetrairon tetrasulfide; tris-L-cysteinyl-L-N3'-histidino tetrairon tetrasulfide; tris-L-cysteinyl-L-aspartato tetrairon tetrasulfide; N6-pyruvic acid 2-iminyl-L-lysine; tris-L-cysteinyl-L-serinyl tetrairon tetrasulfide; bis-L-cysteinyl-L-N3'-histidino-L-serinyl tetrairon tetrasulfide; O-octanoyl-L-serine. One of ordinary skill in the art would readily recognize that other post-translational modifications occur. One skilled in the art would readily recognise the ability to use the molecular weight for these modifications and incorporate them into the method described and claimed herein.

One of ordinary skill will readily recognize that the methods described herein may be used to detect a variety of post-translational modifications relevant to basic research or to the clinical diagnosis of disease. Examples of the types of PTMs that may be analyzed using the methods described herein include, but are not limited to, alkylation, see e.g. Saragoni et al. (2000) Differential association of tau with subsets of microtubules containing posttranslationally-modified tubulin variants in neuroblastoma cells. Neurochem. Res. 25:59–70; Fanapour et al. (1999) Hyperhomocysteinemia: an additional cardiovascular risk factor. WMJ 98:51–4; Raju et al. (1997) N-Myristoyltransferase overexpression in human colorectal adenocarcinomas. Exp. Cell Res. 235:145–54; Zhao et al. (2000) Palmitoylation of apolipoprotein B is required for proper intracellular sorting and transport of cholesteroyl esters and triglycerides. Mol. Biol. Cell 11:721–34; or Seabra MC (1996) Nucleotide dependence of Rab geranylgeranylation. Rab escort protein interacts preferentially with GDP-bound Rab. J. Biol. Chem. 271:14398–404, the contents of which are hereby incorporated in their entirety.

Examples of phosphorylation include, but are not limited to, Vanmechelen et al. (2000) Quantification of tau phosphorylated at threonine 181 in human cerebrospinal fluid: a sandwich ELISA with a synthetic phosphopeptide for standardization. Neurosci. Lett. 85:49–52; Lutz et al. (1994) Characterization of protein serine/threonine phosphatases in rat pancreas and development of an endogenous substrate-specific phosphatase assay. Pancreas 9:418–24; Gitlits et al. (2000) Novel human autoantibodies to phosphoepitopes on mitotic chromosomal autoantigens (MCAs). J. Investig. Med. 48:172–82; or Quin and McGuckin (2000) Phosphorylation of the cytoplasmic domain of the MUC1 mucin correlates with changes in cell-cell adhesion. Int. J. Cancer 87:499–506, the contents of which are hereby incorporated in their entirety.

A example of sulfation includes, but is not limited to, Manzella et al. (1995) Evolutionary conservation of the sulfated oligosaccharides on vertebrate glycoprotein hormones that control circulatory half-life. J. Biol. Chem. 270S:21665–71, the contents of which is hereby incorporated in its entirety.

Examples of post-translational modification by oxidation or reduction include, but are not limited to, Magsino et al. (2000) Effect of triiodothyronine on reactive oxygen species generation by leukocytes, indices of oxidative damage, and antioxidant reserve. Metabolism 49:799–803; or Stief et al. (2000) Singlet oxygen inactivates fibrinogen, factor V, factor VIII, factor X, and platelet aggregation of human blood. Thromb. Res. 97:473–80, the contents of which are hereby incorporated in their entirety.

Examples of ADP-ribosylation include, but are not limited to, Galluzzo et al. (1995) Involvement of CD44 variant isoforms in hyaluronate adhesion by human activated T cells. Eur. J. Immunol. 25:2932–9; or Thraves et al. (1986) Differential radiosensitization of human tumour cells by 3-aminobenzamide and benzamide: inhibitors of poly(ADP-ribosylation). Int. J. Radiat. Biol. Relat. Stud. Phys. Chem. Med. 50:961–72, the contents of which are hereby incorporated in their entirety.

A example of hydroxylation includes, but is not limited to, Brinckmann et al. (1999) Overhydroxylation of lysyl residues is the initial step for altered collagen cross-links and fibril architecture in fibrotic skin. J. Invest. Dermatol. 113:617–21, the contents of which is hereby incorporated in its entirety.

Examples of glycosylation include, but are not limited to, Johnson et al. (1999) Glycan composition of serum alpha-fetoprotein in patients with hepatocellular carcinoma and non-seminomatous germ cell tumour. Br. J. Cancer 81:1188–95; Fulop et al. (1996) Species-specific alternative splicing of the epidermal growth factor-like domain 1 of cartilage aggrecan. Biochem. J. 319:935–40; Dow et al. (1994) Molecular correlates of spinal cord repair in the embryonic chick: heparan sulfate and chondroitin sulfate proteoglycans. Exp. Neurol. 28:233–8; Kelly et at. (1993) RNA polymerase II is a glycoprotein. Modification of the COOH-terminal domain by O-GlcNAc. J. Biol. Chem. 268:10416–24; Goss et al. (1995) Inhibitors of carbohydrate processing: A new class of anticancer agents. Clin. Cancer Res. 1:935–44; or Sleat et al. (1998) Specific alterations in levels of mannose 6-phosphorylated glycoproteins in different neuronal ceroid lipofuscinoses. Biochem. J. 334:547–51, the contents of which are hereby incorporated in their entirety.

An example of glycosylphosphatidylinositide addition includes, but is not limited to, Poncet et al. (1996) CD24, a glycosylphosphatidylinositol-anchored molecule is transiently expressed during the development of human central nervous system and is a marker of human neural cell lineage tumors. Acta Neuropathol. (Berl.) 91:400–8, the contents of which is hereby incorporated in its entirety.

An example of ubiquitination includes, but is not limited to, Chu et al. (2000) Ubiquitin immunochemistry as a diagnostic aid for community pathologists evaluating patients who have dementia. Mod. Pathol. 13:420–6, the contents of which is hereby incorporated in its entirety.

An example of a translocation leading to a disease state includes, but is not limited to, Reddy et al. (1999) Recent advances in understanding the pathogenesis of Huntington's disease. Trends Neurosci. 22:248–55, the contents of which is hereby incorporated in its entirety.

An example of detection of an artificial modification (e.g., biotinylation, cross-linking, photoaffinity labeling) includes, but is not limited to, Romero et al. (1993) Differential T cell receptor photoaffinity labeling among H-2Kd restricted cytotoxic T lymphocyte clones specific for a photoreactive peptide derivative. Labeling of the alpha-chain correlates with J alpha segment usage. J. Exp. Med. 177:1247–56, the contents of which is hereby incorporated in its entirety.

The methods described herein may also be used to detect proteolytic processing or changes associated with transcription or genetic changes. Examples of proteolytic processing include, but are not limited to, Kurahara et al. (1999) Expression of MMPS, MT-MMP, and TIMPs in squamous cell carcinoma of the oral cavity: correlations with tumor invasion and metastasis. Head Neck 21:627–38; or Thorgeirsson et al. (1994) Tumor invasion, proteolysis, and angiogenesis. J. Neurooncol. 18:89–103, the contents of which are hereby incorporated in their entirety.

Examples of primary sequence variability (e.g., mRNA splicing variability, gene mutation) include, but are not limited to, Fulop et al. (1996) Species-specific alternative splicing of the epidermal growth factor-like domain 1 of cartilage aggrecan. Biochem. J. 319:935–40; or Bergquist et al (2000) Rapid Method to Characterize Mutations in Transthyretin in Cerebro spinal Fluid from Familial Amyloidotic Polyneuropathy Patients by Use of Matrix-assisted Laser Desorption/Ionization Time-of-Flight Mass Spectrometry. Clin. Chem. 46:1293–1300, the contents of which are hereby incorporated in their entirety.

5.10 EXAMPLE 1

In one example of the present invention, a database is constructed from a combination of human genomic sequence entries in the database held at the European Molecular Biology Laboratory (EMBL), peptide entries in the non-redundant database held by the National Centre for Biotechnology Information (NCBI) which is accessible at hffp://www.ncbi.nlm.nih.gov/ and peptide sequence entries held at the SWISSPROT database held at the Swiss Institute of Bioinformatics (SIB). The genomic sequences (including edited as well as unassembled, unordered segments of the genome) are translated, in all three reading frames and in both directions, into a computer listing of predicted amino acid sequences by applying the rules of the genetic code to form conceptually translated peptide sequences. The theoretical peptide sequences are conceptually cleaved at the residues predicted by the specificity of trypsin to generate a list of predicted tryptic fragments. Peptides containing stop codon nucleotide sequences (usually indicated by an '*' in the translated database) or characters not corresponding to the 21 amino acids of Table I are not entered into the peptide database. Peptides with translated nearest neighbor stop codons (one or two flanking residues) are rejected. Both the oxidized and unoxidized form of peptides containing Met, as well as all permutations if the peptide contains multiple Met residues, are entered into the database. The rules used to build the peptide database satisfy the 'Allowed Database Sequence' constraints detailed in FIG. 10. The combination of criteria for building the search string and those used to build the peptide database confer a high specificity to the FIREPEP search engine.

FIG. 12 shows 6 sequences which are retrieved from the translated human genome and protein database using the search string 226.15-NEN-621 .34. For purposes of presentation, the translated genome sequence (Sequences 1–5) which show the identified peptide sequences represent nucleotide sequences which are flanked by stop codons. From another fragmentation spectrum derived from the same sample or protein mixture (FIG. 1), a dimer sequence and associated M1 and M2 values (718.37-SF-274.19) are determined. This dimer string does not adhere to the set of empirical rules required for database searching using FIREPEP (FIG. 10) and is not used to search the database. Using the FIREPROT algorithm the SF dimer and associated masses are assigned to database entries 1, 3 and 6 (FIG. 12), which are clustered by a conventional alignment algorithm. In addition the asses of all tryptic peptides from the database entries are compared to the mass list resulting from the MALDI-TOF analysis. These masses correspond predominantly to the [M+H]+ peptide species. The observed protonated molecular ions (Table 3) are mass matched to the database polypeptides (Perkins et al. (1999) Electrophoresis 20, 3551–1567), as indicated by the underlined sequences in FIG. 12. To deduce the presence of phosphorylation using another fragmentation spectrum from the sample, the residue masses of, for example, Ser, Thr or Tyr residues are incremented by a mass=79.9663 (Table 2) and included in the residue mass table available to FIREPROT. These additional masses can then be used in the M1 and M2 calculations during FIREPROT sequence mapping.

5.11 EXAMPLE 2

Peptide sequences are derived by conceptual translation of genome sequences and subjected to in silico trypsinolysis. Fragmentation mass spectra are interpreted by HOPS and the conceptually translated database is searched with FIREPEP to identify matching peptide sequences. Where a peptide sequence is identified that matches the search string, a cross-referencing algorithm identifies the contig in the genomic database from which the matching peptide has been translated. A set is then formed from all in silico digested sequences encoded by that contig. A mass matching algorithm is used to assign recorded masses to sequences within the set of translated peptide sequences. Sequences deduced from spectral read of tandem spectra are mapped onto the set of translated sequences. In addition, observed masses are attributed to molecular weight increments and decrements to account for post-translational modifications of interest. As shown in FIG. 13, the output of database peptide sequences are read into the mass-mapping and post-translational modification module. The first step is to produce all possible peptide masses for the sequences and for the post-translational modifications of interest. For example, to consider phosphorylation, the mass of all peptides containing Ser, Thr or Tyr residues are incremented by a mass=79.9663 for each of the residues which could be phosphorylated. All possible combinations are calculated. Thus, the modified peptide mass list consists of all masses, unmodified and modified, for each peptide which could result from endoprotease digestion and post-translational modifications of interest. The modified mass list is then used to compare with the experimentally-determined peptide mass list. All mass agreements with translated genome peptide sequences within the mass tolerance of the instrument are used to determine sequence coverage and post-translational modifications. Table 3 lists the masses matched to peptides of the transferrin receptor gene.

5.12 EXAMPLE 3

It is well recognised that changes in single nucleotides occur with high frequency among the genomes of individuals. The biological consequences of single nucleotide polymorphisms (SNPs) can be profound. The propensity to develop a form of Alzheimer's disease is associated with a single base pair change in apolipoprotein E (Apo E) which converts the Cys residues at position 130 (the ∈3 isoform) to Arg (∈4 isoform). The tryptic peptides containing the amino acid change from the SNP are (R)LGADMEDVCGR (SEQ ID NO.: 21) and (R)LGADMEDVR (SEQ ID NO.: 22) for isoforms ∈3 and ∈4, respectively. Apolipoprotein E peptides from individuals with the ∈3 and ∈4 polymorphism were analysed according to the present invention. Two SNP specific tryptic peptides were produced which yielded the following M1-trimer-M2 sequences: M1=241 (DME) M2=573 (∈3), and M1=241 (DME) M2=476 (∈4). The SNP search sequences were used to search the human genome peptide database with the FIREPEP module. In the case of the ∈3 search string Apo E gene sequences were returned. The search with ∈4 did not return any records.

6. EMBODIMENTS OF THE INVENTION

Various preferred embodiments of the present invention may be defined as follows:
1. A computer-based method for determining whether or not a first peptide sequence database contains one or more peptide sequences that correspond to an experimental peptide, the method comprising:
   (a) analyzing a first fragmentation spectrum obtained by mass spectrometry of the experimental peptide to generate a first peak list comprising an assigned mass value for each of a plurality of peaks detected in the first fragmentation spectrum;
   (b) interpreting the first peak list by a computer-mediated spectral read to construct one or more search sequences (X) and deriving from a fragmentation mass spectrum of the experimental peptide alone or in combination with a primary mass spectrum of the experimental peptide two or more of the following mass data: a mass (M1) of a sequence flanking the N-terminus of X, a mass (M2) of a sequence flanking the C-terminus of X, and a total mass, wherein each search sequence and associated mass data together constitute a search string (M1-X-M2);
   (c) searching the first database with at least one search string to determine whether the first database contains one or more candidate sequences that include a search sequence of a search string and are compatible with the mass data associated with that search string; and
   (d) performing a computer-mediated back-read that tests the candidate sequences, if any, against the first peak list or a second peak list derived from a fragmentation spectrum of the experimental peptide and determining whether one or more candidate sequences fit the data in the peak list according to one or more matching criteria,
   wherein upon satisfaction of the matching criteria, the candidate sequences, if any, that satisfy the matching criteria are identified as corresponding sequences.
2. The method according to embodiment 1, wherein the back-read is performed without the intervention of an operator.
3. The method according to embodiment 1 or 2, wherein steps (a), (b), (c) and (d) are executed by one or more automated computer algorithms without the intervention of an operator.
4. The method according to any one of the preceding embodiments, wherein the back-read of step (d) comprises testing the candidate peptide sequences, if any, against a second peak list derived from the first fragmentation spectrum that contains at least one peak absent from the first peak list.
5. The method according to any one of the preceding embodiments, wherein the back-read of step (d) comprises
   (i) for each candidate sequence,
      (1) identifying one or more amino acids flanking the search sequence (X) that is included in the candidate sequence;
      (2) generating a list of theoretical m/z values of at least one suite of ions for the identified flanking amino acids;
      (3) comparing the theoretical m/z values or corresponding assigned mass values with observed values in the first peak list or a second peak list derived from the first fragmentation spectrum and recording any matches that support the flanking amino acids; and
   (ii) scoring the supported flanking amino acids and determining whether a candidate sequences satisfies the matching criteria.
6. The method according to any one of the preceding embodiments, wherein:
   step (b) comprises constructing a plurality of search strings having distinct search sequences; and
   step (c) comprises searching the first database with a plurality of search strings to determine whether the first database contains one or more candidate sequences that include a search sequence of a search string and are compatible with the mass data associated with that search string.
7. The method according to any one of the preceding embodiments, wherein the one or more search sequences are constructed by a computer-mediated process comprising:
   (i) interpreting the first peak list to deduce at least one peptide sequence within the experimental peptide;

(ii) selecting at least one deduced sequence; and
(iii) constraining the deduced sequence or sequences to obtain the one or more search sequences.

8. The method according to any one of embodiments 1–6, wherein the one or more search sequences are constructed by a computer-mediated process comprising:
   (i) interpreting the first peak list to deduce at least one peptide sequence within the experimental peptide;
   (ii) selecting at least one deduced sequence;
   (iii) permuting the deduced sequence or sequences to obtain a set of one or more permuted sequences; and
   (iv) constraining the set of one or more permuted sequences to obtain the one or more search sequences.

9. The method according to embodiment 7 or 8, wherein each deduced peptide sequence has a previously ordained maximum length.

10. The method according to embodiment 9, wherein the maximum length is 3 amino acids.

11. The method according to any one of embodiments 7 to 10, wherein the selecting step comprises at least one of the following ranking procedures: ion-count ranking, ion-intensity ranking, and vectorial quality ranking.

12. The method according to any one of embodiments 7 to 11, wherein previously ordained criteria govern the steps of selecting, constraining and, if performed, permuting.

13. The method according to any one of the preceding embodiments, wherein the spectral read comprises determining whether or not a defined segment of the fragmentation mass spectrum contains peaks whose relative spacing defines a member of a set of recognized peptides, the method comprising:
   (a) generating a set of signature arrays each having a plurality of bits, the bits of each signature array being set so that the relative positions of the set bits represent the relative spacing of mass spectral peaks defining a member of the set of recognized peptides, wherein each member of the set of recognized peptides is represented by a signature array;
   (b) generating a spectral array having a plurality of bits, the bits of the spectral array being set so that the relative positions of the set bits represent the relative spacing of a plurality of peaks detected in the fragmentation mass spectrum; and
   (c) iteratively repeating the steps of (1) performing a logical AND comparison between the signature array and the spectral array to determine whether the spectral array contains a set bit that matches each set bit of the signature array, and (2) shifting each set bit of the signature array from its present position by a previously ordained number of bits in a specified direction such that the set bits of the signature array are shifted from a starting position to a stopping position, the starting and stopping positions defining the segment of the fragmentation spectrum being inspected,
   wherein a positive result for an AND comparison indicates that peaks defining the peptide represented in the signature array are present in the fragmentation mass spectrum at the present positions represented by the set bits of the signature array.

14. The method according to any one of the preceding embodiments, wherein the first peptide sequence database is obtained by conceptual translation of a plurality of sequences in a nucleotide sequence database.

15. The method according to any one of embodiments 1–13, wherein the experimental peptide is prepared by selective cleavage of a polypeptide and the first peptide sequence database is obtained by in silico digestion of a second peptide sequence database in accordance with the specificity of the selective cleavage.

16. The method according to embodiment 15, wherein the second peptide sequence database is obtained by conceptual translation of a plurality of sequences in a nucleotide sequence database.

17. The method according to embodiment 14 or 16, wherein the nucleotide sequence database comprises one or more genomic sequences.

18. The method according to embodiment 17, wherein the nucleotide sequence database comprises sequences representing at least 50% of the human genome.

19. The method according to embodiment 14 or 16, wherein the nucleotide sequence database comprises one or more expressed sequence tags (ESTs).

20. The method according to any one of the preceding embodiments, wherein the fragmentation spectrum is obtained by low energy collision-induced dissociation.

21. The method according to embodiment 20, wherein the fragmentation spectrum is obtained using a Q-TOF mass spectrometer.

22. The method according to embodiment 21, wherein the spectral read does not use spectral information from peaks having mass-to-charge (m/z) ratios less than that of the peak whose m/z value is next below that of the doubly protonated molecular ion.

23. The method according to any one of embodiments 1 to 19, wherein the fragmentation spectrum is obtained by high energy collision-induced dissociation.

24. The method according to embodiment 23, wherein, wherein the fragmentation spectrum is obtained using a TOF-TOF mass spectrometer.

25. The method according to embodiment 24, wherein the spectral read uses spectral information from one or more peaks having mass-to-charge (m/z) ratios less than half that of the singly protonated molecular ion.

26. The method according to any one of the preceding embodiments, wherein generating the first peak list comprises detecting at least three peaks in the first fragmentation spectrum and filtering to exclude at least one detected peak from the first peak list.

27. The method according to any one of the preceding embodiments, wherein generating the first peak list comprises preparing an intermediate peak list comprising an assigned mass value for each of at least three peaks detected in the first fragmentation spectrum and editing the intermediate peak list by excluding at least one peak to obtain the first peak list.

28. The method according to any one of the preceding embodiments, wherein each search sequence (X) is a tripeptide sequence.

29. The method according to any one of the preceding embodiments, further comprising:
   (e) using additional mass spectrometric data to obtain additional information about a matching sequence in the peptide sequence database, wherein the additional information is selected from the group consisting of: a post-translational modification and a sequencing error.

30. The method according to any one of the preceding embodiments, further comprising:
   (e) using additional mass spectrometric data to obtain additional information about a nucleotide sequence in a nucleotide database that encodes a matching sequence in the peptide sequence database, wherein the additional information is selected from the group consisting of: identity of an expressed sequence, a reading frame, a cluster of related sequences, a plurality of redundant sequences, a sequencing error, and a polymorphism 31. The method according to any one of the preceding embodiments, wherein the two or more mass data are derived from the first peak list alone or in combination with a primary mass spectrum of the experimental peptide.

32. The method according to embodiment 31, wherein the two or more mass data are derived from the first peak list.

33. A computer-mediated method for determining whether or not a defined segment of a fragmentation mass spectrum contains peaks whose relative spacing defines a member of a set of recognized peptides, the method comprising:
   (a) generating a set of signature arrays each having a plurality of bits, the bits of each signature array being set so that the relative positions of the set bits represent the relative spacing of mass spectral peaks defining a member of the set of recognized peptides, wherein each member of the set of recognized peptides is represented by a signature array;
   (b) generating a spectral array having a plurality of bits, the bits of the spectral array being set so that the relative positions of the set bits represent the relative spacing of a plurality of peaks detected in the fragmentation mass spectrum; and
   (c) iteratively repeating the steps of (1) performing a logical AND comparison between the signature array and the spectral array to determine whether the spectral array contains a set bit that matches each set bit of the signature array, and (2) shifting each set bit of the signature array from its present position by a previously ordained number of bits in a specified direction such that the set bits of the signature array are shifted from a starting position to a stopping position, the starting and stopping positions defining the segment of the fragmentation spectrum being inspected, wherein a positive result for an AND comparison indicates that peaks defining the peptide represented in the signature array are present in the fragmentation mass spectrum at the present positions represented by the set bits of the signature array.

34. The method according to embodiment 33, wherein the recognized peptides are tripeptides.

35. The method according to embodiment 33 or 34, wherein the step of shifting comprises shifting each set bit of the signature array by one bit.

36. The method according to any one of embodiments 33–35, wherein the starting position represents a higher m/z ratio in the fragmentation mass spectrum than the stopping position.

37. The method according to any one of embodiments 33–36, wherein each bit of a signature array or spectral array represents an m/z interval of 1 in the fragmentation mass spectrum.

38. A computer-readable medium comprising instructions for causing a computer to perform the method according to any one of the preceding embodiments.

39. A computer comprising instructions for performing the method according to any one of the preceding embodiments.

40. A peptide or nucleic acid database comprising information obtained by performing the method according to any one of the preceding embodiments.

41. A computer-readable file comprising information obtained by performing the method according to any one of the preceding embodiments.

42. A display comprising information obtained by performing the method according to any one of the preceding embodiments.

The present invention is not to be limited in terms of the particular embodiments described in this application, which are intended as illustrations of individual aspects of the invention. Functionally equivalent methods and apparatus within the scope of the invention, in addition to those enumerated herein, will be apparent to those skilled in the art from the foregoing description and accompanying drawings. Such modifications and variations are intended to fall within the scope of the appended claims. Each reference cited above is hereby incorporated by reference in its entirety.

TABLE 1

Amino acid residue monoisotopic masses

| Amino Acid | Symbol | Elemental Composition | Monoisotopic mass (Da) |
| --- | --- | --- | --- |
| Alanine | A | $C_3H_5NO$ | 71.037114 |
| Arginine | R | $C_6H_{12}N_4O$ | 156.10111 |
| Asparagine | N | $C_4H_6N_2O_2$ | 114.042927 |
| Aspartic Acid | D | $C_4H_5NO_3$ | 115.026943 |
| Carbamidomethyl Cysteine[1] | C | $C_5H_8N_2O_2S$ | 160.03065 |
| Glutamic Acid | E | $C_5H_7NO_3$ | 129.042593 |
| Glutamine | Q | $C_3H_8N2O_2$ | 128.058577 |
| Glycine | G | $C_2H_3NO$ | 57.021464 |
| Histidine | H | $C_6H_7N_3O$ | 137.058912 |
| Isoleucine | I | $C_6H_{11}NO$ | 113.084064 |
| Leucine | L | $C_6H_{11}NO$ | 113.084064 |
| Lysine | K | $C_6H_{12}N_2O$ | 128.094963 |
| Methionine | M | $C_5H_9NOS$ | 131.040485 |
| Oxidised Methionine | M* | $C_5H_9NO_2S$ | 147.035340 |
| Phenylalanine | F | $C_9H_9NO$ | 147.068414 |
| Proline | P | $C_5H_7NO$ | 97.052764 |
| Serine | S | $C_3H_5NO_2$ | 87.032028 |
| Threonine | T | $C_4H_7NO_2$ | 101.047678 |
| Tryptophan | W | $C_{11}H_{10}N_2O$ | 186.079313 |
| Tyrosine | Y | $C_9H_9NO_2$ | 163.063328 |
| Valine | V | $C_5H_9NO$ | 99.068414 |

[1]All cysteine residues are modified to carbamidomethyl cyteine (also known as carbamido cysteine) during our production process, which includes the use of iodoacetamide.

TABLE 2

Examples of mass changes arising from post-translational modification

| Modification | Monoisotopic mass change (Da) |
| --- | --- |
| Acetylation | 42.0373 |
| Phosphorylation | 79.9799 |
| Homoserine formed from Met by CNBr treatment | −29.9928 |
| Pyroglutamic acid formed from Gln | −17.0265 |
| C-terminal amide formed from Gly | −0.9847 |
| Methylation | 14.0269 |
| Hydroxylation | 15.9994 |
| Oxidation of Met | 15.9994 |
| Formylation | 28.0104 |
| Carboxylation of Asp and Glu | 44.0098 |
| Sulfation | 80.0642 |
| Cysteinylation | 119.1442 |
| Pentoses (Ara, Rib, Xyl) | 132.1161 |
| Deoxyhexoses (Fue, Rha) | 146.143 |
| Hexosamines (GalN, GlcN) | 161.1577 |
| Hexoses (Fuc, Gal, Glc, Man) | 162.1424 |
| Lipoic acid (amide bond to Lys) | 188.3147 |
| N-acetylhexosamines (GalNAc, GlcNAc) | 203.195 |
| Farnesylation | 204.3556 |
| Myristylation | 210.3598 |
| Biotinylation (amide bond to Lys) | 226.2994 |
| Pyridoxal phosphate (Schiff Base formed to Lys) | 231.1449 |
| Palmitoylation | 238.4136 |

TABLE 2-continued

Examples of mass changes arising from post-translational modification

| Modification | Monoisotopic mass change (Da) |
|---|---|
| Stearoylation | 266.4674 |
| Geranylgeranylation | 272.4741 |
| N-acetylneuraminic acid | 291.2579 |
| Glutathionylation | 305.3117 |
| N-glycolylneuraminic acid (NeuGc) | 307.2573 |
| 5'-Adenosylation | 329.2091 |
| 4'-Phosphopantotheine | 339.3294 |
| ADP-ribosylation (NAD) | 541.3052 |

TABLE 3

Assigned masses for peptides mapped to the Transferrin receptor gene

| Mass of singly protonated peptide | Maldi Peptide Matches | ppm |
|---|---|---|
| 1084.59209 | AFTYINLDK (SEQ ID NO: 23) | −22 |
| 936.48636 | AVLGTSNFK (SEQ ID NO: 24) | 31 |
| 872.43325 | DAWGPGAAK (SEQ ID NO: 25) | −8 |
| 1610.80827 | DENLALYVENQFR (SEQ ID NO: 26) | −17 |
| 806.39179 | DGFQPSR (SEQ ID NO: 27) | −15 |
| 808.40533 | DLNQYR (SEQ ID NO: 28) | −13 |
| 773.39502 | DQHFVK (SEQ ID NO: 29) | −1 |
| 1288.68379 | DSAQNSVIIVDK (SEQ ID NO: 30) | −7 |
| 1217.56546 | EEPGEDFPAAR (SEQ ID NO: 31) | −18 |
| 1672.8441 | GFVEPDHYVVVGAQR (SEQ ID NO: 32) | 0 |
| 1977.92353 | HPVTGQFLYQDSNWASK (SEQ ID NO: 33) | 11 |
| 713.41117 | IPELNK (SEQ ID NO: 34) | 12 |
| 708.38883 | ITFAEK (SEQ ID NO: 35) | 6 |
| 1282.64946 | LAQMFSDMVLK (SEQ ID NO: 36) | 3 |
| 1561.72694 | LAVDEEENADNNTK (SEQ ID NO: 37) | −19 |
| 1197.61076 | LDSTDFTGTIK (SEQ ID NO: 38) | −9 |
| 1655.729 | LFGNMEGDCPSDWK (SEQ ID NO: 39) | −28 |
| 1204.65388 | LLNENSYVPR (SEQ ID NO: 40) | −17 |
| 1616.8125 | LTHDVELNLDYER (SEQ ID NO: 41) | −13 |
| 1095.51951 | LTTDFGNAEK (SEQ ID NO: 42) | 11 |
| 1033.53257 | LTVSNVLK (SEQ ID NO: 43) | −57 |
| 986.52812 | LVHANFGTK (SEQ ID NO: 44) | 14 |
| 952.48181 | LYWDDLK (SEQ ID NO: 45) | −5 |
| 797.42723 | MVTSESK (SEQ ID NO: 46) | −69 |
| 1358.61735 | QVDGDNSHVEMK (SEQ ID NO: 47) | −12 |
| 1745.87097 | SAFSNLFGGEPLSYTR (SEQ ID NO: 48) | −12 |
| 958.51392 | SGVGTALLLK (SEQ ID NO: 49) | 83 |
| 1468.84215 | SSGLPNIPVQTISR (SEQ ID NO: 50) | −20 |
| 1565.80219 | VEYHFLSPYVSPK (SEQ ID NO: 51) | −1 |
| 1513.80462 | VSASPLLYTLIEK (SEQ ID NO: 52) | −8 |
| 1226.66333 | YNSQLLSFVR (SEQ ID NO: 53) | −8 |

We claim:

1. A computer-based method for determining whether or not a first peptide sequence database contains one or more peptide sequences that correspond to an experimental peptide, the method comprising:
 (a) analyzing a first fragmentation spectrum obtained by mass spectrometry of the experimental peptide to generate a first peak list comprising an assigned mass value for each of a plurality of peaks detected in the first fragmentation spectrum;
 (b) interpreting the first peak list by a computer-mediated spectral read to construct one or more search sequences (X) and deriving from a fragmentation mass spectrum of the experimental peptide alone or in combination with a primary mass spectrum of the experimental peptide two or more mass data selected from the group consisting of: a mass (M1) of a sequence flanking the N-terminus of X, a mass (M2) of a sequence flanking the C-terminus of X, and a total mass, wherein each search sequence and associated mass data together constitute a search string;
 (c) searching the first database with at least one search string to determine whether the first database contains one or more candidate sequences that include a search sequence (X) of a search string and any two or more mass data selected from the group consisting of M1, M2 and the total mass associated with that search string; and
 (d) performing a computer-mediated back-read that tests the candidate sequences, if any, against the first peak list derived from a fragmentation spectrum of the experimental peptide and determining whether one or more candidate sequences match the search sequence (X) of the search string and any two or more mass data selected from the group consisting of M1, M2 and the total mass associated with the search string;
 where upon, the one or more candidate sequences, if any, that match are identified as corresponding sequences.

2. The method according to claim 1, wherein the back-read of step (d) is performed without the intervention of an operator.

3. The method according to claim 1, wherein steps (a), (b), (c) and (d) are executed by one or more automated computer algorithms without the intervention of an operator.

4. The method according to claim 1, wherein the back-read of step (d) comprises testing the candidate peptide sequences, if any, against an edited peak list derived from the first fragmentation spectrum, the edited peak list containing at least one peak absent from the first peak list.

5. The method according to claim 1, wherein the back-read of step (d) comprises:
 (i) for each candidate sequence:
  (1) identifying one or more amino acids flanking the search sequence (X);
  (2) generating a list of theoretical m/z values of at least one suite of ions for the identified flanking amino acids;
  (3) comparing the theoretical m/z values or corresponding assigned mass values with observed values in the first peak list derived from the first fragmentation spectrum and recording any matches that support the flanking amino acids; and (ii) scoring the supported flanking amino acids and determining whether a candidate sequence satisfies the matching criteria.

6. The method according to claim 1, wherein step (b) comprises constructing a plurality of search strings having distinct search sequences and step (c) comprises searching the first database with a plurality of search strings to determine whether the first database contains one or more candidate sequences that include a search sequence of a search string and any two or more mass data selected from the group consisting of M1, M2 and the total mass associated with that search string.

7. The method according to claim 1, wherein the one or more search sequences are constructed by a computer-mediated process comprising:
(i) interpreting the first peak list to deduce at least one peptide sequence within the experimental peptide;
(ii) selecting at least one deduced sequence; and
(iii) constraining the deduced sequence or sequences to obtain the one or more search sequences.

8. The method according to claim 7, wherein each deduced peptide sequence has a previously ordained maximum length.

9. The method according to claim 7, wherein the selecting step comprises at least one of the following ranking procedures: ion-count ranking, ion-intensity ranking, and vectorial quality ranking.

10. The method according to claim 7, wherein previously ordained criteria govern the steps of selecting and constraining.

11. The method according to claim 1, wherein the one or more search sequences are constructed by a computer-mediated process comprising:
(i) interpreting the first peak list to deduce at least one peptide sequence within the experimental peptide;
(ii) selecting at least one deduced sequence;
(iii) permuting the deduced sequence or sequences to obtain a set of one or more permuted sequences; and
(iv) constraining the set of one or more permuted sequences to obtain the one or more search sequences.

12. The method according to claim 11, wherein each deduced peptide sequence has a previously ordained maximum length.

13. The method according to claim 11, wherein the selecting step comprises at least one of the following ranking procedures: ion-count ranking, ion-intensity ranking, and vectorial quality ranking.

14. The method according to claim 11, wherein previously ordained criteria govern the steps of selecting, constraining and permuting.

15. The method according to claim 1, wherein the computer-mediated spectral read comprises determining whether or not a defined segment of the fragmentation mass spectrum contains peaks whose relative spacing defines a member of a set of recognized peptides, the method comprising:
(a) generating a set of signature arrays each having a plurality of bits, the bits of each signature array being set so that the relative positions of the set bits represent the relative spacing of mass spectral peaks defining a member of the set of recognized peptides, wherein each member of the set of recognized peptides is represented by a signature array;

(b) generating a spectral array having a plurality of bits, the bits of the spectral array being set so that the relative positions of the set bits represent the relative spacing of a plurality of peaks detected in the fragmentation mass spectrum; and
(c) iteratively repeating the steps of:
(1) performing a logical AND comparison between the signature array and the spectral array to determine whether the spectral array contains a set bit that matches each set bit of the signature array; and
(2) shifting each set bit of the signature array from its present position by a previously ordained number of bits in a specified direction such that the set bits of the signature array are shifted from a starting position to a stopping position, the starting and stopping positions defining the segment of the fragmentation spectrum being inspected;
wherein a positive result for an AND comparison indicates that peaks defining the peptide represented in the signature array are present in the fragmentation mass spectrum at the present positions represented by the set bits of the signature array.

16. The method according to claim 1, wherein the first peptide sequence database is obtained by conceptual translation of a plurality of sequences in a nucleotide sequence database.

17. The method according to claim 1, wherein the experimental peptide is prepared by selective cleavage of a polypeptide and the first peptide sequence database is obtained by in silico digestion of a second peptide sequence database in accordance with the specificity of the selective cleavage.

18. The method according to claim 17, wherein the second peptide sequence database is obtained by conceptual translation of a plurality of sequences in a nucleotide sequence database.

19. The method according to claim 1, wherein the fragmentation spectrum is obtained by low energy collision-induced dissociation.

20. The method according to claim 19, wherein the spectral read does not use spectral information from peaks having mass-to-charge (m/z) ratios less than that of the peak whose m/z value is next below that of the doubly protonated molecular ion.

21. The method according to claim 1, wherein the fragmentation spectrum is obtained by high energy collision-induced dissociation.

22. The method according to claim 21, wherein the spectral read uses spectral information from one or more peaks having mass-to-charge (m/z) ratios less than half that of the singly protoiiated molecular ion.

23. The method according to claim 1, wherein generating the first peak list comprises detecting at least three peaks in the first fragmentation spectrum and filtering to exclude at least one detected peak from the first peak list.

24. The method according to claim 23, wherein generating the first peak list comprises preparing an intermediate peak list comprising an assigned mass value for each of at least three peaks detected in the first fragmentation spectrum and editing the intermediate peak list by excluding at least one peak to obtain the first peak list.

25. The method according to claim 1, wherein each search sequence (X) is a tripeptide sequence.

* * * * *

SEQUENCE LISTING

<160> NUMBER OF SEQ ID NOS: 52

<210> SEQ ID NO 1
<211> LENGTH: 164
<212> TYPE: PRT
<213> ORGANISM: Homo sapiens

<400> SEQUENCE: 1

Val His Leu Lys Gly Ile Phe Ser Ser Arg Leu Leu Asn Glu Asn Ser
1               5                   10                  15

Tyr Val Pro Arg Glu Ala Gly Ser Gln Lys Asp Glu Asn Leu Ala Leu
                20                  25                  30

Tyr Val Glu Asn Gln Phe Arg Glu Phe Lys Leu Ser Lys Val Trp Arg
            35                  40                  45

Asp Gln His Phe Val Lys Ile Gln Val Lys Asp Arg Tyr Val Glu Arg
        50                  55                  60

Trp Pro Arg Ile Val Ser Gln Asp Thr Asp Tyr Pro Tyr Leu Gly Thr
65                  70                  75                  80

Thr Met Asp Thr Tyr Lys Glu Leu Ile Glu Arg Ile Pro Glu Leu Asn
                85                  90                  95

Lys Val Ala Arg Ala Ala Ala Glu Val Ala Gly Gln Phe Val Ile Lys
                100                 105                 110

Leu Thr His Asp Val Glu Leu Asn Leu Asp Tyr Glu Arg Tyr Asn Ser
            115                 120                 125

```
Gln Leu Leu Ser Phe Val Arg Asp Leu Asn Gln Tyr Arg Ala Asp Ile
    130                 135                 140

Lys Val Ser Thr Asp Ser Asn Tyr Val Phe Ile Leu Leu Asn Val Lys
145                 150                 155                 160

Tyr Phe Glu Met

<210> SEQ ID NO 2
<211> LENGTH: 75
<212> TYPE: PRT
<213> ORGANISM: Homo sapiens

<400> SEQUENCE: 2

Val Gln Leu Trp Asn Phe Val Ser Leu Gly Phe Met Ile Gly Tyr Leu
1               5                   10                  15

Gly Tyr Cys Lys Gly Val Glu Pro Lys Thr Glu Cys Glu Arg Leu Ala
            20                  25                  30

Gly Thr Glu Ser Pro Val Arg Glu Pro Gly Glu Asp Phe Pro Ala
        35                  40                  45

Ala Arg Arg Leu Tyr Trp Asp Asp Leu Lys Arg Lys Leu Ser Glu Lys
    50                  55                  60

Leu Asp Ser Thr Asp Phe Thr Gly Thr Ile Lys
65                  70                  75

<210> SEQ ID NO 3
<211> LENGTH: 164
<212> TYPE: PRT
<213> ORGANISM: Homo sapiens

<400> SEQUENCE: 3

Val His Leu Lys Gly Ile Phe Ser Ser Arg Leu Leu Asn Glu Asn Ser
1               5                   10                  15

Tyr Val Pro Arg Glu Ala Gly Ser Gln Lys Asp Glu Asn Leu Ala Leu
            20                  25                  30

Tyr Val Glu Asn Gln Phe Arg Glu Phe Lys Leu Ser Lys Val Trp Arg
        35                  40                  45

Asp Gln His Phe Val Lys Ile Gln Val Lys Asp Arg Tyr Val Glu Arg
    50                  55                  60

Trp Pro Arg Ile Val Ser Gln Asp Thr Asp Tyr Pro Tyr Leu Gly Pro
65                  70                  75                  80

Thr Met Asp Thr Tyr Lys Glu Leu Ile Glu Arg Ile Pro Glu Leu Asn
                85                  90                  95

Lys Val Ala Arg Ala Ala Ala Glu Val Ala Gly Gln Phe Val Ile Lys
            100                 105                 110

Leu Thr His Asp Val Glu Leu Asn Leu Asp Tyr Glu Arg Tyr Asn Ser
        115                 120                 125

Gln Leu Leu Ser Phe Val Arg Asp Leu Asn Gln Tyr Arg Ala Asp Ile
    130                 135                 140

Lys Val Ser Thr Asp Ser Asn Tyr Val Phe Ile Leu Leu Asn Val Lys
145                 150                 155                 160

Tyr Phe Glu Met

<210> SEQ ID NO 4
<211> LENGTH: 75
<212> TYPE: PRT
<213> ORGANISM: Homo sapiens

<400> SEQUENCE: 4
```

```
Val Gln Leu Trp Asn Phe Val Ser Leu Gly Phe Met Ile Gly Tyr Leu
1               5                   10                  15

Gly Tyr Cys Lys Gly Val Glu Pro Lys Thr Glu Cys Glu Arg Leu Ala
            20                  25                  30

Gly Thr Glu Ser Pro Val Arg Glu Glu Pro Gly Glu Asp Phe Pro Ala
        35                  40                  45

Ala Arg Arg Leu Tyr Trp Asp Asp Leu Lys Arg Lys Leu Ser Glu Lys
    50                  55                  60

Leu Asp Ser Thr Asp Phe Thr Gly Thr Ile Lys
65                  70                  75

<210> SEQ ID NO 5
<211> LENGTH: 75
<212> TYPE: PRT
<213> ORGANISM: Homo sapiens

<400> SEQUENCE: 5

Val Gln Leu Trp Asn Phe Val Ser Leu Gly Phe Met Ile Gly Tyr Leu
1               5                   10                  15

Gly Tyr Cys Lys Gly Val Glu Pro Lys Thr Glu Cys Glu Arg Leu Ala
            20                  25                  30

Gly Thr Glu Ser Pro Val Arg Glu Glu Pro Gly Glu Asp Phe Pro Ala
        35                  40                  45

Ala Arg Arg Leu Tyr Trp Asp Asp Leu Lys Arg Lys Leu Ser Glu Lys
    50                  55                  60

Leu Asp Ser Thr Asp Phe Thr Gly Thr Ile Lys
65                  70                  75

<210> SEQ ID NO 6
<211> LENGTH: 760
<212> TYPE: PRT
<213> ORGANISM: Homo sapiens

<400> SEQUENCE: 6

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175
```

```
Lys Leu Ser Lys Val Trp Arg Asp Gln His Phe Val Lys Ile Gln Val
            180                 185                 190
Lys Asp Ser Ala Gln Asn Ser Val Ile Ile Val Asp Lys Asn Gly Arg
            195                 200                 205
Leu Val Tyr Leu Val Glu Asn Pro Gly Gly Tyr Val Ala Tyr Ser Lys
            210                 215                 220
Ala Ala Thr Val Thr Gly Lys Leu Val His Ala Asn Phe Gly Thr Lys
225                 230                 235                 240
Lys Asp Phe Glu Asp Leu Tyr Thr Pro Val Asn Gly Ser Ile Val Ile
            245                 250                 255
Val Arg Ala Gly Lys Ile Thr Phe Ala Glu Lys Val Ala Asn Ala Glu
            260                 265                 270
Ser Leu Asn Ala Ile Gly Val Leu Ile Tyr Met Asp Gln Thr Lys Phe
            275                 280                 285
Pro Ile Val Asn Ala Glu Leu Ser Phe Phe Gly His Ala His Leu Gly
            290                 295                 300
Thr Gly Asp Pro Tyr Thr Pro Gly Phe Pro Ser Phe Asn His Thr Gln
305                 310                 315                 320
Phe Pro Pro Ser Arg Ser Ser Gly Leu Pro Asn Ile Pro Val Gln Thr
            325                 330                 335
Ile Ser Arg Ala Ala Ala Glu Lys Leu Phe Gly Asn Met Glu Gly Asp
            340                 345                 350
Cys Pro Ser Asp Trp Lys Thr Asp Ser Thr Cys Arg Met Val Thr Ser
            355                 360                 365
Glu Ser Lys Asn Val Lys Leu Thr Val Ser Asn Val Leu Lys Glu Ile
            370                 375                 380
Lys Ile Leu Asn Ile Phe Gly Val Ile Lys Gly Phe Val Glu Pro Asp
385                 390                 395                 400
His Tyr Val Val Gly Ala Gln Arg Asp Ala Trp Gly Pro Gly Ala
            405                 410                 415
Ala Lys Ser Gly Val Gly Thr Ala Leu Leu Leu Lys Leu Ala Gln Met
            420                 425                 430
Phe Ser Asp Met Val Leu Lys Asp Gly Phe Gln Pro Ser Arg Ser Ile
            435                 440                 445
Ile Phe Ala Ser Trp Ser Ala Gly Asp Phe Gly Ser Val Gly Ala Thr
            450                 455                 460
Glu Trp Leu Glu Gly Tyr Leu Ser Ser Leu His Leu Lys Ala Phe Thr
465                 470                 475                 480
Tyr Ile Asn Leu Asp Lys Ala Val Leu Gly Thr Ser Asn Phe Lys Val
            485                 490                 495
Ser Ala Ser Pro Leu Leu Tyr Thr Leu Ile Glu Lys Thr Met Gln Asn
            500                 505                 510
Val Lys His Pro Val Thr Gly Gln Phe Leu Tyr Gln Asp Ser Asn Trp
            515                 520                 525
Ala Ser Lys Val Glu Lys Leu Thr Leu Asp Asn Ala Ala Phe Pro Phe
            530                 535                 540
Leu Ala Tyr Ser Gly Ile Pro Ala Val Ser Phe Cys Phe Cys Glu Asp
545                 550                 555                 560
Thr Asp Tyr Pro Tyr Leu Gly Thr Thr Met Asp Thr Tyr Lys Glu Leu
            565                 570                 575
Ile Glu Arg Ile Pro Glu Leu Asn Lys Val Ala Arg Ala Ala Ala Glu
            580                 585                 590
```

```
Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760

<210> SEQ ID NO 7
<211> LENGTH: 12
<212> TYPE: PRT
<213> ORGANISM: Homo sapiens

<400> SEQUENCE: 7

Arg Glu Glu Ala Glu Asn Thr Leu Gln Ser Phe Arg
1               5                   10

<210> SEQ ID NO 8
<211> LENGTH: 0
<212> TYPE:
<213> ORGANISM:

<400> SEQUENCE: 8

000

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:
      Hypothetical sequence used to illustrate the function of the
      invention

<400> SEQUENCE: 9

Leu Cys Asp Ala
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:
      Hypothetical sequence used to illustrate the function of the
      invention
```

-continued

```
<400> SEQUENCE: 10

Ile Cys Asp Ala
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence:
      Hypothetical sequence used to illustrate the function of the
      invention

<400> SEQUENCE: 11

Leu Cys Ala Asp
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence:
      Hypothetical sequence used to illustrate the function of the
      invention

<400> SEQUENCE: 12

Ile Cys Ala Asp
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence:
      Hypothetical sequence used to illustrate the function of the
      invention

<400> SEQUENCE: 13

Leu Cys Gly Glu
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence:
      Hypothetical sequence used to illustrate the function of the
      invention

<400> SEQUENCE: 14

Ile Cys Gly Glu
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:
      Hypothetical sequence used to illustrate the function of the
      invention

<400> SEQUENCE: 15

Leu Cys Glu Gly
1
```

```
<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence:
      Hypothetical sequence used to illustrate the function of the
      invention

<400> SEQUENCE: 16

Ile Cys Glu Gly
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence:
      Hypothetical sequence used to illustrate the function of the
      invention

<400> SEQUENCE: 17

Leu Cys Val Ser
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence:
      Hypothetical sequence used to illustrate the function of the
      invention

<400> SEQUENCE: 18

Ile Cys Val Ser
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence:
      Hypothetical sequence used to illustrate the function of the
      invention

<400> SEQUENCE: 19

Leu Cys Ser Val
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence:
      Hypothetical sequence used to illustrate the function of the
      invention

<400> SEQUENCE: 20

Ile Cys Ser Val
1

<210> SEQ ID NO 21
<211> LENGTH: 11
```

```
<212> TYPE: PRT
<213> ORGANISM: Homo sapiens
<220> FEATURE:
<221> NAME/KEY: misc_feature
<222> LOCATION: 1
<223> OTHER INFORMATION: Xaa = L or R

<400> SEQUENCE: 21

Xaa Gly Ala Asp Met Glu Asp Val Cys Gly Arg
1               5                   10

<210> SEQ ID NO 22
<211> LENGTH: 9
<212> TYPE: PRT
<213> ORGANISM: Homo sapiens
<220> FEATURE:
<221> NAME/KEY: misc_feature
<222> LOCATION: 1
<223> OTHER INFORMATION: Xaa = L or R

<400> SEQUENCE: 22

Xaa Gly Ala Asp Met Glu Asp Val Arg
1               5

<210> SEQ ID NO 23
<211> LENGTH: 9
<212> TYPE: PRT
<213> ORGANISM: Homo sapiens

<400> SEQUENCE: 23

Ala Phe Thr Tyr Ile Asn Leu Asp Lys
1               5

<210> SEQ ID NO 24
<211> LENGTH: 9
<212> TYPE: PRT
<213> ORGANISM: Homo sapiens

<400> SEQUENCE: 24

Ala Val Leu Gly Thr Ser Asn Phe Lys
1               5

<210> SEQ ID NO 25
<211> LENGTH: 9
<212> TYPE: PRT
<213> ORGANISM: Homo sapiens

<400> SEQUENCE: 25

Asp Ala Trp Gly Pro Gly Ala Ala Lys
1               5

<210> SEQ ID NO 26
<211> LENGTH: 13
<212> TYPE: PRT
<213> ORGANISM: Homo sapiens

<400> SEQUENCE: 26

Asp Glu Asn Leu Ala Leu Tyr Val Glu Asn Gln Phe Arg
1               5                   10

<210> SEQ ID NO 27
<211> LENGTH: 7
<212> TYPE: PRT
<213> ORGANISM: Homo sapiens

<400> SEQUENCE: 27
```

```
Asp Gly Phe Gln Pro Ser Arg
1               5

<210> SEQ ID NO 28
<211> LENGTH: 6
<212> TYPE: PRT
<213> ORGANISM: Homo sapiens

<400> SEQUENCE: 28

Asp Leu Asn Gln Tyr Arg
1               5

<210> SEQ ID NO 29
<211> LENGTH: 6
<212> TYPE: PRT
<213> ORGANISM: Homo sapiens

<400> SEQUENCE: 29

Asp Gln His Phe Val Lys
1               5

<210> SEQ ID NO 30
<211> LENGTH: 12
<212> TYPE: PRT
<213> ORGANISM: Homo sapiens

<400> SEQUENCE: 30

Asp Ser Ala Gln Asn Ser Val Ile Ile Val Asp Lys
1               5                   10

<210> SEQ ID NO 31
<211> LENGTH: 11
<212> TYPE: PRT
<213> ORGANISM: Homo sapiens

<400> SEQUENCE: 31

Glu Glu Pro Gly Glu Asp Phe Pro Ala Ala Arg
1               5                   10

<210> SEQ ID NO 32
<211> LENGTH: 15
<212> TYPE: PRT
<213> ORGANISM: Homo sapiens

<400> SEQUENCE: 32

Gly Phe Val Glu Pro Asp His Tyr Val Val Gly Ala Gln Arg
1               5                   10                  15

<210> SEQ ID NO 33
<211> LENGTH: 17
<212> TYPE: PRT
<213> ORGANISM: Homo sapiens

<400> SEQUENCE: 33

His Pro Val Thr Gly Gln Phe Leu Tyr Gln Asp Ser Asn Trp Ala Ser
1               5                   10                  15
Lys

<210> SEQ ID NO 34
<211> LENGTH: 6
<212> TYPE: PRT
<213> ORGANISM: Homo sapiens

<400> SEQUENCE: 34

Ile Pro Glu Leu Asn Lys
```

```
1               5

<210> SEQ ID NO 35
<211> LENGTH: 6
<212> TYPE: PRT
<213> ORGANISM: Homo sapiens

<400> SEQUENCE: 35

Ile Thr Phe Ala Glu Lys
1               5

<210> SEQ ID NO 36
<211> LENGTH: 11
<212> TYPE: PRT
<213> ORGANISM: Homo sapiens

<400> SEQUENCE: 36

Leu Ala Gln Met Phe Ser Asp Met Val Leu Lys
1               5                   10

<210> SEQ ID NO 37
<211> LENGTH: 14
<212> TYPE: PRT
<213> ORGANISM: Homo sapiens

<400> SEQUENCE: 37

Leu Ala Val Asp Glu Glu Glu Asn Ala Asp Asn Asn Thr Lys
1               5                   10

<210> SEQ ID NO 38
<211> LENGTH: 11
<212> TYPE: PRT
<213> ORGANISM: Homo sapiens

<400> SEQUENCE: 38

Leu Asp Ser Thr Asp Phe Thr Gly Thr Ile Lys
1               5                   10

<210> SEQ ID NO 39
<211> LENGTH: 14
<212> TYPE: PRT
<213> ORGANISM: Homo sapiens

<400> SEQUENCE: 39

Leu Phe Gly Asn Met Glu Gly Asp Cys Pro Ser Asp Trp Lys
1               5                   10

<210> SEQ ID NO 40
<211> LENGTH: 10
<212> TYPE: PRT
<213> ORGANISM: Homo sapiens

<400> SEQUENCE: 40

Leu Leu Asn Glu Asn Ser Tyr Val Pro Arg
1               5                   10

<210> SEQ ID NO 41
<211> LENGTH: 13
<212> TYPE: PRT
<213> ORGANISM: Homo sapiens

<400> SEQUENCE: 41

Leu Thr His Asp Val Glu Leu Asn Leu Asp Tyr Glu Arg
1               5                   10
```

```
<210> SEQ ID NO 42
<211> LENGTH: 10
<212> TYPE: PRT
<213> ORGANISM: Homo sapiens

<400> SEQUENCE: 42

Leu Thr Thr Asp Phe Gly Asn Ala Glu Lys
1               5                   10

<210> SEQ ID NO 43
<211> LENGTH: 8
<212> TYPE: PRT
<213> ORGANISM: Homo sapiens

<400> SEQUENCE: 43

Leu Thr Val Ser Asn Val Leu Lys
1               5

<210> SEQ ID NO 44
<211> LENGTH: 9
<212> TYPE: PRT
<213> ORGANISM: Homo sapiens

<400> SEQUENCE: 44

Leu Val His Ala Asn Phe Gly Thr Lys
1               5

<210> SEQ ID NO 45
<211> LENGTH: 7
<212> TYPE: PRT
<213> ORGANISM: Homo sapiens

<400> SEQUENCE: 45

Leu Tyr Trp Asp Asp Leu Lys
1               5

<210> SEQ ID NO 46
<211> LENGTH: 7
<212> TYPE: PRT
<213> ORGANISM: Homo sapiens

<400> SEQUENCE: 46

Met Val Thr Ser Glu Ser Lys
1               5

<210> SEQ ID NO 47
<211> LENGTH: 12
<212> TYPE: PRT
<213> ORGANISM: Homo sapiens

<400> SEQUENCE: 47

Gln Val Asp Gly Asp Asn Ser His Val Glu Met Lys
1               5                   10

<210> SEQ ID NO 48
<211> LENGTH: 16
<212> TYPE: PRT
<213> ORGANISM: Homo sapiens

<400> SEQUENCE: 48

Ser Ala Phe Ser Asn Leu Phe Gly Gly Glu Pro Leu Ser Tyr Thr Arg
1               5                   10                  15

<210> SEQ ID NO 49
```

-continued

```
<211> LENGTH: 10
<212> TYPE: PRT
<213> ORGANISM: Homo sapiens

<400> SEQUENCE: 49

Ser Gly Val Gly Thr Ala Leu Leu Leu Lys
1               5                   10

<210> SEQ ID NO 50
<211> LENGTH: 14
<212> TYPE: PRT
<213> ORGANISM: Homo sapiens

<400> SEQUENCE: 50

Ser Ser Gly Leu Pro Asn Ile Pro Val Gln Thr Ile Ser Arg
1               5                   10

<210> SEQ ID NO 51
<211> LENGTH: 13
<212> TYPE: PRT
<213> ORGANISM: Homo sapiens

<400> SEQUENCE: 51

Val Glu Tyr His Phe Leu Ser Pro Tyr Val Ser Pro Lys
1               5                   10

<210> SEQ ID NO 52
<211> LENGTH: 13
<212> TYPE: PRT
<213> ORGANISM: Homo sapiens

<400> SEQUENCE: 52

Val Ser Ala Ser Pro Leu Leu Tyr Thr Leu Ile Glu Lys
1               5                   10
```